(12) United States Patent
Zeidler et al.

(10) Patent No.: US 11,530,273 B2
(45) Date of Patent: Dec. 20, 2022

(54) ANTI-CD73 MONOCLONAL ANTIBODY, ENCODING NUCLEIC ACIDS AND METHOD FOR PRODUCING

(71) Applicant: HELMHOLTZ ZENTRUM MÜNCHEN—DEUTSCHES FORSCHUNGSZENTRUM FÜR GESUNDHEIT UND UMWELT (GMBH), Neuherberg (DE)

(72) Inventors: Reinhard Zeidler, Olching (DE); Bettina Von Neubeck, Blaustein (DE); Regina Feederle, Munich (DE); Stefanie Hauck, Munich (DE)

(73) Assignee: Helmholtz Zentrum München—Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 119 days.

(21) Appl. No.: 16/614,314

(22) PCT Filed: May 23, 2018

(86) PCT No.: PCT/EP2018/063498
§ 371 (c)(1),
(2) Date: Nov. 15, 2019

(87) PCT Pub. No.: WO2018/215535
PCT Pub. Date: Nov. 29, 2018

(65) Prior Publication Data
US 2020/0148781 A1 May 14, 2020

(30) Foreign Application Priority Data
May 23, 2017 (LU) ........................................ 100265

(51) Int. Cl.
*C07K 16/28* (2006.01)
*A61P 35/00* (2006.01)
(52) U.S. Cl.
CPC .......... *C07K 16/2896* (2013.01); *A61P 35/00* (2018.01); *C07K 2317/565* (2013.01); *C07K 2317/76* (2013.01); *C07K 2317/92* (2013.01)
(58) Field of Classification Search
CPC .......... C07K 16/2896; C07K 2317/565; C07K 2317/76; A61P 35/00
See application file for complete search history.

(56) References Cited

U.S. PATENT DOCUMENTS

2018/0237536 A1* 8/2018 Perrot ................ C07K 16/2896

FOREIGN PATENT DOCUMENTS

| WO | WO 2004/079013 A1 | 9/2004 |
| WO | WO 2016/081748 A2 | 5/2016 |
| WO | WO 2016/081748 A3 | 5/2016 |

OTHER PUBLICATIONS

Antonioli L, et al. (Feb. 1, 2016) Trends Cancer. 2(2):95-109. (doi:10.1016/j.trecan.2016.01.003).*
Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Clayton et al., "Cancer Exosomes Express CD39 and CD73, Which Suppress T Cells through Adenosine Production," J Immunol 187:676-683 (2011).
Database Medline Ludwig et al., "Expression of CD 73 (ecto-5'-nucleotidase) in 165 glioblastomas by immunohistochemistry and electronmicroscopic histochemistry," No. NLM10470109, dated May 1999, 2 pages.
Kummer et al., "Development and Properties of a Monoclonal Antibody Specific for Human Ecto-5'-Nucelotide," Immunobiol. 166:203-211 (1984).
Redzic et al., "Glioblastoma Extraccellular Vesicles: Reservoirs of Potential Biomarkers," Pharmacogenomics and Personalized Mecidine 7:65-77 (2014).
Smyth et al., "CD73 Expression on Extracellular Vesicles Derived from CD4+CD25+Foxp3+T Cells Contributes to their Regulatory Function," Eur. J. Immunol. 43:2430-2440 (2013).
Stagg et al., "Anti-CD73 Antibody Therapy Inhibits Breast Tumor Growth and Metastasis," PNAS 107(4):1547-1552 (2010).
Cushman, et al., Gene Expression Markers of Efficacy and Resistance to Cetuximab Treatment in Metastatic Colorectal Cancer: Results from CALGB 80203 (Alliance), Clinical Cancer Research, Mar. 1, 2015, pp. 1078-1086, vol. 21, No. 5.
Jalkanen, et al., Heparan Sulfate Proteoglycans from Mouse Mammery Epithelial Cells: Localization on the Cell Surface with a Monoclonal Antiboty, The Journal of Cell Biology, Sep. 1985, pp. 976-984, vol. 101.

(Continued)

*Primary Examiner* — Robert S Landsman
(74) *Attorney, Agent, or Firm* — Cooley LLP

(57) ABSTRACT

The present invention relates to improved anti-CD73 antibodies which, in comparison to prior art anti-CD73 antibodies bind to a membrane-bound form of CD73 protein having cancer-promoting role and inhibit its enzymatic activity, while essentially not inhibiting a soluble form of CD73 protein involved in cardioprotection. The present invention further relates to methods of generation of such specific anti-CD73 antibodies and uses thereof including uses as medicaments and in methods for treatment, amelioration, prophylaxis and diagnostics of cancer.

16 Claims, 20 Drawing Sheets
Specification includes a Sequence Listing.

(56) References Cited

OTHER PUBLICATIONS

Jalkanen, et al., Cell Surface Proteoglycan of Mouse Mammary Epithelial Cells is Shed by Cleavage of Its Matrix-Extodomain from its Membrane-associated Domain, The Journal of Cell Biology, Dec. 1987, pp. 3087-3096, vol. 105.

Loi, et al., CD73 promotes anthracycline resistance and poor prognosis in triple negative breast cancer, PNAS, Jul. 2, 2013, pp. 11091-11096, vol. 110, No. 27.

Mikhailov, et al., CD73 Participates in Cellular Multiresistance Program and Protects against TRAIL-Induced Apoptosis, The Journal of Immunology, 2008, pp. 464-475.

Quezada, et al., 5(-ectonucleotidase Mediates Multiple-Drug Resistance in Glioblastoma Multiforme Cells, J. Cell. Physiol., 2013, pp. 602-608, vol. 228.

* cited by examiner

Figure 11

SEQ ID NO:1:
GAGGTGCAGCTGGTGGAGTCTGGGGGAGGCTTAGTACAGCCTGGAAGGTCCATGAAACTCTC
CTGTGCAGCCTCAGGATTCACTTTCAGTTTTTATTATATGGCCTGGGTCCGCCAGGCTCCAAC
GAAGGGTCTGGAGTGGGTCGCATCCATTAGTACTGGTGGTGGTAACACTTACTATCGCGACTC
CGTGAAGGGCCGATTCACTATCTCCAGAGATGATGCAAAAAGCACCCTATACCTGCAAATGGA
CAGTCTGAGGTCTGAGGAAACGGCCACTTATTACTGTGCAAGA**CATGGGGGGGACTACTACG
GGTATAGAGGGGGCTACTTTGATTAC**TGGGACCAAGGAGTCATGGTCACAGTCTCCTCA

SEQ ID NO: 5:
GACATCCAGATGACCCAGACTCCATCCTCCATGCCTGCATCTCTGGGAGAGAGAGTCACCAT
CAGTTGTAGAGCAAGTCAGGGTATTAACAATTATCTAAACTGGTATCAGCAGAAGCCAGATG
GAACGATTAAACCCCTGATCTACTACACTTCCAATTTACAATCTGGTGTCCCATCAAGGTTCA
GTGGCAGTGGGTCTGGGACAGATTATTCTCTCACCATCAGCAGCCTGGAGCCTGAAGATTTT
GCAATGTATTACTGCCAACAGTATGATAATTCTCCGTACACGTTTGGAGCTGGGACCAAGCT
GGAACTGAAA

Figure 12

SEQ ID NO:9:

EVQLVESGGGLVQPGRSMKLSCAASGFTFSFYYMAWVRQAPTKGLEWVASISTGGGNTYYRDSV
KGRFTISRDDAKSTLYLQMDSLRSEETATYYCARHGGDYYGYRGGYFDYWDQGVMVTVSS

SEQ ID NO: 13:

DIQMTQTPSSMPASLGERVTISCRASQGINNYLNWYQQKPDGTIKPLIYYTSNLQSGVPSRFSGS
GSGTDYSLTISSLEPEDFAMYYCQQYDNSPYTFGAGTKLELK

Figure 13

Numbering & Regions

*Displaying 1 - 124 of 124 residues:*

| Query protein sequence & aligned codons | E gag | V gtg | Q cag | L ctg | V gtg | E gag | S tct | G ggg | G gga | G ggc | L tta | V gta | Q cag | P cct | G gga | R agg | S tcc | M atg | K aaa | L ctc |
|---|---|---|---|---|---|---|---|---|---|---|---|---|---|---|---|---|---|---|---|---|
| Chothia numbering | H1 | H2 | H3 | H4 | H5 | H6 | H7 | H8 | H9 | H10 | H11 | H12 | H13 | H14 | H15 | H16 | H17 | H18 | H19 | H20 |

CHOTHIA REGIONS: HFR1

| S tcc | C tgt | A gca | A gcc | S tca | G gga | F ttc | T act | F ttc | S agt | Y tat | Y tat | M atg | A gcc | W tgg | V gtc | R cgc | Q cag | A gct | P cca | T acg | K aag |
|---|---|---|---|---|---|---|---|---|---|---|---|---|---|---|---|---|---|---|---|---|---|
| H21 | H22 | H23 | H24 | H25 | H26 | H27 | H28 | H29 | H30 | H31 | H32 | H33 | H34 | H35 | H36 | H37 | H38 | H39 | H40 | H41 | H42 | H43 |

CDR-H1 / HFR2

Figure 13 (cont.)

* Predicted CK2 Phosphorylation site
† Predicted PKC Phosphorylation site
> Predicted TYR KIN Phosphorylation site
☐ Insertion
⇐ Unusual residue (<1% of sequences)

Accessions & Annotations

| | |
|---|---|
| Organism | *Unclassified* |
| Chain Type | Heavy |
| Human Subgroup | Heavy chain subgroup III |
| Identical Protein Sequences | None |

Figure 14

Numbering & Regions

*Displaying 1 - 107 of 107 residues:*

| Query protein sequence & aligned codons | D gac | I atc | Q cag | M atg | T acc | Q cag | T act | P cca | S tcc | S tcc | M atg | P cct | A gca | S tct | L ctg | G gga | E gag | R aga | V gtc | T acc |
|---|---|---|---|---|---|---|---|---|---|---|---|---|---|---|---|---|---|---|---|---|
| Chothia numbering | L1 | L2 | L3 | L4 | L5 | L6 | L7 | L8 | L9 | L10 | L11 | L12 | L13 | L14 | L15 | L16 | L17 | L18 | L19 | L20 |

CHOTHIA REGIONS — LFR1

| I atc | S agt | C tgt | R aga | A gca | S agt | Q cag | G ggt | I att | N aac | N aat | Y tat | L cta | N aac | W tgg | Y tat | Q cag | K aag | P cca | D gat | G gga | T acg |
|---|---|---|---|---|---|---|---|---|---|---|---|---|---|---|---|---|---|---|---|---|---|
| L21 | L22 | L23 | L24 | L25 | L26 | L27 | L28 | L29 | L30 | L31 | L32 | L33 | L34 | L35 | L36 | L37 | L38 | L39 | L40 | L41 | L42 | L43 |

CDR-L1 — LFR2

Figure 14 (cont.)

| I | K | P | L | Y | Y | I | T | S | N | L | Q | S | G | V | P | S | R | F | S | G | S | G |
|---|---|---|---|---|---|---|---|---|---|---|---|---|---|---|---|---|---|---|---|---|---|---|
| att | aaa | ccc | ctg | atc | tac | tac | act | tcc | aat | tta | caa | tct | ggt | gtc | cca | tca | agg | ttc | agt | ggc | agt | ggg |
| L44 | L45 | L46 | L47 | L48 | L49 | L50 | L51 | L52 | L53 | L54 | L55 | L56 | L57 | L58 | L59 | L60 | L61 | L62 | L63 | L64 | L65 | L66 |

CDR-L2 — LFR3

| S | G | T | D | Y | S | L | T | I | S | S | L | E | P | E | D | F | A | M | Y | Y | C | Q |
|---|---|---|---|---|---|---|---|---|---|---|---|---|---|---|---|---|---|---|---|---|---|---|
| tct | ggg | aca | gat | tat | tct | ctc | acc | atc | agc | agc | ctg | gag | cct | gaa | gat | ttt | gca | atg | tat | tac | tgc | caa |
| L67 | L68 | L69 | L70 | L71 | L72 | L73 | L74 | L75 | L76 | L77 | L78 | L79 | L80 | L81 | L82 | L83 | L84 | L85 | L86 | L87 | L88 | L89 |

CDR-L3

Figure 14 (cont.)

| Q | Y | D | N | S | P | Y | T | F | G | A | G | T | K | L | E | L | K |
|---|---|---|---|---|---|---|---|---|---|---|---|---|---|---|---|---|---|
| cag | tat | gat | aat | tct | ccg | tac | acg | ttt | gga | gct | ggg | acc | aag | ctg | gaa | ctg | aaa |
| L90 | L91 | L92 | L93 | L94 | L95 | L96 | L97 | L98 | L99 | L100 | L101 | L102 | L103 | L104 | L105 | L106 | L107 |

LFR4

✻ Predicted CK2 Phosphorylation site
✦ Predicted PKC Phosphorylation site

Accessions & Annotations

| Organism | Unclassified |
|---|---|
| Chain Type | Light |
| Human Subgroup | Kappa Light chain subgroup I |
| Identical Protein Sequences | None |

SEQUENCE LISTING

<160> NUMBER OF SEQ ID NOS: 18

<210> SEQ ID NO 1
<211> LENGTH: 372

```
<212> TYPE: DNA
<213> ORGANISM: Rattus norvegicus
<220> FEATURE:
<221> NAME/KEY: V_region
<222> LOCATION: (1)..(372)
<223> OTHER INFORMATION: VH region
<220> FEATURE:
<221> NAME/KEY: misc_feature
<222> LOCATION: (76)..(96)
<223> OTHER INFORMATION: DNA sequence encoding the VH complementary
      determining region 1 (H-CDR1)
<220> FEATURE:
<221> NAME/KEY: misc_feature
<222> LOCATION: (154)..(171)
<223> OTHER INFORMATION: DNA sequence encoding the VH complementary
      determining region 2 (H-CDR2)
<220> FEATURE:
<221> NAME/KEY: misc_feature
<222> LOCATION: (295)..(339)
<223> OTHER INFORMATION: DNA sequence encoding the VH complementary
      determining region 3 (H-CDR3)

<400> SEQUENCE: 1
gaggtgcagc tggtggagtc tgggggaggc ttagtacagc ctggaaggtc catgaaactc      60
tcctgtgcag cctcaggatt cactttcagt ttttattata tggcctgggt ccgccaggct     120
ccaacgaagg gtctggagtg ggtcgcatcc attagtactg gtggtggtaa cacttactat     180
cgcgactccg tgaagggccg attcactatc tccagagatg atgcaaaaag caccctatac     240
ctgcaaatgg acagtctgag gtctgaggaa acgccactt attactgtgc aagacatggg      300
ggggactact acgggtatag aggggggctac tttgattact gggaccaagg agtcatggtc     360
acagtctcct ca                                                         372

<210> SEQ ID NO 2
<211> LENGTH: 21
<212> TYPE: DNA
<213> ORGANISM: Rattus norvegicus
<220> FEATURE:
<221> NAME/KEY: misc_feature
<222> LOCATION: (1)..(21)
<223> OTHER INFORMATION: DNA sequence encoding the VH complementary
      determining region 1 (H-CDR1)

<400> SEQUENCE: 2
ggattcactt tcagttttta t                                                21

<210> SEQ ID NO 3
<211> LENGTH: 18
<212> TYPE: DNA
<213> ORGANISM: Rattus norvegicus
<220> FEATURE:
<221> NAME/KEY: misc_feature
<222> LOCATION: (1)..(18)
<223> OTHER INFORMATION: DNA sequence encoding the VH complementary
      determining region 2 (H-CDR2)

<400> SEQUENCE: 3
agtactggtg gtggtaac                                                    18

<210> SEQ ID NO 4
<211> LENGTH: 45
<212> TYPE: DNA
<213> ORGANISM: Rattus norvegicus
<220> FEATURE:
<221> NAME/KEY: misc_feature
<222> LOCATION: (1)..(45)
<223> OTHER INFORMATION: DNA sequence encoding the VH complementary
      determining region 3 (H-CDR3)
```

<400> SEQUENCE: 4 catgggggggg actactacgg gtatagaggg ggctactttg attac          45

<210> SEQ ID NO 5
<211> LENGTH: 321
<212> TYPE: DNA
<213> ORGANISM: Rattus norvegicus
<220> FEATURE:
<221> NAME/KEY: V_region
<222> LOCATION: (1)..(321)
<223> OTHER INFORMATION: VL region
<220> FEATURE:
<221> NAME/KEY: misc_feature
<222> LOCATION: (70)..(102)
<223> OTHER INFORMATION: DNA sequence encoding the VL complementary
      determining region 1 (L-CDR1)
<220> FEATURE:
<221> NAME/KEY: misc_feature
<222> LOCATION: (148)..(168)
<223> OTHER INFORMATION: DNA sequence encoding the VL complementary
      determining region 2 (L-CDR2)
<220> FEATURE:
<221> NAME/KEY: misc_feature
<222> LOCATION: (265)..(291)
<223> OTHER INFORMATION: DNA sequence encoding the VL complementary
      determining region 3 (L-CDR3)

<400> SEQUENCE: 5
gacatccaga tgacccagac tccatcctcc atgcctgcat ctctgggaga gagagtcacc    60
atcagttgta gagcaagtca gggtattaac aattatctaa actggtatca gcagaagcca   120
gatggaacga ttaaacccct gatctactac acttccaatt tacaatctgg tgtcccatca   180
aggttcagtg gcagtgggtc tgggacagat tattctctca ccatcagcag cctggagcct   240
gaagattttg caatgtatta ctgccaacag tatgataatt ctccgtacac gtttggagct   300
gggaccaagc tggaactgaa a                                             321

<210> SEQ ID NO 6
<211> LENGTH: 33
<212> TYPE: DNA
<213> ORGANISM: Rattus norvegicus
<220> FEATURE:
<221> NAME/KEY: misc_feature
<222> LOCATION: (1)..(33)
<223> OTHER INFORMATION: DNA sequence encoding the VL complementary
      determining region 1 (L-CDR1)

<400> SEQUENCE: 6
agagcaagtc agggtattaa caattatcta aac          33

<210> SEQ ID NO 7
<211> LENGTH: 21
<212> TYPE: DNA
<213> ORGANISM: Rattus norvegicus
<220> FEATURE:
<221> NAME/KEY: misc_feature
<222> LOCATION: (1)..(21)
<223> OTHER INFORMATION: DNA sequence encoding the VL complementary
      determining region 2 (L-CDR2)

<400> SEQUENCE: 7
tacacttcca atttacaatc t          21

<210> SEQ ID NO 8
<211> LENGTH: 27
<212> TYPE: DNA
<213> ORGANISM: Rattus norvegicus
<220> FEATURE:

```
<221> NAME/KEY: misc_feature
<222> LOCATION: (1)..(27)
<223> OTHER INFORMATION: DNA sequence encoding the VL complementary
      determining region 3 (L-CDR3)

<400> SEQUENCE: 8
caacagtatg ataattctcc gtacacg                                              27

<210> SEQ ID NO 9
<211> LENGTH: 124
<212> TYPE: PRT
<213> ORGANISM: Rattus norvegicus
<220> FEATURE:
<221> NAME/KEY: MISC_FEATURE
<222> LOCATION: (1)..(124)
<223> OTHER INFORMATION: VH region
<220> FEATURE:
<221> NAME/KEY: SITE
<222> LOCATION: (26)..(32)
<223> OTHER INFORMATION: VH complementary determining region 1 (VH CDR1)
<220> FEATURE:
<221> NAME/KEY: SITE
<222> LOCATION: (52)..(57)
<223> OTHER INFORMATION: VH complementary determining region 2 (H-CDR2)
<220> FEATURE:
<221> NAME/KEY: SITE
<222> LOCATION: (99)..(113)
<223> OTHER INFORMATION: VH complementary determining region 3 (H-CDR3)

<400> SEQUENCE: 9

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Phe Tyr
            20                  25                  30

Tyr Met Ala Trp Val Arg Gln Ala Pro Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asp Ala Lys Ser Thr Leu Tyr
65                  70                  75                  80

Leu Gln Met Asp Ser Leu Arg Ser Glu Glu Thr Ala Thr Tyr Tyr Cys
                85                  90                  95

Ala Arg His Gly Gly Asp Tyr Tyr Gly Tyr Arg Gly Gly Tyr Phe Asp
            100                 105                 110

Tyr Trp Asp Gln Gly Val Met Val Thr Val Ser Ser
        115                 120

<210> SEQ ID NO 10
<211> LENGTH: 7
<212> TYPE: PRT
<213> ORGANISM: Rattus norvegicus
<220> FEATURE:
<221> NAME/KEY: SITE
<222> LOCATION: (1)..(7)
<223> OTHER INFORMATION: VH complementary determining region 1 (H-CDR1)

<400> SEQUENCE: 10

Gly Phe Thr Phe Ser Phe Tyr
1               5

<210> SEQ ID NO 11
<211> LENGTH: 6
<212> TYPE: PRT
<213> ORGANISM: Rattus norvegicus
<220> FEATURE:
<221> NAME/KEY: SITE
```

-continued

```
<222> LOCATION: (1)..(6)
<223> OTHER INFORMATION: VH complementary determining region 2 (H-CDR2)

<400> SEQUENCE: 11

Ser Thr Gly Gly Gly Asn
1               5

<210> SEQ ID NO 12
<211> LENGTH: 15
<212> TYPE: PRT
<213> ORGANISM: Rattus norvegicus
<220> FEATURE:
<221> NAME/KEY: SITE
<222> LOCATION: (1)..(15)
<223> OTHER INFORMATION: VH complementary determining region 3 (H-CDR3)

<400> SEQUENCE: 12

His Gly Gly Asp Tyr Tyr Gly Tyr Arg Gly Gly Tyr Phe Asp Tyr
1               5                   10                  15

<210> SEQ ID NO 13
<211> LENGTH: 107
<212> TYPE: PRT
<213> ORGANISM: Rattus norvegicus
<220> FEATURE:
<221> NAME/KEY: MISC_FEATURE
<222> LOCATION: (1)..(107)
<223> OTHER INFORMATION: VL region
<220> FEATURE:
<221> NAME/KEY: SITE
<222> LOCATION: (24)..(34)
<223> OTHER INFORMATION: VL complementary determining region 1 (L-CDR1)
<220> FEATURE:
<221> NAME/KEY: SITE
<222> LOCATION: (50)..(56)
<223> OTHER INFORMATION: VL complementary determining region 2 (L-CDR2)
<220> FEATURE:
<221> NAME/KEY: SITE
<222> LOCATION: (89)..(97)
<223> OTHER INFORMATION: VL complementary determining region 3 (L-CDR3)

<400> SEQUENCE: 13

Asp Ile Gln Met Thr Gln Thr Pro Ser Ser Met Pro Ala Ser Leu Gly
1               5                   10                  15

Glu Arg Val Thr Ile Ser Cys Arg Ala Ser Gln Gly Ile Asn Asn Tyr
                20                  25                  30

Leu Asn Trp Tyr Gln Gln Lys Pro Asp Gly Thr Ile Lys Pro Leu Ile
            35                  40                  45

Tyr Tyr Thr Ser Asn Leu Gln Ser Gly Val Pro Ser Arg Phe Ser Gly
        50                  55                  60

Ser Gly Ser Gly Thr Asp Tyr Ser Leu Thr Ile Ser Ser Leu Glu Pro
65                  70                  75                  80

Glu Asp Phe Ala Met Tyr Tyr Cys Gln Gln Tyr Asp Asn Ser Pro Tyr
                85                  90                  95

Thr Phe Gly Ala Gly Thr Lys Leu Glu Leu Lys
            100                 105

<210> SEQ ID NO 14
<211> LENGTH: 11
<212> TYPE: PRT
<213> ORGANISM: Rattus norvegicus
<220> FEATURE:
<221> NAME/KEY: SITE
<222> LOCATION: (1)..(11)
<223> OTHER INFORMATION: VL complementary determining region 1 (L-CDR1)

<400> SEQUENCE: 14
```

Arg Ala Ser Gln Gly Ile Asn Asn Tyr Leu Asn
1               5                   10

<210> SEQ ID NO 15
<211> LENGTH: 7
<212> TYPE: PRT
<213> ORGANISM: Rattus norvegicus
<220> FEATURE:
<221> NAME/KEY: SITE
<222> LOCATION: (1)..(7)
<223> OTHER INFORMATION: VL complementary determining region 2 (L-CDR2)

<400> SEQUENCE: 15

Tyr Thr Ser Asn Leu Gln Ser
1               5

<210> SEQ ID NO 16
<211> LENGTH: 9
<212> TYPE: PRT
<213> ORGANISM: Rattus norvegicus
<220> FEATURE:
<221> NAME/KEY: SITE
<222> LOCATION: (1)..(9)
<223> OTHER INFORMATION: VL complementary determining region 3 (L-CDR3)

<400> SEQUENCE: 16

Gln Gln Tyr Asp Asn Ser Pro Tyr Thr
1               5

<210> SEQ ID NO 17
<211> LENGTH: 574
<212> TYPE: PRT
<213> ORGANISM: Homo sapiens
<220> FEATURE:
<221> NAME/KEY: MISC_FEATURE
<222> LOCATION: (1)..(574)
<223> OTHER INFORMATION: 5'-nucleotidase isoform 1 preproprotein,
      Accession: NP_002517

<400> SEQUENCE: 17

Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
        50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
            100                 105                 110

Met Ala Leu Gly Asn His Glu Phe Asp Asn Gly Val Glu Gly Leu Ile
        115                 120                 125

Glu Pro Leu Leu Lys Glu Ala Lys Phe Pro Ile Leu Ser Ala Asn Ile
    130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
        195                 200                 205

Thr Leu Asn Val Asn Lys Ile Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Gln Ala Tyr Ala Phe Gly Lys Tyr Leu Gly
        275                 280                 285

Tyr Leu Lys Ile Glu Phe Asp Glu Arg Gly Asn Val Ile Ser Ser His
    290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
            340                 345                 350

Cys Arg Phe Arg Glu Cys Asn Met Gly Asn Leu Ile Cys Asp Ala Met
        355                 360                 365

Ile Asn Asn Leu Arg His Thr Asp Glu Met Phe Trp Asn His Val
    370                 375                 380

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
        435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
        515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570

<210> SEQ ID NO 18
<211> LENGTH: 524

```
<212> TYPE: PRT
<213> ORGANISM: Homo sapiens
<220> FEATURE:
<221> NAME/KEY: MISC_FEATURE
<222> LOCATION: (1)..(524)
<223> OTHER INFORMATION: 5'-nucleotidase isoform 2 preproprotein,
      Accession: NP_001191742

<400> SEQUENCE: 18

Met Cys Pro Arg Ala Ala Arg Ala Pro Ala Thr Leu Leu Ala Leu
1               5                   10                  15

Gly Ala Val Leu Trp Pro Ala Ala Gly Ala Trp Glu Leu Thr Ile Leu
            20                  25                  30

His Thr Asn Asp Val His Ser Arg Leu Glu Gln Thr Ser Glu Asp Ser
        35                  40                  45

Ser Lys Cys Val Asn Ala Ser Arg Cys Met Gly Gly Val Ala Arg Leu
    50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
                115                 120                 125

Glu Pro Leu Leu Lys Glu Ala Lys Phe Pro Ile Leu Ser Ala Asn Ile
            130                 135                 140

Lys Ala Lys Gly Pro Leu Ala Ser Gln Ile Ser Gly Leu Tyr Leu Pro
145                 150                 155                 160

Tyr Lys Val Leu Pro Val Gly Asp Glu Val Val Gly Ile Val Gly Tyr
                165                 170                 175

Thr Ser Lys Glu Thr Pro Phe Leu Ser Asn Pro Gly Thr Asn Leu Val
                180                 185                 190

Phe Glu Asp Glu Ile Thr Ala Leu Gln Pro Glu Val Asp Lys Leu Lys
                195                 200                 205

Thr Leu Asn Val Asn Lys Ile Ile Ala Leu Gly His Ser Gly Phe Glu
        210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
                260                 265                 270

Arg Lys Val Pro Val Val Gln Ala Tyr Ala Phe Gly Lys Tyr Leu Gly
                275                 280                 285

Tyr Leu Lys Ile Glu Phe Asp Glu Arg Gly Asn Val Ile Ser Ser His
                290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
                340                 345                 350

Cys Arg Phe Arg Glu Cys Asn Met Gly Asn Leu Ile Cys Asp Ala Met
                355                 360                 365
```

```
Ile Asn Asn Asn Leu Arg His Thr Asp Glu Met Phe Trp Asn His Val
    370             375             380
Ser Met Cys Ile Leu Asn Gly Gly Gly Ile Arg Ser Pro Ile Asp Glu
385             390             395             400
Arg Asn Asn Gly Ile His Val Val Tyr Asp Leu Ser Arg Lys Pro Gly
            405             410             415
Asp Arg Val Val Lys Leu Asp Val Leu Cys Thr Lys Cys Arg Val Pro
            420             425             430
Ser Tyr Asp Pro Leu Lys Met Asp Glu Val Tyr Lys Val Ile Leu Pro
        435             440             445
Asn Phe Leu Ala Asn Gly Gly Asp Gly Phe Gln Met Ile Lys Asp Glu
    450             455             460
Leu Leu Arg His Asp Ser Gly Asp Gln Asp Ile Asn Val Val Ser Thr
465             470             475             480
Tyr Ile Ser Lys Met Lys Val Ile Tyr Pro Ala Val Glu Gly Arg Ile
            485             490             495
Lys Phe Ser Thr Gly Ser His Cys His Gly Ser Phe Ser Leu Ile Phe
            500             505             510
Leu Ser Leu Trp Ala Val Ile Phe Val Leu Tyr Gln
        515             520
```

ANTI-CD73 MONOCLONAL ANTIBODY, ENCODING NUCLEIC ACIDS AND METHOD FOR PRODUCING

CROSS-REFERENCE TO RELATED APPLICATIONS

This application is a U.S. national phase application of International PCT Patent Application No. PCT/EP2018/063498, filed May 23, 2018, which claims the benefit of priority to Luxembourg patent application no. 100265, filed May 23, 2017. These applications are incorporated herein by reference in their entireties.

This application contains a Sequence Listing in computer readable form, which is incorporated herein by reference.

STATEMENT REGARDING SEQUENCE LISTING

This application hereby incorporates by reference the sequence listing in the text file named Sequence Listing.txt filed herewith having a size of 18,271 bytes. The file was created on Nov. 15, 2019 and is submitted electronically via EFS-Web.

TECHNICAL FIELD

The present invention relates to improved anti-CD73 antibodies which, in comparison to prior art anti-CD73 antibodies bind to a membrane-bound form of CD73 protein having cancer-promoting role and specifically inhibit its enzymatic activity while essentially not inhibiting a soluble form of CD73 protein involved in cardioprotection. The present invention further relates to methods of generation of such specific anti-CD73 antibodies and uses thereof including uses as medicaments and in methods for treatment, amelioration, prophylaxis and diagnostics of cancer. Therefore, the anti-CD73 monoclonal antibody of the invention has a first-in-class potential as an immune checkpoint inhibitor for the treatment of cancer (e.g., AML, ALL) and other immune-mediated diseases as a single treatment or in combination with doxorubicin.

BACKGROUND OF THE INVENTION

There is great medical need for effective cancer therapies which provoke less serious adverse side effects. Current therapies usually lack specificity and are often ineffective due to intrinsic or acquired resistance against chemo- und radiotherapy.

The ecto-nucleotidase CD73 is a glycosyl phosphatidylinositol (GPI)-linked, membrane-bound glycoprotein that converts extracellular adenosine monophosphate (AMP) to adenosine (ADO). A soluble form of CD73 can be shed from the membrane through proteolytic cleavage or hydrolysis of the GPI anchor. CD73 is the rate-limiting enzyme in the decay of ATP to adenosine, which exerts different cancer-promoting modes-of-action. The molecule is expressed on immune effector cells, where it contributes to immunosuppressive effects and hyporesponsiveness, but is also expressed at high levels across various types of cancer. CD73 is also found in a variety of tissues, including colon, brain, kidney, liver, lung, and heart, but also on leukocytes as well as on endothelium. There is evidence that the expression and function of this enzyme are upregulated under hypoxic conditions, as well as by the presence of several pro-inflammatory mediators.

Within the tumor microenvironment, adenosine produced by CD73 promotes tumor growth and survival, while suppressing antitumor immune responses. CD73 was found overexpressed in a broad range of cancer cells and blockade of this enzyme has been shown to alter the immunosuppressive capacity of tumors. Cancer cells induce an immunosuppressive environment to foster their own growth and to evade immune recognition. Therefore, CD73 (also known as NT5E) is a potent immunosuppressor. CD73 is an ectoenzyme, normally expressed on endothelial and immune cells, where it contributes to immune equilibrium. For example, CD73 plays a central role in the regulation of Treg activity (Deaglio et al., 2007, Wang et al., 2011) and the hyporesponsiveness of anergic T cells (Martinez et al., 2012). Thus, CD73 (or ecto-5'-nucleotidase or 5'-NT) having EC 3.1.3.5 enzymatic activity, is a widely expressed ecto-enzyme that catalyzes the dephosporylation of adenosine monophosphate to adenosine, which exerts different immunosuppressive and cancer-promoting modes-of-action (FIG. 1). The molecule is either constitutively expressed or induced on immune effector cells, where it contributes to immunosuppressive effects and hyporesponsiveness.

On the other hand, CD73 is overexpressed across various types of cancer (Stagg et al., 2013) and generally associated with a poor clinical prognosis (Ren et al., 2016). The immunosuppressive tumor milieu contains high levels of ADO, and targeted CD73 blockade promotes anti-tumor immunity by reducing ADO accumulation. In cancer, CD73 presumably exerts a dual function: firstly, it is expressed and exerts enzymatic activity on tumor-infiltrating stromal cells that constitute the neoplastic microenvironment; and secondly, it is highly expressed on cancer cells and directly stimulates their growth in an autocrine fashion (Stagg et al., 2010; Stagg et al., 2012). In addition, CD73 activity blunts tumor-specific Tcell responses (Jin et al., 2010) and interferes with apoptosis and metastasis (Antonioli et al., 2013). In fact, various preclinical models have demonstrated the value of CD73 as therapeutic target for cancer treatment (Zhang, 2010). Accordingly, it has been shown that anti-CD73 mAbs reduce tumor growth and metastasis in animal models (Stagg et al., 2010).

CD73 overexpression is also associated with chemoresistance of cancer cells, including breast cancer (Loi et al., 2013)) colorectal cancer (Cushman et al., 2015) and glioblastoma (Quezada et al., 2013) among others. Notably, CD73 has also been found overexpressed in leukemia cells resistant against TRAIL-induced apoptosis (Mikhailov et al., 2008). Currently, there are efforts towards the clinical translation of anti-CD73 therapy with antibodies, either alone or in combination with other checkpoint inhibitors. CD73-blocking mAbs constitute valuable anticancer tools, which may become an integral part of chemoradiation, molecular targeted therapies and other immunotherapeutic strategies.

For these reasons, CD73 is regarded as promising molecular target for immunotherapeutic (adjuvant) strategies, e.g. with blocking monoclonal antibodies (mAb). However, functional and thus conformation-specific, mAbs against structurally complex membrane proteins like G-protein coupled receptors (GPCRs) or membrane-tethered enzymes like CD73 are extremely hard to obtain by conventional immunization technologies.

On the other hand, a soluble form of CD73, which can be shed from the membrane through proteolytic cleavage or hydrolysis of the GPI anchor, has been reported to have a cardioprotective role. Accordingly, it is undesirable to block the soluble form of CD73 in order to avoid potential cardio-related adverse side effects. Furthermore, since most of CD73 protein in cells exist in a membrane-bound form, such membrane-bound form constitutes a primary target form for CD73 inactivation in cancer therapy. Several anti-CD73 mAbs are known in art (WO2016081748), neither of which, however, can specifically inhibit membrane-bound form of CD73 protein, while essentially not inhibiting enzymatic activity of a soluble form of CD73 protein.

The present application satisfies this demand by the provision of the antibodies that do not essentially inhibit a soluble form of CD73 protein, while inhibiting enzymatic activity of a membrane-bound form of CD73 as described herein below, characterized in the claims and illustrated by the appended Examples and Figures.

Extracellular Vesicles (EVs) are membrane-surrounded vesicles that are released by cells including cancer cells and contain functional proteins of their cell of origin. EVs most probably constitute a mixture of vesicles like exosomes and microvesicles, which differ in the morphogenesis pathways, their composition and probably their biological function. EVs are rich in membranes and membrane proteins and have been described to exert various immunological effects. Furthermore, EVs carry various membrane proteins in their physiological conformation. But EVs also contain various classes of functional nucleic acids which, after EVs are engulfed by the target cells, can be translated into functional protein (in case of mRNAs) or exert regulatory function (in case of e.g. micro-RNAs). Therefore, EVs are nowadays regarded as relevant and potent conveyors of (complex) information from a cell of origin to a target cells.

The inventors of the present invention developed an immunization strategy involving tumor-derived EVs for the generation of monoclonal antibodies (mAbs) with therapeutic and/or diagnostic potential. Using this strategy, the inventors generated a monoclonal antibody termed "22E6" that does not essentially inhibit a soluble form of CD73 protein such that it can inter alia produce adenosine involved in cardioprotection, whereas it binds to a membrane-bound form of CD73 protein and specifically inhibits its enzymatic activity. This 22E6 mAb is contemplated herein to be a superior molecule for use in interference with cancer resistance and further clinical use in mono- and combinational therapies. Furthermore, since it is undesirable to block the soluble form of CD73 due to its reported role in cardioprotection 22E6 mAb is particularly advantageous over the existing CD73 monoclonal antibodies binding and inhibiting both soluble and membrane-bound forms of CD73.

Sequence of the 22E6 mAb according to the present invention clearly differs from those of the sequences of known antibodies. Therefore, 22E6 mAb is the first and only antibody that selectively inhibits the membrane-tethered CD73, but not the soluble form of CD73. Given that both forms of the molecule are structurally similar and only differ by the presence or absence of a GPI-anchor, developing a functional antibody that selectively blocks the membranous form is completely new and unexpected.

SUMMARY OF THE INVENTION

The present invention relates to an anti-CD73 antibody or antigen binding portion thereof, wherein said anti-CD73 antibody or antigen binding portion thereof exhibits one or more of the following properties:
i) specifically inhibits enzymatic activity of a membrane-bound form of CD73;
ii) does not essentially inhibit a soluble form of CD73 protein, wherein inhibits enzymatic activity of a membrane-bound form of CD73;
iii) does not essentially inhibit a soluble form of CD73 protein, wherein binds to a membrane-bound form of CD73 protein and inhibits enzymatic activity of said membrane-bound form of CD73.

The present application satisfies this demand by the provision of the antibodies described herein below, characterized in the claims and illustrated by the appended Examples and Figures.

Overview of the Sequence Listing

SEQ ID NO: 1 is the DNA sequence encoding VH region of the mAb 22E6.

SEQ ID NO: 2 is the DNA sequence encoding the VH complementary determining region 1 (H-CDR1) of the mAb 22E6.

SEQ ID NO: 3 is the DNA sequence encoding the VH complementary determining region 2 (H-CDR2) of the mAb 22E6.

SEQ ID NO: 4 is the DNA sequence encoding the VH complementary determining region 3 (H-CDR3) of the mAb 22E6.

SEQ ID NO: 5 is the DNA sequence encoding VL region of the mAb 22E6.

SEQ ID NO: 6 is the DNA sequence encoding the VL complementary determining region 1 (L-CDR1) of the mAb 22E6.

SEQ ID NO: 7 is the DNA sequence encoding the VH complementary determining region 2 (L-CDR2) of the mAb 22E6.

SEQ ID NO: 8 is the DNA sequence encoding the VH complementary determining region 3 (L-CDR3) of the mAb 22E6.

SEQ ID NO: 9 is the amino acid sequence of the VH region of the mAb 22E6.

SEQ ID NO: 10 is the amino acid sequence of the VH complementary determining region 1 (H-CDR1) of the mAb 22E6.

SEQ ID NO: 11 is the amino acid sequence of the VH complementary determining region 2 (H-CDR2) of the mAb 22E6.

SEQ ID NO: 12 is the amino acid sequence of the VH complementary determining region 3 (H-CDR3) of the mAb 22E6.

SEQ ID NO: 13 is the amino acid sequence of the VL region of the mAb 22E6.

SEQ ID NO: 14 is the amino acid sequence of the VL complementary determining region 1 (L-CDR1) of the mAb 22E6.

SEQ ID NO: 15 is the amino acid sequence of the VL complementary determining region 2 (L-CDR2) of the mAb 22E6.

SEQ ID NO: 16 is the amino acid sequence of the VL complementary determining region 3 (L-CDR3) of the mAb 22E6.

SEQ ID NO: 17 is the amino acid sequence of the 5'-nucleotidase isoform 1 of *Homo sapiens* preproprotein, Accession: NP_002517.

SEQ ID NO: 18 is the amino acid sequence of the 5'-nucleotidase isoform 2 of *Homo sapiens* preproprotein, Accession: NP_001191742.

BRIEF DESCRIPTION OF THE DRAWINGS

FIG. 11: Nucleotide sequences of the variable parts of the immunoglobulin genes encoding light and heavy chains of 22E6. CDRs are marked in bold. Heavy chain: SEQ ID NO: 1, light chain: SEQ ID NO: 5.

FIG. 12: Amino acid sequences of the variable parts of the light and heavy chains of 22E6. CDRs are marked in bold. Heavy chain: SEQ ID NO: 9, light chain: SEQ ID NO: 13.

FIG. 14: Numbering of amino acids in the light chain (SEQ ID NO: 13) and unusual amino acid residues therein.

DETAILED DESCRIPTION OF THE INVENTION

Definitions

Figure 1:
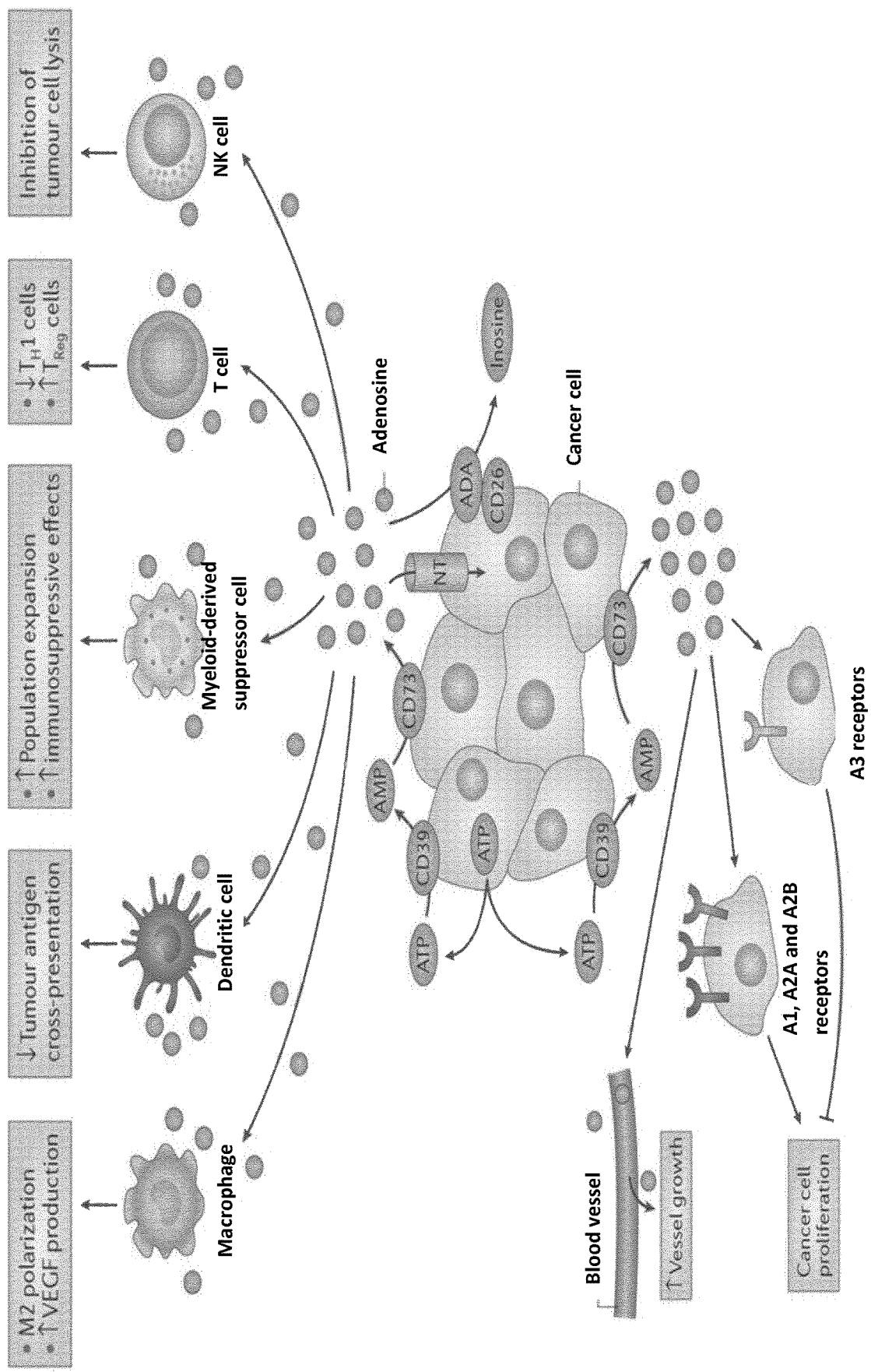
FIG. 1: The many functions of adenosine in the tumor environment as adapted from Antonioli et al., 2013.

An "extracellular vesicle" is a membrane-surrounded vesicle that is released by cells, including cancer cells and contains functional proteins of their cell of origin.

An "antibody" when used herein is a protein comprising one or more polypeptides (comprising one or more binding domains, preferably antigen binding domains) substantially or partially encoded by immunoglobulin genes or fragments of immunoglobulin genes. The term "immunoglobulin" (Ig) is used interchangeably with "antibody" herein. The recognized immunoglobulin genes include the kappa, lambda, alpha, gamma, delta, epsilon and mu constant region genes, as well as myriad immunoglobulin variable region genes. In particular, an "antibody" when used herein, is typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2, with IgG being preferred in the context of the present invention. An antibody of the present invention is also envisaged which has an IgE constant domain or portion thereof that is bound by the Fc epsilon receptor I. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each light chain includes an N-terminal variable (V) domain (VL) and a constant (C) domain (CL). Each heavy chain includes an N-terminal V domain (VH), three or four C domains (CHs), and a hinge region. The constant domains are not involved directly in binding an antibody to an antigen, but can exhibit various effector functions, such as participation of the antibody dependent cellular cytotoxicity (ADCC). If an antibody should exert ADCC, it is preferably of the IgG1 subtype, while the IgG4 subtype would not have the capability to exert ADCC.

The term "antibody" also includes, but is not limited to, but encompasses monoclonal, monospecific, poly- or multispecific antibodies such as bispecific antibodies, humanized, camelized, human, single-chain, chimeric, synthetic, recombinant, hybrid, mutated, grafted, and in vitro generated antibodies, with chimeric or humanized antibodies being preferred. The term "humanized antibody" is commonly defined for an antibody in which the specificity encoding CDRs of HC and LC have been transferred to an appropriate human variable frameworks ("CDR grafting"). The term "antibody" also includes scFvs, single chain antibodies, diabodies or tetrabodies, domain antibodies (dAbs) and nanobodies. In terms of the present invention, the term "antibody" shall also comprise bi-, tri- or multimeric or bi-, tri- or multifunctional antibodies having several antigen binding sites.

Furthermore, the term "antibody" as employed in the invention also relates to derivatives of the antibodies (including fragments) described herein. A "derivative" of an antibody comprises an amino acid sequence which has been altered by the introduction of amino acid residue substitutions, deletions or additions. Additionally, a derivative encompasses antibodies which have been modified by a covalent attachment of a molecule of any type to the antibody or protein. Examples of such molecules include sugars, PEG, hydroxyl-, ethoxy-, carboxy- or amine-groups but are not limited to these. In effect the covalent modifications of the antibodies lead to the glycosylation, pegylation, acetylation, phosphorylation, amidation, without being limited to these.

The antibody of the present invention is preferably an "isolated" antibody. "Isolated" when used to describe antibodies disclosed herein, means an antibody that has been identified, separated and/or recovered from a component of its production environment. Preferably, the isolated antibody is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step.

As used herein the term "antigen binding portion" refers to a fragment of immunoglobulin (or intact antibody), and encompasses any polypeptide comprising an antigen-binding fragment or an antigen-binding domain. Preferably, the fragment such as Fab, F(ab'), F(ab')$_2$, Fv, scFv, Fd, disulfide-linked Fvs (sdFv), and other antibody fragments that retain antigen-binding function as described herein. Typically, such fragments would comprise an antigen-binding domain and have the same properties as the antibodies described herein.

Accordingly, said fragment is preferably also capable to bind to a membrane-bound form of CD73 protein.

As used herein, the term "specifically binds" refers to antibodies or fragments or derivatives thereof that specifically bind to CD73 protein and do not specifically bind to another protein. The antibodies or fragments or derivatives thereof according to the invention bind to a CD73 protein through the variable domain of the antibody.

As used herein, the term "specifically inhibits" refers to antibodies or fragments or derivatives thereof that specifically inhibit a membrane-bound form of CD73 protein and do not specifically inhibit a soluble form of CD73. The antibodies or fragments or derivatives thereof according to the invention inhibit a membrane-bound form of CD73 protein through the variable domain of the antibody.

The pairing of a VH and VL together forms a single antigen-binding site. The CH domain most proximal to VH is designated as CH1. Each L chain is linked to an H chain by one covalent disulfide bond, while the two H chains are linked to each other by one or more disulfide bonds depending on the H chain isotype. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR 1, CDR2, and CDR3. Accordingly, CDR constituents on the heavy chain are referred to as H1 or H-CDR1, H2 or H-CDR2 and H3 or H-CDR3, while CDR constituents on the light chain are referred to as L1 or L-CDR1, L2 or L-CDR2, and L3 or L-CDR3.

The term "variable" refers to the portions of the immunoglobulin domains that exhibit variability in their sequence and that are involved in determining the specificity and binding affinity of a particular antibody (i.e., the "variable domain(s)"). Variability is not evenly distributed throughout the variable domains of antibodies; it is concentrated in sub-domains of each of the heavy and light chain variable regions. These sub-domains are called "complementarity determining regions" (CDRs).

The terms "CDR", and its plural "CDRs", refer to a complementarity determining region (CDR) of which three make up the binding character of a light chain variable region (L1-CDRL1, L2-CDR and L3-CDR) and three make up the binding character of a heavy chain variable region (H1-CDR, H2-CDR and H3-CDR). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., loc. cit.; Chothia et al., J. Mol. Biol, 1987, 196: 901; and MacCallum et al, J. Mol. Biol, 1996, 262: 732). However, the numbering in accordance with the so-called Kabat system is preferred.

Preferred variable regions of an antibody of the present invention are shown in SEQ ID Nos. 9, 10, 11, 12, 13, 14, 15, 16.

The more conserved (i.e., non-hypervariable) portions of the variable domains are called the "framework" regions (FRM). The variable domains of naturally occurring heavy and light chains each comprise four FRM regions, largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding site (see Kabat et al., loc. cit.). The constant domains are not directly involved in antigen binding, but exhibit various effector functions, such as, for example, antibody-dependent, cell-mediated cytotoxicity and complement activation.

The term "binding domain" characterizes in connection with the present invention a domain of a polypeptide which specifically binds/interacts with a given target epitope. An "epitope" is antigenic and thus the term epitope is sometimes also referred to herein as "antigenic structure" or "antigenic determinant". Thus, the binding domain is an "antigen-interaction-site". The term "antigen-interaction-site" defines, in accordance with the present invention, a motif of a polypeptide, which is able to specifically interact with a specific antigen or a specific group of antigens, e.g. the identical antigen in different species. Said binding/interaction is also understood to define a "specific recognition".

The term "epitope" also refers to a site on an antigen (in the context of the present invention, the antigen is a membrane-bound form of CD73 protein) to which the antibody molecule binds. Preferably, an epitope is a site on a molecule (in the context of the present invention, the antigen is a membrane-bound form of CD73 protein) against which an antibody or antigen binding portion thereof, preferably an antibody will be produced and/or to which an antibody will bind. For example, an epitope can be recognized by a antibody or antigen binding portion thereof. A "linear epitope" is an epitope where an amino acid primary sequence comprises the epitope recognized. A linear epitope typically includes at least 3, and more usually, at least 5, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically, a conformational epitope comprises an increased number of amino acids relative to a linear epitope. Regarding recognition of conformational epitopes, the antibody or antigen binding portion thereof recognizes a 3-dimensional structure of the antigen, preferably a peptide or protein or fragment thereof (in the context of the present invention, the antigen is a membrane-bound form of CD73 protein). For example, when a protein molecule folds to form a three-dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography 2-dimensional nuclear magnetic resonance spectroscopy and site-directed spin labelling and electron paramagnetic resonance spectroscopy.

As used herein, the term "affinity" refers to the binding strength between the variable regions of one heavy and one light chain of an antibody or fragment or derivative thereof and their antigen (e.g., membrane-bound form of CD73) and is measured in vitro. Affinity determines the strength of the interaction between an epitope and an antibody's antigen binding site. Affinity can be calculated using the following formula:

$$KA=[AB-AG]/[AB]*[AG]=k_{on}/k_{off}$$

wherein:
KA=affinity constant
[AB]=molar concentration of unoccupied binding sites on the antibody
[AG]=molar concentration of unoccupied binding sites on the antigen
[AB−AG]=molar concentration of the antibody-antigen complex As used herein, the term "avidity" refers to the measurement of the overall strength of an antibody-antigen complex, which in effect depends on the parameters (1) affinity of the antibody for the epitope, (2) valency of the antibody and antigen and (3) the structural arrangement of the interacting parts.

The term "specifically" in this context means that the antibody or antigen binding portion thereof inhibits enzymatic activity of a membrane-bound form of CD73 protein, but does not essentially inhibit another protein. The term "another protein" includes any protein including proteins closely related to or being homologous to a CD73 protein against which the antibody or antigen binding portion thereof is directed to. However, the term "another protein" does not include that the antibody or antigen binding portion thereof cross-reacts with a membrane-bound form of CD73 protein from a species different from that against which the antibody or antigen binding portion thereof was generated.

Thus, cross-species specific antibody or antigen binding portion thereof directed against membrane-bound form of CD73 protein are preferably contemplated by the present invention.

The term "does not essentially inhibit" means that the anti-CD73 antibody or antigen binding portion thereof of the present invention does not inhibit a soluble form of CD73 protein, i.e., shows inhibition of enzymatic activity of a soluble form of CD73 protein of less than 30%, preferably 20%, more preferably 10%, particularly preferably less than 9, 8, 7, 6 or 5%.

Specific binding is believed to be effected by specific motifs in the amino acid sequence of the binding domain and the antigen bind to each other as a result of their primary, secondary or tertiary structure as well as the result of secondary modifications of said structure. The specific interaction of the antigen-interaction-site with its specific antigen may result as well in a simple binding of said site to the antigen. Moreover, the specific interaction of the antigen-interaction-site with its specific antigen may alternatively result in the initiation of a signal, e.g. due to the induction of a change of the conformation of the antigen, an oligomerization of the antigen, etc. A preferred example of a binding domain in line with the present invention is an antibody.

Typically, binding is considered specific when the binding affinity is higher than $10^{-6}$M. Preferably, binding is considered specific when binding affinity is about $10^{-11}$ to $10^{-8}$ M (KD), preferably of about $10^{-11}$ to $10^{-9}$ M. If necessary, nonspecific binding can be reduced without substantially affecting specific binding by varying the binding conditions.

Whether the antibody or antigen binding portion thereof specifically reacts as defined herein above can easily be tested, inter alia, by comparing the reaction of said antibody or antigen binding portion thereof with a membrane-bound form of CD73 protein with the reaction of said antibody or antigen binding portion thereof with (an) other protein(s), e.g., a soluble form of CD73 protein.

The term polypeptide" is equally used herein with the term "protein". Proteins (including fragments thereof, preferably biologically active fragments, and peptides, usually having less than 30 amino acids) comprise one or more amino acids coupled to each other via a covalent peptide bond (resulting in a chain of amino acids). The term "polypeptide" as used herein describes a group of molecules, which, for example, consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "polypeptide" and "protein" also refer to naturally modified polypeptides/proteins wherein the modification is effected e.g. by post-translational modifications like glycosylation, acetylation, phosphorylation and the like. Such modifications are well known in the art.

An "antibody" when used herein is a protein comprising one or more polypeptides (comprising one or more binding domains, preferably antigen binding domains) substantially or partially encoded by immunoglobulin genes or fragments of immunoglobulin genes. The term "immunoglobulin" (Ig) is used interchangeably with "antibody" herein.

The recognized immunoglobulin genes include the kappa, lambda, alpha, gamma, delta, epsilon and mu constant region genes, as well as myriad immunoglobulin variable region genes.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gin, Gly, His, Met, Phe, Ser, Thr, Trp, and Tyr).

The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al, Nature, 1989, 342: 877; Martin and Thornton, J. Mol. Biol, 1996, 263: 800, each of which is incorporated by reference in its entirety). Furthermore, there is a relationship between the adopted loop structure and the amino acid sequences surrounding it. The conformation of a particular canonical class is determined by the length of the loop and the amino acid residues residing at key positions within the loop, as well as within the conserved framework {i.e., outside of the loop). Assignment to a particular canonical class can therefore be made based on the presence of these key amino acid residues. The term "canonical structure" may also include considerations as to the linear sequence of the antibody, for example, as catalogued by Kabat (Kabat et al, loc. cit.). The Kabat numbering scheme (system) is a widely-adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al and/or revealed by other techniques, for example, crystallography and two or three-dimensional computational modeling. Accordingly, a given antibody sequence may be placed into a canonical class which allows for, among other things, identifying appropriate chassis sequences {e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature.

CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in Sequences of Proteins of immunological Interest, US Department of Health and Human Services (1991), eds. Kabat et al. Another standard for characterizing the antigen binding site is to refer to the hypervariable loops as described by Chothia. See, e.g., Chothia, et al. (1992; J. Mol. Biol. 227:799-817; and Tomlinson et al. (1995) EMBO J. 14:4628-4638. Still another standard is the AbM definition used by Oxford Molecular's AbM antibody modelling software. See, generally, e.g., Protein Sequence and Structure Analysis of Antibody Variable Domains. In: Antibody Engineering Lab Manual (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

The sequence of antibody genes after assembly and somatic mutation is highly varied, and these varied genes are estimated to encode $10^{10}$ different antibody molecules (Immunoglobulin Genes, 2nd ed., eds. Jonio et al., Academic Press, San Diego, Calif., 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

"Polyclonal antibodies" or "polyclonal antisera" refer to immune serum containing a mixture of antibodies specific for one (monovalent or specific antisera) or more (polyvalent antisera) antigens which may be prepared from the blood of animals immunized with the antigen or antigens.

Furthermore, the term "antibody" as employed in the invention also relates to derivatives or variants of the antibodies described herein which display the same specificity as the described antibodies. Examples of "antibody variants" include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function (s) (see, e.g., U.S. Pat. No. 5,648,260).

The terms "antigen-binding domain", "antigen binding portion", "antigen-binding fragment" and "antibody binding region" when used herein refer to a part of an antibody molecule that comprises amino acids responsible for the specific binding between antibody and antigen. The part of the antigen that is specifically recognized and bound by the antibody is referred to as the "epitope" as described herein above. As mentioned above, an antigen-binding domain may typically comprise an antibody light chain variable region (VL) and an antibody heavy chain variable region (VH); however, it does not have to comprise both. Fd fragments, for example, have two VH regions and often retain some antigen-binding function of the intact antigen-binding domain. Examples of antigen-binding fragments of an antibody include (1) a Fab fragment, a monovalent fragment having the VL, VH, CL and CH1 domains; (2) a F(ab')2 fragment, a bivalent fragment having two Fab fragments linked by a disulfide bridge at the hinge region; (3) a Fd fragment having the two VH and CH1 domains; (4) a Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv). Although the two domains of the Fv fragment, VL and VH> are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci USA 85:5879-5883). These antibody fragments are obtained using conventional techniques known to those with skill in the art, and the fragments are evaluated for function in the same manner as are intact antibodies.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies of interest herein include "primitized" antibodies comprising variable domain antigen-binding sequences derived from a non-human primate (e.g., Old World Monkey, Ape etc.) and human contant region sequences.

"Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

The term "human antibody" includes antibodies having variable and constant regions corresponding substantially to human germline immunoglobulin sequences known in the art, including, for example, those described by Kabat et al. (See Kabat, et al. (1991) loc. cit.). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

As used herein, "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term thus preferably excludes sequences generated by genomic rearrangement in an immune cell.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). In one embodiment, the bispecific antibody comprises a first binding domain polypeptide, such as a Fab' fragment, linked via an immunoglobulin constant region to a second binding domain polypeptide.

Antibodies described herein may be used for forming bispecific molecules. An anti-CD73 antibody, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody described herein may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Immunoconjugates and antibody derivatives. Antibodies described herein can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing. The detectable labels can be any of the various types used currently in the field of in vitro diagnostics, including particulate labels including metal sols such as colloidal gold, isotopes, chromophores including fluorescent markers, biotin, luminescent markers, phosphorescent markers and the like, as well as enzyme labels that convert a given substrate to a detectable marker, and polynucleotide tags that are revealed following amplification such as by polymerase chain reaction. A biotinylated antibody would then be detectable by avidin or streptavidin binding. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO 92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, and WO96/33735.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See e.g., Morrison et al., Proc. Natl. Acad. ScL U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., EP 171496; EP 173494, GB 2177096. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., Proc. Natl. Acad. Sci. U.S.A., 80: 7308-7312, 1983; Kozbor et al, Immunology Today, 4: 7279, 1983; Olsson et al., Meth. Enzymol., 92: 3-16, 1982), and may be made according to the teachings of WO 92/06193 or EP 239400).

An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) J. Mol. Biol. 227:776-798; Cook, G. P. etai. (1995) Immunol. Today Vol. 16 (5): 237-242; Chothia, et al. (1992) J. Mol. Biol. 227: 799-817; and Tomlinson et al. (1995) EMBO J. 14:4628-4638. The V BASE directory provides a comprehensive directory of human immunoglobulin variable region sequences (compiled by Tomlinson, L A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

It is known that an antibody may exert effector functions. Accordingly, it is envisaged that an antibody of the invention can exert one or more effector functions due to its immunoglobulin constant or Fc region. Alternatively, in certain embodiments it is envisaged that an antibody can contain an altered immunoglobulin constant or Fc region. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, Annu. Rev. Immunol 9:457-92, 1991; Capel et al., Immunomethods 4:25-34, 1994; and de Haas et al., J. Lab. Clin. Med. 126:330-41, 1995).

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g., B cell receptors); and B cell activation. In order to exert effector functions an antibody, so to say, recruits effector cells.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g., as described in Gazzano-Santoro et al., J. Immunol. Methods 202: 163 (1996) may be performed.

"Antibody-dependent cell-mediated cytotoxicity" or ADCC refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRE only, whereas monocytes express FcγRI, FcγRII and FcγRIII. Fc expression on hematopoietic cells is summarized in Table 3 on page 464 of Ravetch and Kinet, Annu. Rev. Immunol. 9: 457-92 (1991). To assess ADCC activity of a molecule of interest, an in vitro ACDD assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95: 652-656 (1998).

"Effector cells", preferably human effector cells are leukocytes which express one or more FcRs and perform effector functions. Preferably, the cells express at least FcγRm and perform ADCC effector function. Examples of human leukocytes which mediate ADCC include peripheral blood mononuclear cells (PBMC), natural killer (NK) cells, monocytes, cytotoxic T cells and neutrophils, with PBMCs and MNK cells being preferred. The effector cells may be isolated from a native source, e.g., blood.

Techniques for production of antibodies, including polyclonal, monoclonal, humanized, bispecific and heteroconjugate antibodies are known in the art, some of which are exemplified below.

1) Polyclonal Antibodies:

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysien residues), glutaraldehyde, succinic anhydride. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

For example, the animals are immunized against the antigen, immunogenic conjugates, or derivatives by combining the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites.

Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable used to enhance the immune response. However, in a preferred aspect, the present invention relates to a method for the generation (or preparation) of an antibody against membrane-bound form of CD73 protein comprising: i) immunizing a non-human mammal with extracellular vesicles (EVs) comprising a membrane-bound form of CD73 derived from a cancer cell; and ii) isolating an antibody obtained in step (i). Further preferably, the method for preparation of the antibody as described above further comprises a step of determining whether the antibody obtained in step (ii) exhibits one or more of the properties according to item 1 below.

The term "immunizing" refers to the step or steps of administering one or more antigens (in case of the present invention a membrane-bound form of CD73 protein or one or more immunogenic fragments thereof) to a non-human animal so that antibodies can be raised in the animal.

The terms "antigen" and "immunogen" are used interchangeably herein to refer to a molecule or substance which induces an immune response (preferably an antibody response) in an animal, preferably a non-human animal immunized therewith (i.e. the antigen is "immunogenic" in the animal). In case of the present invention when an antibody is generated against membrane-bound form of CD73 protein the antigen is preferably a membrane-bound form of CD73 protein. Preferably, the antigen used for immunizing a non-human animal is a purified antigen. A "purified" antigen is one which has been subjected to one or more purification procedures. The purified antigen may be "homogeneous", which is used herein to refer to a composition comprising at least about 70% to about 100% by weight of the antigen of interest, based on total weight of the composition, preferably at least about 80% to about 100% by weight of the antigen of interest.

Generally, immunizing comprises injecting the antigen or antigens into the non-human animal. Immunization may involve one or more administrations of the antigen or antigens.

Specifically, the non-human animal is preferably immunized at least two, more preferably three times with said polypeptide (antigen), optionally in admixture with an adjuvant. An "adjuvant" is a nonspecific stimulant of the immune response. The adjuvant may be in the form of a composition comprising either or both of the following components: (a) a substance designed to form a deposit protecting the antigen (s) from rapid catabolism (e.g. mineral oil, alum, aluminium hydroxide, liposome or surfactant (e.g. pluronic polyol) and (b) a substance that nonspecifically stimulates the immune response of the immunized host animal (e.g. by increasing lymphokine levels therein).

Exemplary molecules for increasing lymphokine levels include lipopolysaccharide (LPS) or a Lipid A portion thereof; Bordetella pertussis; pertussis toxin; *Mycobacterium tuberculosis*; and muramyl dipeptide (MDP). Examples of adjuvants include Freund's adjuvant (optionally comprising killed *M. tuberculosis*; complete Freund's adjuvant); aluminium hydroxide adjuvant; and monophosphoryl Lipid A-synthetic trehalose dicorynomylcolate (MPL-TDM).

The "non-human animal" to be immunized herein is preferably a rodent. A "rodent" is an animal belonging to the rodentia order of placental mammals. Exemplary rodents include mice, rats, guinea pigs, squirrels, hamsters, ferrets etc, with mice being the preferred rodent for immunizing according to the method herein. Other non-human animals which can be immunized herein include non-human primates such as Old World monkey (e.g. baboon or macaque, including Rhesus monkey and cynomolgus monkey; see U.S. Pat. No. 5,658,570); birds (e.g. chickens); rabbits; goats; sheep; cows; horses; pigs; donkeys; dogs etc.

The antibody that can be obtained by the preferred method is a polyclonal antibody or polyclonal serum (e.g., obtainable from a rodent, more preferably from a rabbit, goat or sheep) or, if antibody-producing cells are isolated from the non-human animal, a monoclonal antibody (e.g., obtainable from a rodent, more preferably from a mouse, rat or sheep) can be produced as is commonly known in the art and described herein. Preferably, the animal is immunized with a composition comprising a mixture of the two or more different antigens; and step (b) comprises fusing immune cells from the immunized animal with myeloma cells in order to generate hybridoma cell lines producing the monoclonal antibodies.

The term "immune cells" refers to cells which are capable of producing antibodies. The immune cells of particular interest herein are lymphoid cells derived, e.g. from spleen, peripheral blood lymphoctes (PBLs), lymph node, inguinal node, Peyers patch, tonsil, bone marrow, cord blood, pleural effusions and tumor-infiltrating lymphocytes (TIL).

By "screening" is meant subjecting one or more monoclonal antibodies (e.g., purified antibody and/or hybridoma culture supernatant comprising the antibody) to one or more assays which determine qualitatively and/or quantitatively the ability of an antibody to bind to an antigen of interest.

By "immuno-assay" is meant an assay that determines binding of an antibody to an antigen, wherein either the antibody or antigen, or both, are optionally adsorbed on a solid phase (i. e., an "immunoadsorbent" assay) at some stage of the assay. Exemplary such assays include ELISAs, radioimmunoassays (RIAs), and FACS assays. Given the above, the present invention provides thus a monoclonal or polyclonal antibody obtainable by the aforedescribed methods for the generation of an antibody, i.e., by immunizing a non-human animal as described before. Hence, the term "antibody" when used herein also encompasses an antibody (monoclonal or polyclonal) obtainable by the methods for the generation of an antibody against membrane-bound form of CD73, preferably human membrane-bound form of CD73.

2) Monoclonal Antibodies:

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., Nature, 256: 495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphoctyes are then fused with an immortalized cell line using a suitable fusing agent, such as polyethylene glycol, to form a hybridoma cell. Goding, Monoclonal Antibodies: Principles and Practice, Academic Press (1986), pp. 59-103.

Immortalized cell lines are usually transformed mammalian cell, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The culture medium in which the hybridoma cells are cultured can be assayed for the presence of monoclonal antibodies directed again desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., Curr. Opinion in Immunol., 5: 256-262 (1993) and Pluckthun, Immunol. Revs. 130: 151-188 (1992).

In a further embodiment, antibodies can be isolated from antibody phage libraries generated using the techniques described in McCafferty et al., Nature, 348: 552-554 (1990). Clackson et al., Nature, 352: 624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Biotechnology, 10: 779-783 (1992)), as well as combinatorial infection and in vivo recombination as a strategy for constructing very large phage libraries (Waterhouse et al., Nucl. Acids Res., 21: 2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc. Natl Acad. Sci. USA, 81: 6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

3) Humanized Antibodies:

The antibodies of the invention may further comprise humanized or human antibodies. Humanized forms of non-human (e.g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321: 522-525 (1986); Riechmann et al., Nature 332: 323-327 (1988); Verhoeyen et al., Science 239: 1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol.) 151: 2296 (1993); Chothia et al., J. Mol. Biol., 196: 901 (1987).

Another method uses a particular framework derived from the consensus sequence of all human antibodies of a particular subgroup of light or heavy chains. The same framework may be used for several different humanized antibodies. Carter et al., Proc. Natl. Acad. Sci. USA, 89: 4285 (1992); Presta et al., J. Immunol., 151: 2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i. e., the analysis of residues that influence the ability of the candidate immunoglobulin to bind its antigen. In this way, FR residues can be selected and combined from the recipient and import sequences so that the desired antibody characteristic, such as increased affinity for the target antigen (s), is achieved. In general, the CDR residues are directly and most substantially involved in influencing antigen binding.

Various forms of the humanized antibody are contemplated. For example, the humanized antibody may be an antibody fragment, such as an Fab, which is optionally conjugated with one or more cytotoxic agent (s) in order to generate an immunoconjugate.

Alternatively, the humanized antibody may be an intact antibody, such as an intact IgGI antibody.

4) Human Antibodies:

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255-258 (1993); Bruggermann et al., Year in Immun., 7: 33 (1993); U.S. Pat. No. 5,591,669 and WO 97/17852.

Alternatively, phage display technology can be used to produce human antiobdies and antibody fragments in vitro, from immunoglublin variable (V) domain gene repertoires from unimmunized donors. McCafferty et al., Nature 348: 552-553 (1990); Hoogenboom and Winter, J. Mol. Biol. 227: 381 (1991). According to this technique, antibody V domain genes are cloned in-frame into either a major or minor coat protein gene of a filamentous bacteriophage, such as M13, and displayed as functional antibody fragments on the surface of the phage particle. Because the filamentous particle contains a single-stranded DNA copy of the phage genome, selections based on the functional properties of the antibody also result in seletion of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Curr. Opin Struct. Biol. 3: 564-571 (1993). Several sources of V-gene segments can be used for phage display. Clackson et al., Nature 352: 624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222: 581-597 (1991), or Griffith et al., EMBO J. 12: 725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., J. Immunol. 147 (1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resemble that seen in human in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., Bio/Technology 10: 779-783 (1992); Lonberg et al., Nature 368: 856-859 (1994); Morrison, Nature 368: 812-13 (1994), Fishwild et al., Nature Biotechnology 14: 845-51 (1996), Neuberger, Nature Biotechnology 14: 826 (1996) and Lonberg and Huszar, Intern. Rev. Immunol. 13: 65-93 (1995). Finally, human antibodies may also be generated in vitro by activated B cells (see U.S. Pat. Nos. 5,567,610 and 5,229,275).

5) Antibody Fragments:

In certain circumstances there are advantages to using antibody fragments, rather than whole antibodies. Smaller fragment size allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., J Biochem Biophys. Method. 24: 107-117 (1992); and Brennan et al., Science 229: 81 (1985)). However, these fragments can now be produced directly by recombinant host cells. Fab, Fv and scFv antibody fragments can all be expressed in and secreted from E. coli, thus allowing the facile production of large amounts of these fragments.

Antibody fragments can be isolated from the antibody phage libraries discussed above.

Alternatively, Fab'-SH fragments can be directly recovered from E. coli and chemically coupled to form F (ab') 2 fragments (Carter et aL, BiolTechnology 10: 163-167 (1992)).

According to another approach, F (ab') 2 fragments can be isolated directly from recombinant host cell culture. Fab and F (ab') 2 with increase in vivo half-life is described in U.S. Pat. No. 5,869,046. In other embodiments, the antibody of choice is a single chain Fv fragment (scFv); see WO 93/16185; U.S. Pat. Nos. 5,571,894 and 5,587,458. The antibody fragment may also be a"linear antibody", e.g., as described in U.S. Pat. No. 5,641,870. Such linear antibody fragments may be monospecific or bispecific.

6) Bispecific and Polyspecific Antibodies:

Bispecific antibodies (BsAbs) are antibodies that have binding specificities for at least two different epitopes, including those on the same or another protein. Alternatively, one arm can be armed to bind to the target antigen, and another arm can be combined with an arm that binds to a triggering molecule on a leukocyte such as a T-cell receptor molecule (e.g., CD3), or Fc receptors for IgG (FcγR) such as FcγRI (CD64), FcγRII (CD32) and FcγRin (CD16), so as to focus and localize cellular defense mechanisms to the target antigen-expressing cell. Such antibodies can be derived from full length antibodies or antibody fragments (e.g. F(ab')$_2$ bispecific antibodies).

Bispecific antibodies may also be used to localize cytotoxic agents to cells which express the target antigen. Such antibodies possess one arm that binds the desired antigen and another arm that binds the cytotoxic agent (e.g., methotrexate).

Methods for making bispecific antibodies are known in the art. Traditional production of full length bispecific antibodies is based on the coexpression of two immunoglobulin heavy chain-light chain pairs, where the two chains have different specificities. Millstein et al., Nature, 305: 537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690. For further details of generating bispecific antibodies, see, for example, Suresh et al., Methods in Enzymology 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains (s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., Science 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., J. Exp. Med. 175: 217-225 (1992) describes the production of fully humanized bispecific antibody F (ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., J. Immunol., 148 (5): 1547-1553 (1992).

The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Natl. Acad. Sci. USA, 90: 6444-6448 (1993) has provided an alternative mechanism for making bispecific/bivalent antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific/bivalent antibody fragments by the use of single-chain Fv (sFv) dimers has also been reported. See Gruber et al., J. Imnzunol., 152: 5368 (1994).

Antibodies with more than two valencies are contemplated. For example, trispecific antibodies can be prepared. Tutt et al., J. Immunol. 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein.

Another bispecific antibody of interest binds the protein of interest and further binds Human Serum Albumine.

The "diabody" technology described by Hollinger et al., Proc. Natl. Acad. Sci. USA, 90: 6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152: 5368 (1994).

Antibodies with more than two valencies are contemplated. For example, trispecific antibodies can be prepared. Tutt et al. J. Immunol. 147: 60 (1991).

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain (s) comprise two or more variable domains. For instance, the polypeptide chain (s) may comprise VDI $(X1_n$-VD2-$(X2)n$-Fc, wherein VDI is a first variable domain, VD2 is a second variable domain, Fc is one polypeptide chain of an Fc region, X1 and X2 represent an amino acid or polypeptide, and n is 0 or 1. For instance, the polypeptide chain (s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

7) Heteroconjugate Antibodies:

Heteroconjugate antibodies are also within the scope of the present invention.

Heteroconjugate antibodies are composed of two covalently joined antibodies. For example, one of the antibodies in the heteroconjugate can be coupled to avidin, the other to biotin. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

For additional antibody production techniques, see Antibodies: A Laboratory Manual, eds. Harlow et al., Cold Spring Harbor Laboratory, 1988. The present invention is not necessarily limited to any particular source, method of production, or other special characteristics of an antibody.

The antibody of the present invention is preferably an "isolated" antibody. "Isolated" when used to describe antibodies disclosed herein, means an antibody that has been identified, separated and/or recovered from a component of its production environment. Preferably, the isolated antibody is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step.

Amino acid sequence modifications of the CD73 antibodies described herein are contemplated. For example, it may be desirable to improve the binding affinity and/or other biological properties of the antibody. Amino acid sequence variants of the CD73 antibody are prepared by introducing appropriate nucleotide changes into the CD73 antibody nucleic acid, or by peptide synthesis.

Such modifications include, for example, deletions from, and/or insertions into, and/or substitutions of, residues within the amino acid sequences of the CD73 antibody. Any combination of deletion, insertion, and substitution is made to arrive at the final construct, provided that the final construct possesses the desired characteristics. The amino acid changes also may alter post-translational processes of the CD73 antibody, such as changing the number or position of glycosylation sites.

A useful method for identification of certain residues or regions of the CD73 antibody that are preferred locations for mutagenesis is called "alanine scanning mutagenesis" as described by Cunningham and Wells in Science, 244: 1081-1085 (1989).

Here, a residue or group of target residues within the CD73 antibody are identified (e.g., charged residues such as arg, asp, his, lys, and glu) and replaced by a neutral or negatively charged amino acid (most preferably alanine or polyalanine) to affect the interaction of the amino acids with epitope.

Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyse the performance of a mutation at a given site, ala scanning or random mutagenesis is conducted at a target codon or region and the expressed CD73 antibody variants are screened for the desired activity.

Amino acid sequence insertions include amino- and/or carboxyl-terminal fusions ranging in length from one, two, three, four, five, six, seven, eight, nine or ten residues to polypeptides containing a hundred or more residues, as well as intrasequence insertions of single or multiple amino acid residues. An insertional variant of the CD73 antibody molecule include the fusion to the N- or C-terminus of the antibody to an enzyme or a fusion to a polypeptide which increases the serum half-life of the antibody.

Another type of variant is an amino acid substitution variant. These variants have at least one, two, three, four, five, six, seven, eight, nine or ten amino acid residues in the CD73 antibody molecule replaced by a different residue. The sites of greatest interest for substitutional mutagenesis include the CDRs of the heavy and/or light chain, in particular the hypervariable regions, but FR alterations in the heavy and/or light chain are also contemplated.

For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

Generally, if amino acids are substituted in one or more or all of the CDRs of the heavy and/or light chain, it is preferred that the then-obtained "substituted" sequence is at least 60% (e.g., at least 65%, at least 70%, at least 75%, at least 80%, at least 85%, at least 90%, at least 95%, at least 96%, at least 97%, at least 98%, at least 99% or 100%), more preferably 65%, even more preferably 70%, particularly preferable 75%, more particularly preferable 80% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the CD73 antibody may have different degrees of identity to their substituted sequences, e.g., CDRL1 may have 80%, while CDRL3 may have 90%.

Preferred substitutions (or replacements) are conservative substitutions. However, any substitution (including non-conservative substitution or one or more from the "exemplary substitutions listed in Table 1, below) is envisaged as long as the CD73 antibody retains its capability to specifically inhibit membrane bound for of CD73 protein and/or its CDRs have an identity to the then substituted sequence (at least 60% ((e.g., at least 65%, at least 70%, at least 75%, at least 80%, at least 85%, at least 90%, at least 95%, at least 96%, at least 97%, at least 98%, at least 99% or 100%), more preferably 65%, even more preferably 70%, particularly preferable 75%, more particularly preferable 80% identical to the "original" CDR sequence).

Conservative substitutions are shown in Table I under the heading of "preferred substitutions". If such substitutions result in a change in biological activity, then more substantial changes, denominated "exemplary substitutions" in Table 1, or as further described below in reference to amino acid classes, may be introduced and the products screened for a desired characteristic.

TABLE I

Amino Acid Substitutions

| Original | Exemplary Substitutions | Preferred Substitutions |
|---|---|---|
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |

TABLE I-continued

Amino Acid Substitutions

| Original | Exemplary Substitutions | Preferred Substitutions |
|---|---|---|
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gin, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the CD73 antibody also may be substituted, generally with serine, to improve the oxidative stability of the molecule and prevent aberrant crosslinking. Conversely, cysteine bond (s) may be added to the antibody to improve its stability (particularly where the antibody is an antibody fragment such as an Fv fragment).

A particularly preferred type of substitutional variant involves substituting one or more hypervariable region residues of a parent antibody (e. g. a humanized or human antibody). Generally, the resulting variant (s) selected for further development will have improved biological properties relative to the parent antibody from which they are generated. A convenient way for generating such substitutional variants involves affinity maturation using phage display. Briefly, several hypervariable region sites (e. g. 6-7 sites) are mutated to generate all possible amino acid substitutions at each site. The antibody variants thus generated are displayed in a monovalent fashion from filamentous phage particles as fusions to the gene III product of M13 packaged within each particle.

The phage-displayed variants are then screened for their biological activity (e. g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and, e.g., human CD73. Such contact residues and neighbouring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Other modifications of the antibody are contemplated herein. For example, the antibody may be linked to one of a variety of nonproteinaceous polymers, e. g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly (methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980).

The CD73 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of E. coli.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies (Lindmark et al., J. Immunol. Meth. 62: 1-13 (1983)). Protein G is recommended for all mouse isotypes and for human gamma3 (Guss et al., EMBO J. 5: 15671575 (1986)).

The term "position" when used in accordance with the present invention means the position of an amino acid within an amino acid sequence depicted herein. The term "corresponding" as used herein also includes that a position is not only determined by the number of the preceding nucleotides/amino acids.

The position of a given amino acid in accordance with the present invention which may be substituted may very due to deletion or addition of amino acids elsewhere in the CD73 polypeptide.

Thus, under a "corresponding position" in accordance with the present invention it is to be understood that amino acids may differ in the indicated number but may still have similar neighbouring amino acids. Said amino acids which may be exchanged, deleted or added are also comprised by the term "corresponding position".

In order to determine whether an amino acid residue in a given CD73 amino acid sequence corresponds to a certain position in the amino acid sequence of SEQ ID NOs: 9 or 13, the skilled person can use means and methods well-known in the art, e.g., alignments, either manually or by using computer programs such as BLAST2.0, which stands for Basic Local Alignment Search Tool or ClustalW or any other suitable program which is suitable to generate sequence alignments.

As used herein, the term "% identity" refers to the percentage of identical amino acid residues at the corresponding position within the sequence when comparing two amino acid sequences with an optimal sequence alignment as exemplified by the ClustalW or X techniques as available from www.clustal.org, or equivalent techniques. For example, in case of CDR alignments, each of the CDRs (from the heavy and light chain variable region, respectively) shown in SEQ ID NOs. 9-16 serves as reference sequence for a CDR sequence of interest of a heavy or light chain variable region, respectively, e.g. H-CDR1 of SEQ ID NO. 10 is aligned with an H-CDR1 of interest. Accordingly, both sequences (reference sequence and sequence of interest) are aligned, identical amino acid residues between both sequences are identified and the total number of identical amino acids is divided by the total number of amino acids (amino acid length) of SEQ ID NO. 9-16, respectively, dependent on whether H-CDR1, H-CDR2, H-CDR3, L-CDR1, L-CDR2, or L-CDR3 are aligned. The result of this division is a percent value, i.e. percent identity value/degree.

In a further aspect, the present invention relates to a nucleic acid encoding the antibody or antigen binding portion thereof described herein. The present invention also provides nucleic acid sequences encoding the antibody described herein. As used herein, the terms "nucleic acids" or "nucleotide sequences" refer to DNA molecules (e.g. cDNA or genomic DNA), RNA (mRNA), combinations thereof or hybrid molecules comprised of DNA and RNA. The nucleic acids can be double- or single-stranded and may contain double- and single-stranded fragments at the same time. Most preferred are double stranded DNA molecules. According to the present invention, a nucleic acid sequence which codes for an inventive antibody comprises nucleotides which encode at least those parts of the antibody which confer the specific binding properties of the antibody according to the invention. Preferably the nucleic acid sequence according to the invention encodes the variable regions, preferably at least the CDRs as described herein.

Said nucleic acid molecule is preferably comprised in a vector which is preferably comprised in a host cell. Said host cell is capable of expressing the antibody or antigen binding portion thereof. For that purpose, the nucleic acid molecule is operatively linked with control sequences.

As used herein, the term "host cell" is intended to refer to a cell into which a nucleic acid encoding the antibody or antigen binding portion thereof of the invention is introduced by way of transformation, transfection and the like. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, the term "expression" includes any step involved in the production of a antibody or antigen binding portion thereof including, but not limited to, transcription, post-transcriptional modification, translation, post-translational modification, and secretion. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Suitable host cells include prokaryotic and eukaryotic host cells including yeasts, fungi, insect cells and mammalian cells.

Antibody or antigen binding portion thereofs can be produced in bacteria, in particular when glycosylation and Fc effector function are not needed.

After expression, the antibody or antigen binding portion thereof, preferably an antibody is isolated from the *E. coli* cell paste in a soluble fraction and can be purified through, e.g., a protein A or G column depending on the isotype. Final purification can be carried out similar to the process for purifying antibody expressed e.g., in CHO cells. In addition to prokaryotes, eukaryotic microbes such as filamentous fungi or yeast are suitable cloning or expression hosts for the antibody or antigen binding portion thereof of the present invention.

*Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e. g., *K. lactis, K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus; yarrowia* (EP 402 226); *Pichia pastoris* (EP 183 070); *Candida; Trichoderma reesia* (EP 244 234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibody or antigen binding portion thereofs, preferably antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, *petunia*, tomato, *Arabidopsis* and tobacco can also be utilized as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/-DHFR (CHO, Urlaub et al., Proc. Natl. Acad. Sci. USA 77: 4216 (1980)); mouse sertoli cells (TM4, Mather, Biol. Reprod. 23: 243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL5 1); TRI cells (Mather et al., Annals N. Y Acad. Sci. 383: 44-68 (1982)); MRC 5 cells; FS4 cells; and a human hepatoma line (Hep G2).

When using recombinant techniques, the antibody or antigen binding portion thereof can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody or antigen binding portion thereof, preferably an antibody prepared from the host cells can be purified using, for example, hydroxylapatite chromatography, gel electrophoresis, dialysis, and affinity chromatography, with affinity chromatography being the preferred purification technique.

The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62: 1-13 (1983)). Protein G is recommended for all mouse isotypes and for human γ3 (Guss et al., EMBO J. 5: 15671575 (1986)). The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose. Where the antibody comprises a CH3 domain, the Bakerbond ABXMresin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromato-focusing, SDS-PAGE, and ammonium sulfate precipitation are also available depending on the antibody to be recovered.

In another aspect, the present invention provides an antibody or antigen binding portion thereof of the present invention for use as diagnostic composition. Accordingly, the antibody or antigen binding portion thereof can be used in diagnostic assays for their antigen, e.g., detecting its expression in specific cells, tissues, or serum.

Various diagnostic assay techniques known in the art may be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-158). The antibody or antigen binding portion thereof used in the diagnostic assays can be labeled with a detectable moiety. For example, antibody or antigen binding portion thereofs may be modified with detectable markers, including ligand groups (e.g., biotin), fluorophores and chromophores, radioisotopes, electron-dense reagents, or enzymes. Enzymes are detected by their activity. For example, horseradish peroxidase is detected by its ability to convert tetramethylbenzidine (TMB) to a blue pigment, quantifiable with a spectrophotometer. Other suitable binding partners include biotin and avidin, IgG and protein A, and other receptor-ligand pairs known in the art.

The detectable moiety should be capable of producing, either directly or indirectly, a detectable signal. For example, the detectable moiety may be a radioisotope, such as $^3$H, $^{14}$C, $^{32}$P $^{35}$S or $^{125}$I a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed.

The antibody or antigen binding portion thereof of the present invention when administered to a subject is preferably in the form of a composition. The composition is preferably suitable for pharmaceutical use and administration to subjects.

Accordingly, the antibody or antigen binding portion thereof of the present invention is envisaged for use in therapy. Accordingly, the present invention envisages a pharmaceutical composition (or medicament) comprising the antibody or antigen binding portion thereof described herein.

In yet another embodiment, the invention provides a method of treating a subject comprising administering a therapeutically effective amount of the antibody or antigen binding portion thereof of the present invention, wherein the subject has cancer, e.g., in which CD73 is involved.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

Cancers whose growth may be inhibited using the antibodies of the invention include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of luekemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (MI), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation, lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary, plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 or PD-L1 antibody), and recurrent cancers.

In preferred embodiments a cancer selected from a group consisting of: leukemia, lymphoma, myeloma, breast cancer, colorectal cancer, glioblastoma, ovarian cancer, hematological cancer, epithelial cancer, pancreatic cancer, bladder cancer, uterine/cervical cancer, ovarian cancer, prostate cancer, testicular cancer, esophageal cancer, gastrointestinal cancer, colon cancer, kidney cancer, head and neck cancer, lung cancer, stomach cancer, germ cell cancer, bone cancer, liver cancer, thyroid cancer, skin cancer, neoplasm of the central nervous system, sarcoma, and virus-related cancer.

In further preferred embodiments a cancer is leukemia and is selected from a group consisting of: Acute myeloid leukemia (AML); Chronic myeloid leukemia (CML); Acute lymphocytic leukemia (ALL); Chronic lymphocytic leukemia (CLL).

The term "subject" is intended to include living organisms. Examples of subjects include mammals, e.g., humans, dogs, cows, horses, pigs, sheep, goats, cats, mice, rabbits, rats, and transgenic non-human animals. In preferred embodiments of the invention, the subject is a human.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the subject's own immune system. The term "patient" includes human and other mammalian subjects that receive either prophylactic or therapeutic treatment.

The appropriate dosage, or therapeutically effective amount, of the antibody or antigen binding portion thereof will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations. The pharmaceutical composition can be administered as a sole therapeutic or in combination with additional therapies as needed. An example of a therapy that could be applied in combination with the pharmaceutical composition of the present invention is an anti-TNF-antibody, a soluble TNF-receptor, an anti-GM-CSF antibody, an anti-IL-1 antibody, an anti-IL-25 antibody, an anti-IL-17 antibody and/or methotrexate. The pharmaceutical compositions of this invention are particularly useful for parenteral administration, i.e., subcutaneously, intramuscularly, intravenously, intra-articular and/or intra-synovial. Parenteral administration can be by bolus injection or continuous infusion.

In a preferred embodiment, the injection is a local or non-systemic injection, preferably into the synovia, synovia space, synovial fluid, or synovial joint, subchondral area, osteochondral defect, intra-articular space preferably of the knee, shoulder, hip, thumb, temporomandibular joint or facet joint, annulus fibrosus, nucleus pulposus, nucleus pulposus space, intradiscally or transdically. More preferably, the injection is an intra-articular injection preferably into the knee, shoulder, hip, thumb, temporomandibular joint or facet joint. Further preferably, the intra-articular injection is an intra-articular injection into the synovial fluid of the facet joint or the temporomandibular joint. A further preferred injection is an injection into the subsynovial room or area or an injection into the chondral or osteochondral defect. Also encompassed is an injection into the chondral or osteochondral defect before or after closure of the defect with a membrane. The membrane can be, but is not limited to, a periosteum or collagen.

In another preferred embodiment, the membrane is a membrane comprising of collagen type I, collagen type III, porcine or rat collagen type I or type III, hyaluronic acid or derivative thereof. An advantage of the closure of the defect before injection of the formulation is to reduce dilution of the formulation or to increase the local concentration of the active ingredient of the formulation. The membrane further acts as bioadhesive agent for the attachment of cells If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e. g., Inject-ease, Genject, injector pens such as Genen, and needleless devices such as MediJector and BioJector. The present pharmaceutical composition can also be adapted for yet to be discovered administration methods. See also Langer, 1990, Science, 249: 1527-1533.

The pharmaceutical composition can also be formulated as a depot preparation. Such long acting formulations may be administered by implantation (for example subcutaneously, into the ligament or tendon, subsynovially or intramuscularly), by subsynovial injection or by intramuscular injection. Thus, for example, the formulations may be modified with suitable polymeric or hydrophobic materials (for example as a emulsion in an acceptable oil) or ion exchange resins, or as sparingly soluble derivatives, for example, as a sparingly soluble salt.

The pharmaceutical compositions may also be in a variety of conventional depot forms employed for administration to provide reactive compositions. These include, for example, solid, semi-solid and liquid dosage forms, such as liquid solutions or suspensions, slurries, gels, creams, balms, emulsions, lotions, powders, sprays, foams, pastes, ointments, salves, balms and drops.

The pharmaceutical compositions may, if desired, be presented in a vial, pack or dispenser device which may contain one or more unit dosage forms containing the active ingredient. In one embodiment, the dispenser device can comprise a syringe having a single dose of the liquid formulation ready for injection. The syringe can be accompanied by instructions for administration.

The pharmaceutical composition may further comprise additional pharmaceutically acceptable components. Other pharmaceutically acceptable carriers, excipients, or stabilizers, such as those described in Remington's Pharmaceutical Sciences 16th edition, Osol, A. Ed. (1980) may also be included in a protein formulation described herein, provided that they do not adversely affect the desired characteristics of the formulation. As used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, asparagine, 2-phenylalanine, and threonine; sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone.

The formulations described herein are useful as pharmaceutical compositions in the treatment and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

Therefore, in another aspect the present invention relates to a pharmaceutical composition comprising as an active ingredient an antibody or fragment or derivative thereof according to the invention. Said pharmaceutical composition may comprise at least one pharmaceutically acceptable carrier or adjuvant or excipient.

Antibodies may be provided in pharmaceutically acceptable compositions as known in the art or as listed in a generally recognized pharmacopeia for use in animals, and more particular in humans.

The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The compositions of the invention can be formulated as neutral or salt forms.

Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The above-mentioned pharmaceutical composition can be used for the treatment or prophylaxis or diagnosis of any disease or disorder, preferably of autoimmune diseases, and most preferably of autoimmune diseases characterized by the production of auto-antibodies.

The dosage amounts and frequencies of administration are encompassed by the terms therapeutically effective and prophylactically effective. The dosage and frequency of administration further will typically vary according to factors specific for each patient depending on the specific therapeutic or prophylactic agents administered, the type of disease, the route of administration, as well as age, body weight, response, and the past medical history of the patient. Suitable regimens can be selected by one skilled in the art. As used herein, the term "therapeutically effective amount" refers to an amount of the therapeutic active component or agent which is sufficient to treat or ameliorate a disease or disorder, to delay the onset of a disease or which provides any therapeutical benefit in the treatment or management of a disease.

For antibodies encompassed by the invention, the dosage administered to a patient is typically 0.0001 mg/kg to 100 mg/kg of the patient's body weight. Preferably the administered dosage is about 15 mg/kg. It is well known that human antibodies have a longer half-life within the human body than antibodies from other species. Therefore, the dosage and frequency of administration of antibodies of the invention or fragments or derivatives thereof may be reduced as compared to normally used dosages of antibodies from other species.

Treatment of a subject with a therapeutically or prophylactically effective amount of antibodies or fragment or derivative thereof of the invention can include a single treatment or, preferably, can include a series of treatments. In a preferred embodiment, a subject can be treated with antibodies or fragments or derivatives thereof of the invention in the range of between about 0.1 to 30 mg/kg body weight, one time per week for between about 1 to 10 weeks, preferably between 2 to 8 weeks, more preferably between about 3 to 7 weeks. The most advantageous form and manner of application can be chosen to best benefit the patient to be treated.

Methods of administering an antibody or fragment or derivative thereof of the present invention include, but are not limited to, parenteral administration (e.g., intradermal, intramuscular, intraperitoneal, intravenous and subcutaneous), epidural, and mucosal (e.g., intranasal and oral routes). In a specific embodiment, the antibodies of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent.

As used herein, the term "treating" and "treatment" refers to administering to a subject a therapeutically effective amount of a pharmaceutical composition according to the invention. A "therapeutically effective amount" refers to an amount of the pharmaceutical composition or the antibody which is sufficient to treat or ameliorate a disease or disorder, to delay the onset of a disease or to provide any therapeutical benefit in the treatment or management of a disease.

As used herein, the term "prophylaxis" refers to the use of an agent for the prevention of the onset of a disease or disorder. A "prophylacticly effective amount" defines an amount of the active component or pharmaceutical agent sufficient to prevent the onset or recurrence of a disease.

As used herein, the terms "disorder" and "disease" are used interchangeably to refer to a condition in a subject. In particular, the term "cancer" is used interchangeably with the term "tumor".

Moreover, antibodies of the invention can be used for diagnostic purposes to detect, diagnose, or monitor diseases, or disorders, in particular cancer and cancer-related diseases. Antibodies or fragments or derivatives thereof according to the invention can be used to assay CD73 levels in a biological sample using classical immunohistological methods as described herein or as known to those of skill in the art (e.g., see Jalkanen et al., 1985, J. Cell. Biol. 101: 976-985; Jalkanen et al., 1987, J. Cell. Biol. 105: 3087-3096). Other antibody-based methods useful for detecting protein gene expression include immunoassays, such as the enzyme linked immunosorbent assay (ELISA) and the radio-immunoassay (RIA).

Therefore, the present invention further relates to a diagnostic composition comprising an antibody of the invention.

As used herein, the term "diagnostic" refers to any use of the inventive antibody for diagnosing the presence of a membrane-bound form of CD73 in a cancer or related disease.

Those "in need of treatment" include those already with the disorder, as well as those in which the disorder is to be prevented. The term "disorder" is any condition that would benefit from treatment with the protein formulation described herein. This includes chronic and acute disorders or diseases including those pathological conditions that predispose the mammal to the disorder in question. Non-limiting examples of disorders to be treated herein include degenerative diseases, bone and/or cartilage and/or articular cartilage defect, an immunological disease preferably chronic inflammation of a joint, bone or cartilage tissue such as arthritis (including but not limited to osteoarthritis, rheumatoid arthritis) and a spinal disorder such as degenerative disc disease. In a preferred embodiment the spinal disorder is idiopathic low back pain, disc herniation, internal disc disruption or fissured discs, radiculopathy, spinal stenosis, herniated nucleus pulposus-induced sciatica, sciatica, idiopathic scoliosis or myelopathy.

It is also contemplated that the antibody or antigen binding portion thereof of the present invention is applied together with a medicament suitable for the treatment of cancer. "Together with" means that the antibody or antigen binding portion thereof is administered prior to the second medicament, at the same time or after the second medicament. A medicament suitable for the treatment of cancer is one or more chemotherapeutic agents, preferably said chemotherapeutic agent is doxorubicin.

In a further embodiment of the invention, there are provided articles of manufacture and kits containing antibody or antigen binding portion thereofs which can be used, for instance, for the therapeutic or non-therapeutic applications described above. The article of manufacture comprises a container with a label. Suitable containers include, for example, bottles, vials, and test tubes. The containers may be formed from a variety of materials such as glass or plastic. The container holds a composition which includes an active agent that is effective for therapeutic or non-therapeutic applications, such as described above. The active agent in the composition is the antibody or antigen binding portion thereof. The label on the container indicates that the composition is used for a specific therapy or non-therapeutic application, and may also indicate directions for either in vivo or in vitro use, such as those described above.

The kit of the invention will typically comprise the container described above and one or more other containers comprising materials desirable from a commercial and user standpoint, including buffers, diluents, filters, needles, syringes, and package inserts with instructions for use.

In some aspects, an anti-CD73 antibody of the invention or antigen binding portion thereof is capable of essentially not inhibiting enzymatic activity of a soluble form of CD73 protein, while inhibiting enzymatic activity of a membrane-bound form of CD73.

In some aspects, an anti-CD73 antibody of the invention or antigen binding portion thereof is capable of essentially not inhibiting enzymatic activity of a soluble form of CD73 protein, while binding to a membrane-bound form of CD73 protein and inhibiting enzymatic activity of said membrane-bound form of CD73.

In some aspects, an anti-CD73 antibody of the invention or antigen binding portion thereof is capable of essentially not inhibiting enzymatic activity of a soluble form of CD73 protein, while binding a membrane-bound form of CD73 protein and specifically inhibiting enzymatic activity of said membrane-bound form of CD73.

In some aspects, an anti-CD73 antibody of the invention or antigen binding portion thereof is capable of binding to membrane-bound and soluble forms of CD73 protein, while specifically inhibiting enzymatic activity of said membrane-bound form of CD73.

In some aspects, an anti-CD73 antibody of the invention or antigen binding portion thereof is capable of binding to membrane-bound and soluble forms of CD73 protein, while not essentially inhibiting said soluble form of CD73 protein, while inhibiting enzymatic activity of said membrane-bound form of CD73.

In some aspects, an anti-CD73 antibody of the invention or antigen binding portion thereof is capable of binding to membrane-bound and soluble forms of CD73 protein, while not essentially inhibiting said soluble form of CD73 protein, while specifically inhibiting enzymatic activity of a membrane-bound form of CD73.

In some aspects, an anti-CD73 antibody of the invention or antigen binding portion thereof is capable of specifically inhibits enzymatic activity of a membrane-bound form of CD73.

In some aspects, an anti-CD73 antibody of the invention or antigen binding portion thereof is capable of essentially not inhibiting a soluble form of CD73 protein.

In some aspects, an anti-CD73 antibody of the invention or antigen binding portion thereof is capable of selectively inhibiting enzymatic activity of a membrane-bound form of CD73.

In some aspects, an anti-CD73 antibody of the invention or antigen binding portion thereof is capable of differentiating between a membrane-bound form of CD73 protein and a soluble form of CD73 protein, preferably said differentiating is specific inhibition of enzymatic activity of a membrane-bound form of CD73.

In some aspects, an anti-CD73 antibody or antigen binding portion thereof is capable of exhibiting an inhibitory preference for enzymatic activity of a membrane-bound form of CD73 protein, e.g., as compared to enzymatic activity of a soluble form of CD73 protein.

In some aspects, an anti-CD73 antibody of the invention or antigen binding portion thereof inhibits enzymatic activity EC 3.1.3.5 of CD73 protein.

In some aspects, an anti-CD73 antibody of the invention or antigen binding portion thereof is capable of increasing the release of TNFα (tumour necrosis factor alpha) in mixed lymphocyte reactions.

In some aspects, an anti-CD73 antibody of the invention or antigen binding portion thereof is capable of increasing the release of IFN-γ (interferon gamma).

In some aspects of the invention, a membrane-bound form of CD73 protein is located on a cancer cell or on an extracellular vesicle (EV) derived from said cancer cell.

In some aspects of the invention, a cancer cell is a human cancer cell.

In some aspects of the invention, an antibody of the invention is a monoclonal antibody.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the VH region polypeptide sequence shown in SEQ ID NO: 9, preferably said polypeptide is a VH region polypeptide.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the H-CDR1 polypeptide sequence shown in SEQ ID NO: 10, preferably said polypeptide is a H-CDR1 polypeptide.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the H-CDR2 region polypeptide sequence shown in SEQ ID NO: 11, preferably said polypeptide is a H-CDR2 polypeptide.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the H-CDR3 region polypeptide sequence shown in SEQ ID NO: 12, said polypeptide is a H-CDR3 polypeptide.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the VL region polypeptide sequence shown in SEQ ID NO: 13, preferably said polypeptide is a VL region polypeptide.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the L-CDR1 region polypeptide sequence shown in SEQ ID NO: 14, preferably said polypeptide is a L-CDR1 polypeptide.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the L-CDR2 region polypeptide sequence shown in SEQ ID NO: 15, preferably said polypeptide is a L-CDR2 polypeptide.

In some aspects, an anti-CD73 antibody of the invention or antigen binding portion thereof comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the L-CDR3 region polypeptide sequence shown in SEQ ID NO: 16, preferably said polypeptide is a L-CDR3 polypeptide.

In some aspects, an anti-CD73 antibody of the invention or antigen binding portion thereof comprises heavy chain variable region polypeptide having amino acid F at a position corresponding to the position 31 of SEQ ID NO: 9, which preferably corresponds to Kabat position H31 in SEQ ID NO: 9 using Kabat numbering.

In some aspects, an anti-CD73 antibody of the invention or antigen binding portion thereof comprises a heavy chain variable region polypeptide having amino acid T at a position corresponding to the position 42 of SEQ ID NO: 9, which preferably corresponds to Kabat position H42 in SEQ ID NO: 9 using Kabat numbering.

In some aspects, an anti-CD73 antibody of the invention or antigen binding portion thereof comprises a heavy chain variable region polypeptide having amino acid T at a position corresponding to the position 53 of SEQ ID NO: 9, which preferably corresponds to Kabat position H52A in SEQ ID NO: 9 using Kabat numbering.

In some aspects, an anti-CD73 antibody of the invention or antigen binding portion thereof comprises a heavy chain variable region polypeptide having amino acid R at a position corresponding to the position 61 of SEQ ID NO: 9, which preferably corresponds to Kabat position H60 in SEQ ID NO: 9 using Kabat numbering.

In some aspects, an anti-CD73 antibody of the invention or antigen binding portion thereof comprises a heavy chain variable region polypeptide having amino acid D at a position corresponding to the position 84 of SEQ ID NO: 9, which preferably corresponds to Kabat position H82A in SEQ ID NO: 9 using Kabat numbering.

In some aspects, an anti-CD73 antibody of the invention or antigen binding portion thereof comprises a heavy chain variable region polypeptide having amino acid S at a position corresponding to the position 85 of SEQ ID NO: 9, which preferably corresponds to Kabat position H82B in SEQ ID NO: 9 using Kabat numbering.

In some aspects, an anti-CD73 antibody of the invention or antigen binding portion thereof comprises a heavy chain variable region polypeptide having amino acid L at a position corresponding to the position 86 of SEQ ID NO: 9, which preferably corresponds to Kabat position H82C in SEQ ID NO: 9 using Kabat numbering.

In some aspects, an anti-CD73 antibody of the invention or antigen binding portion thereof comprises a heavy chain variable region polypeptide having amino acid E at a position corresponding to the position 90 of SEQ ID NO: 9, which preferably corresponds to Kabat position H86 in SEQ ID NO: 9 using Kabat numbering.

In some aspects, an anti-CD73 antibody of the invention or antigen binding portion thereof comprises a heavy chain variable region polypeptide having amino acid G at a position corresponding to the position 105 of SEQ ID NO: 9, which preferably corresponds to Kabat position H100A in SEQ ID NO: 9 using Kabat numbering.

In some aspects, an anti-CD73 antibody of the invention or antigen binding portion thereof comprises a heavy chain variable region polypeptide having amino acid Y at a position corresponding to the position 106 of SEQ ID NO: 9, which preferably corresponds to Kabat position H100B in SEQ ID NO: 9 using Kabat numbering.

In some aspects, an anti-CD73 antibody of the invention or antigen binding portion thereof comprises a heavy chain variable region polypeptide having amino acid R at a position corresponding to the position 107 of SEQ ID NO:

9, which preferably corresponds to Kabat position H100C in SEQ ID NO: 9 using Kabat numbering.

In some aspects, an anti-CD73 antibody of the invention or antigen binding portion thereof comprises a heavy chain variable region polypeptide having amino acid G at a position corresponding to the position 108 of SEQ ID NO: 9, which preferably corresponds to Kabat position H100D in SEQ ID NO: 9 using Kabat numbering.

In some aspects, an anti-CD73 antibody of the invention or antigen binding portion thereof comprises a heavy chain variable region polypeptide having amino acid G at a position corresponding to the position 109 of SEQ ID NO: 9, which preferably corresponds to Kabat position H100E in SEQ ID NO: 9 using Kabat numbering.

In some aspects, an anti-CD73 antibody of the invention or antigen binding portion thereof comprises a heavy chain variable region polypeptide having amino acid Y at a position corresponding to the position 110 of SEQ ID NO: 9, which preferably corresponds to Kabat position H100F in SEQ ID NO: 9 using Kabat numbering.

In some aspects, an anti-CD73 antibody of the invention or antigen binding portion thereof comprises a heavy chain variable region polypeptide having amino acid F at a position corresponding to the position 111 of SEQ ID NO: 9, which preferably corresponds to Kabat position H100G in SEQ ID NO: 9 using Kabat numbering.

In some aspects, an anti-CD73 antibody of the invention or antigen binding portion thereof comprises a heavy chain variable region polypeptide having amino acid D at a position corresponding to the position 115 of SEQ ID NO: 9, which preferably corresponds to Kabat position H104 in SEQ ID NO: 9 using Kabat numbering.

In some aspects, an anti-CD73 antibody of the invention or antigen binding portion thereof comprises a heavy chain variable region polypeptide having amino acid F at a position corresponding to the position 31 of SEQ ID NO: 9; amino acid T at a position corresponding to the position 42 of SEQ ID NO: 9; amino acid T at a position corresponding to the position 53 of SEQ ID NO: 9; amino acid R at a position corresponding to the position 61 of SEQ ID NO: 9; amino acid D at a position corresponding to the position 84 of SEQ ID NO: 9; amino acid S at a position corresponding to the position 85 of SEQ ID NO: 9; amino acid L at a position corresponding to the position 86 of SEQ ID NO: 9; amino acid E at a position corresponding to the position 90 of SEQ ID NO: 9; amino acid G at a position corresponding to the position 105 of SEQ ID NO: 9; amino acid Y at a position corresponding to the position 106 of SEQ ID NO: 9; amino acid R at a position corresponding to the position 107 of SEQ ID NO: 9; amino acid G at a position corresponding to the position 108 of SEQ ID NO: 9; amino acid G at a position corresponding to the position 109 of SEQ ID NO: 9; amino acid Y at a position corresponding to the position 110 of SEQ ID NO: 9; amino acid F at a position corresponding to the position 111 of SEQ ID NO: 9; amino acid D at a position corresponding to the position 115 of SEQ ID NO: 9.

In some aspects, an anti-CD73 antibody of the invention or antigen binding portion thereof comprises one or more of the polypeptides as described herein, using the numbering of SEQ ID NO: 9.

In some aspects, an anti-CD73 antibody of the invention or antigen binding portion thereof comprises one or more of the polypeptides as described herein, using Kabat numbering as described herein.

In some aspects, an anti-CD73 antibody of the invention or antigen binding portion thereof comprises one or more of the polypeptides as described herein and one or more or all specific amino acids as described herein (e.g., unusual amino acid residues as described herein).

In some aspects, an anti-CD73 antibody of the invention or antigen binding portion thereof comprises in its heavy chain variable region, H-CDR1, as shown in SEQ ID NOs: 10.

In some aspects, an anti-CD73 antibody of the invention or antigen binding portion thereof comprises in its heavy chain variable region, H-CDR2, as shown in SEQ ID NOs: 11.

In some aspects, an anti-CD73 antibody of the invention or antigen binding portion thereof comprises in its heavy chain variable region, H-CDR3, as shown in SEQ ID NOs: 12.

In some aspects, an anti-CD73 antibody of the invention or antigen binding portion thereof comprises in its heavy chain variable region, H-CDR1 and H-CDR2, as shown in SEQ ID NOs: 10 and 11.

In some aspects, an anti-CD73 antibody of the invention or antigen binding portion thereof comprises in its heavy chain variable region, H-CDR1 and H-CDR3, as shown in SEQ ID NOs: 10 and 12.

In some aspects, an anti-CD73 antibody of the invention or antigen binding portion thereof comprises in its heavy chain variable region, H-CDR2 and H-CDR3, as shown in SEQ ID NOs: 11 and 12.

In some aspects, an anti-CD73 antibody of the invention or antigen binding portion thereof comprises in its heavy chain variable region, H-CDR1, H-CDR2 and H-CDR3 as shown in SEQ ID NOs: 10, 11 and 12.

In some aspects, an anti-CD73 antibody of the invention or antigen binding portion thereof comprises in its light chain variable region, L-CDR1, as shown in SEQ ID NOs: 14.

In some aspects, an anti-CD73 antibody of the invention or antigen binding portion thereof comprises in its light chain variable region, L-CDR2, as shown in SEQ ID NOs: 15.

In some aspects, an anti-CD73 antibody of the invention or antigen binding portion thereof comprises in its light chain variable region, L-CDR3, as shown in SEQ ID NOs: 16.

In some aspects, an anti-CD73 antibody of the invention or antigen binding portion thereof comprises in its light chain variable region, L-CDR1 and L-CDR2 as shown in SEQ ID NOs: 14 and 15.

In some aspects, an anti-CD73 antibody of the invention or antigen binding portion thereof comprises in its light chain variable region, L-CDR1 and L-CDR3 as shown in SEQ ID NOs: 14 and 16.

In some aspects, an anti-CD73 antibody of the invention or antigen binding portion thereof comprises in its light chain variable region, L-CDR2 and L-CDR3 as shown in SEQ ID NOs: 15 and 16.

In some aspects, an anti-CD73 antibody of the invention or antigen binding portion thereof comprises in its light chain variable region, L-CDR1, L-CDR2 and L-CDR3 as shown in SEQ ID NOs: 14, 15 and 16.

In some aspects, an anti-CD73 antibody of the invention or antigen binding portion thereof comprises in its heavy chain variable region, H-CDR1, H-CDR2 and H-CDR3 as shown in SEQ ID NOs: 10, 11 and 12; and in its light chain variable region, L-CDR1, L-CDR2 and L-CDR3 as shown in SEQ ID NOs: 14, 15 and 16.

In some aspects, an anti-CD73 antibody of the invention or antigen binding portion thereof comprises in its heavy chain variable region, VH region sequence as shown in SEQ ID NO: 9.

In some aspects, an anti-CD73 antibody of the invention or antigen binding portion thereof comprises in its light chain variable region, VL region sequence shown in SEQ ID NO: 13.

In some aspects, an anti-CD73 antibody of the invention or antigen binding portion thereof comprises in its heavy chain variable region, VH region sequence as shown in SEQ ID NO: 9 and in its light chain variable region, VL region sequence shown in SEQ ID NO: 13.

In some aspects of the invention, a cancer cell is selected from a group consisting of: a chemotherapy resistant cancer cell; metastatic cancer cell; refractory cancer cell; recurrent cancer cell.

In some aspects of the invention, a cancer cell is derived from a cancer selected from a group consisting of: leukemia, lymphoma, myeloma, breast cancer, colorectal cancer, glioblastoma, ovarian cancer, hematological cancer, epithelial cancer, pancreatic cancer, bladder cancer, uterine/cervical cancer, ovarian cancer, prostate cancer, testicular cancer, esophageal cancer, gastrointestinal cancer, colon cancer, kidney cancer, head and neck cancer, lung cancer, stomach cancer, germ cell cancer, bone cancer, liver cancer, thyroid cancer, skin cancer, neoplasm of the central nervous system, sarcoma, and virus-related cancer.

In some aspects of the invention, a cancer is leukemia and is selected from a group consisting of: Acute myeloid leukemia (AML); Chronic myeloid leukemia (CML); Acute lymphocytic leukemia (ALL); Chronic lymphocytic leukemia (CLL).

In some aspects, an anti-CD73 antibody of the invention or antigen binding portion thereof is chimeric, humanized or human.

In some aspects, an anti-CD73 antibody of the invention or antigen binding portion thereof is coupled to one or more of the following: a labelling group; a toxin; an anti-tumor agent or medicament; an adenosine receptor inhibitor, preferably said adenosine receptor inhibitor is an inhibitor of A2A receptor (e.g., as described in WO2016075176).

In some aspects, an anti-CD73 antibody of the invention is obtainable by a hybridoma.

In some aspects, a hybridoma of the invention produces an anti-CD73 antibody of the invention.

In some aspects, the invention provides a nucleic acid encoding the antibody of the invention or antigen binding portion thereof.

In some aspects of the invention, a nucleic acid is selected from the group consisting of: SEQ ID NO: 1; SEQ ID NO: 2; SEQ ID NO: 3; SEQ ID NO: 4; SEQ ID NO: 5; SEQ ID NO: 6; SEQ ID NO: 7; SEQ ID NO: 8.

In some aspects, the invention provides an expression vector comprising at least one of the nucleic acid molecules of the invention.

In some aspects, the invention provides a bispecific molecule comprising an antibody of the invention or antigen binding portion thereof linked to a molecule having a second binding specificity, wherein said second binding specificity is from binding specificity of said antibody or antigen binding portion thereof.

In some aspects, the invention provides an immunoconjugate comprising an antibody of the invention or antigen binding portion thereof of any one of the preceding items linked to a second agent, wherein said second agent is different from said antibody or antigen binding portion thereof.

In some aspects, the invention provides a host cell comprising a vector and/or nucleic acid of the invention, preferably said host cell is transformed with said vector and/or nucleic acid, further preferably said host cell is a heterologous host cell (e.g., a host cell that is different from the organism from which an antibody or antigen binding portion thereof according to the present invention is derived, e.g., siad host cell is not Rattus norvegicus host cell), further most preferably said host cell is a non-human host cell, further most preferably said host cell is an isolated host cell.

In some aspects, the invention provides an extracellular vesicle (EV) comprising CD73 protein.

In some aspects of the invention, the CD73 protein is a membrane bound form of CD73 protein.

In some aspects, the EV of the invention is capable of converting AMP to adenosine and inorganic phosphate.

In some aspects of the invention, the EV of the invention has EC 3.1.3.5 enzymatic activity.

In some aspects of the invention, the EV of the invention is derived from a cancer cell.

In some aspects of the invention a membrane-bound form of CD73 is a human membrane-bound form of CD73.

In some aspects of the invention a membrane-bound form of CD73 is a human membrane-bound form of CD73, wherein said human CD73 is selected from the group consisting of: SEQ ID NO: 17 and SEQ ID NO: 18.

In some aspects, the invention provides a composition comprising the antibody or antigen binding portion thereof, hybridoma, nucleic acid, expression vector, bispecific molecule, immunoconjugate, host cell or extracellular vesicle (EV) according to the invention.

In some aspects of the invention, the composition is a pharmaceutical or diagnostic composition.

In some aspects, a pharmaceutical composition of the invention comprises: i) an antibody of the invention or antigen binding portion thereof, hybridoma, nucleic acid, expression vector, bispecific molecule, immunoconjugate, host cell or extracellular vesicle (EV) according to the invention; ii) one or more chemotherapeutic agents, preferably said chemotherapeutic agent is doxorubicin; and iii) optionally, pharmaceutically acceptable carrier, excipient and/or diluent.

In some aspects, the invention provides a method for production of the antibody of the invention or antigen binding portion thereof, comprising culturing the host cell of the invention under conditions allowing synthesis of said antibody or antigen binding portion thereof and recovering said antibody or antigen binding portion thereof from said culture.

In some aspects, the invention provides a method for immunizing a non-human animal, said method comprising the following steps: i) providing ex vivo or in vitro cancer cells, preferably said cancer cells are cultured human glioblastoma cells, further preferably said cultured human glioblastoma cells are GBM20 human glioblastoma cells; ii) separating extracellular vesicles (EVs) from said cancer cells, preferably said separation comprises centrifugation (e.g., ultracentrifugation); and iii) immunizing said non-human animal with said extracellular vesicles (EVs).

In some aspects of the invention, a method for immunizing a non-human animal according to the invention is the method for immunizing a non-human animal against a membrane-bound form of CD73, wherein extracellular vesicles (EVs) comprise said membrane-bound form of CD73.

In some aspects, the invention provides a method for preparation of an antibody, comprising: i) immunizing a non-human mammal with extracellular vesicles (EVs) derived from a cancer cell; ii) isolating an antibody obtained in step (i).

In some aspects of the invention, the extracellular vesicles (EVs) comprise a membrane-bound form of CD73.

In some aspects, the invention provides a method for preparation of the antibody of the invention, comprising: i) immunizing a non-human mammal with extracellular vesicles (EVs) derived from cancer cells as described herein; ii) isolating an antibody obtained in step (i); and iii) determining whether the antibody obtained in step (ii) exhibits one or more of the properties according to present invention.

In some aspects, the invention provides a method for preparation of a hybridoma, said method comprising: i) immunizing a non-human animal by the immunizing method as defined in any one of preceding items; ii) collecting antibody producing cells from the immunized non-human animal to fuse them with myeloma cells and produce hybridoma cells; and iii) optionally, characterizing hybridoma cells, preferably said characterization comprises immunoprecipitation and/or mass-spectroscopical analysis of said hybridoma cells.

In some aspects, the invention provides a method of decreasing adenosine levels in a cancer cell expressing CD73, comprising contacting the cell with the antibody, antigen binding portion thereof, bispecific molecule or immunoconjugate according to the invention, such that adenosine levels are decreased (e.g., as described in WO2016081748).

In some aspects, the invention provides a method of stimulating a T cell response against a cancer cell expressing CD73 in a subject in need thereof, comprising administering an effective amount of an antibody, or antigen binding portion thereof, bispecific molecule or immunoconjugate according to invention, such that a T cell response is stimulated against the cancer cell (e.g., as described in WO2016081748).

In some aspects, the invention provides a method of stimulating an immune response in a subject comprising administering the antibody, or antigen binding portion thereof, bispecific molecule or immunoconjugate according to invention to the subject, such that an immune response in the subject is stimulated (e.g., as described in WO2016081748).

In some aspects of the invention the subject has a cancer cell expressing CD73 and an immune response against the tumor cell is stimulated (e.g., as described in WO2016081748).

In some aspects, the invention provides a method for inhibiting the growth of cancer cells expressing CD73 in a subject comprising administering to the subject the antibody, or antigen binding portion thereof, bispecific molecule or immunoconjugate according to invention, such that growth of the tumor is inhibited in the subject (e.g., as described in WO2016081748).

In some aspects, the invention provides a method of treating cancer comprising administering to a subject in need thereof a therapeutically effective amount of the antibody, or antigen binding portion thereof, bispecific molecule or immunoconjugate, according to the invention, to treat the cancer (e.g., as described in WO2016081748).

In some aspects of the invention, an antibody is a monoclonal or polyclonal antibody.

In some aspects of the invention, the membrane-bound form of CD73 is a human membrane-bound form of CD73.

In some aspects of the invention, the method of the invention is an in vitro, ex vivo or in vivo method or combination thereof.

In some aspects, the invention provides a kit comprising the antibody of the invention or antigen binding portion thereof, hybridoma, nucleic acid, expression vector, bispecific molecule, immunoconjugate, host cell, composition or extracellular vesicle (EV) according to the invention; and optionally, instructions for use of said kit.

In some aspects, the invention provides an antibody of the invention or antigen binding portion thereof, hybridoma, nucleic acid, expression vector, bispecific molecule, immunoconjugate, host cell, composition or extracellular vesicle (EV) according to the invention, for use in one or more of the following methods: method for treatment, amelioration, prophylaxis or diagnostics of cancer; method for treatment, amelioration, prophylaxis or diagnostics of cancer, wherein said cancer is resistant to chemotherapy and/or metastatic cancer and/or refractory cancer and/or recurrent cancer; method for monitoring development of cancer and/or for assessing the efficacy of cancer therapy (e.g., as described in WO2004079013); method for screening a candidate compound for anti-cancer activity (e.g., as described in WO2004079013); method for altering resistance of cancer cells to chemotherapy; method for sensitizing cancer cells to chemotherapy; method for induction of apoptosis in cancer cells; method for altering immunosuppressive capacity of a cancer; method for decreasing adenosine levels in a cancer cell expressing CD73; method for stimulating a T cell response against a cancer cell expressing CD73; method for stimulating an immune response in a subject; method for inhibiting the growth of cancer cell expressing CD73; method for detecting the presence of human CD73 in a sample; method for production or preparation of an antibody; method for immunizing a non-human animal; method for preparation of a hybridoma; any method according to the present invention.

In some aspects, the invention provides an antibody of the invention or antigen binding portion thereof, hybridoma, nucleic acid, expression vector, bispecific molecule, immunoconjugate, host cell, composition or extracellular vesicle (EV) according to the invention, for use method for treatment, amelioration, prophylaxis or diagnostics of cancer, wherein said cancer is selected from a group consisting of: leukemia, lymphoma, myeloma, breast cancer, colorectal cancer, glioblastoma, ovarian cancer, hematological cancer, epithelial cancer, pancreatic cancer, preferably said leukemia is selected from a group consisting of: Acute myeloid leukemia (AML); Chronic myeloid leukemia (CML); Acute lymphocytic leukemia (ALL); Chronic lymphocytic leukemia (CLL).

In some aspects, the invention provides use of the antibody of the invention or antigen binding portion thereof, hybridoma, nucleic acid, expression vector, bispecific molecule, immunoconjugate, host cell, composition or extracellular vesicle (EV) according to the invention for one or more of the following: for treatment, amelioration, prophylaxis or diagnostics of cancer; for treatment, amelioration, prophylaxis or diagnostics of cancer, wherein said cancer is resistant to chemotherapy and/or metastatic cancer and/or refractory cancer and/or recurrent cancer; for monitoring development of cancer and/or for assessing the efficacy of cancer therapy; for screening a candidate compound for anti-cancer activity; for altering resistance of cancer cells to chemotherapy; for sensitizing cancer cells to chemotherapy; for induction of apoptosis in cancer cells; for altering immunosuppressive capacity of a cancer; for decreasing adenosine levels in a cancer cell expressing CD73; for stimulating a T cell response against a cancer cell expressing CD73; for stimulating an immune response in a subject; for inhibiting the growth of cancer cell expressing CD73; for detecting the presence of human CD73 in a sample; for production or preparation of an antibody; for immunizing a non-human animal; for preparation of a hybridoma; in the method according to the present invention.

In some aspects of the invention, the use according to the invention is an in vitro, ex vivo or in vivo use or combination thereof.

The invention is also characterized by the following items:

1. An anti-CD73 antibody or antigen binding portion thereof, wherein said anti-CD73 antibody or antigen binding portion thereof exhibits one or more of the following properties:
   i) does not essentially inhibit enzymatic activity of a soluble form of CD73 protein, wherein inhibits enzymatic activity of a membrane-bound form of CD73;
   ii) does not essentially inhibit enzymatic activity of a soluble form of CD73 protein, wherein binds to a membrane-bound form of CD73 protein and inhibits enzymatic activity of said membrane-bound form of CD73;
   iii) does not essentially inhibit enzymatic activity of a soluble form of CD73 protein, wherein binds a membrane-bound form of CD73 protein and specifically inhibits enzymatic activity of said membrane-bound form of CD73;
   iv) binds to membrane-bound and soluble forms of CD73 protein, wherein specifically inhibits enzymatic activity of said membrane-bound form of CD73;
   v) binds to membrane-bound and soluble forms of CD73 protein, wherein does not essentially inhibit said soluble form of CD73 protein, wherein inhibits enzymatic activity of said membrane-bound form of CD73;
   vi) binds to membrane-bound and soluble forms of CD73 protein, wherein does not essentially inhibit said soluble form of CD73 protein, wherein specifically inhibits enzymatic activity of said membrane-bound form of CD73;
   vii) specifically inhibits enzymatic activity of a membrane-bound form of CD73;
   viii) does not essentially inhibit a soluble form of CD73 protein;
   ix) selectively inhibits enzymatic activity of a membrane-bound form of CD73;
   x) differentiates between a membrane-bound form of CD73 protein and a soluble form of CD73 protein;
   xi) has an inhibitory preference for enzymatic activity of a membrane-bound form of CD73 protein compared to enzymatic activity of a soluble form of CD73 protein.
2. The antibody or antigen binding portion thereof according to any one of preceding items, wherein said enzymatic activity is EC 3.1.3.5.
3. The antibody or antigen binding portion thereof according to any one of the preceding claims, wherein said antibody or antigen binding portion thereof increases the release of TNFα (tumor necrosis factor alpha) in mixed lymphocyte reactions.
4. The antibody or antigen binding portion thereof according to any one of preceding items, wherein said membrane-bound form of CD73 protein is located on a cancer cell or on an extracellular vesicle (EV) derived from said cancer cell.
5. The antibody or antigen binding portion thereof according to any one of preceding items, wherein said cancer cell is a human cancer cell.
6. The antibody or antigen binding portion thereof according to any one of preceding items, wherein said antibody is a monoclonal antibody.
7. The antibody or antigen binding portion thereof according to any one of preceding items, which comprises one or more of the following polypeptides:
   i) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the VH region polypeptide sequence shown in SEQ ID NO: 9, preferably said polypeptide is a VH region polypeptide;
   ii) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the H-CDR1 polypeptide sequence shown in SEQ ID NO: 10, preferably said polypeptide is a H-CDR1 polypeptide;
   iii) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the H-CDR2 region polypeptide sequence shown in SEQ ID NO: 11, preferably said polypeptide is a H-CDR2 polypeptide;
   iv) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the H-CDR3 region polypeptide sequence shown in SEQ ID NO: 12, said polypeptide is a H-CDR3 polypeptide;
   v) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the VL region polypeptide sequence shown in SEQ ID NO: 13, preferably said polypeptide is a VL region polypeptide;
   vi) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the L-CDR1 region polypeptide sequence shown in SEQ ID NO: 14, preferably said polypeptide is a L-CDR1 polypeptide;
   vii) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the L-CDR2 region polypeptide sequence shown in SEQ ID NO: 15, preferably said polypeptide is a L-CDR2 polypeptide;
   viii) a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to the L-CDR3 region polypeptide sequence shown in SEQ ID NO: 16, preferably said polypeptide is a L-CDR3 polypeptide;
ix) heavy chain variable region polypeptide having amino acid F at a position corresponding to the position 31 of SEQ ID NO: 9, which preferably corresponds to Kabat position H31 in SEQ ID NO: 9 using Kabat numbering;
x) a heavy chain variable region polypeptide having amino acid T at a position corresponding to the position 42 of SEQ ID NO: 9, which preferably corresponds to Kabat position H42 in SEQ ID NO: 9 using Kabat numbering;
xi) a heavy chain variable region polypeptide having amino acid T at a position corresponding to the position 53 of SEQ ID NO: 9, which preferably corresponds to Kabat position H52A in SEQ ID NO: 9 using Kabat numbering;
xii) a heavy chain variable region polypeptide having amino acid R at a position corresponding to the position 61 of SEQ ID NO: 9, which preferably corresponds to Kabat position H60 in SEQ ID NO: 9 using Kabat numbering;
xiii) a heavy chain variable region polypeptide having amino acid D at a position corresponding to the position 84 of SEQ ID NO: 9, which preferably corresponds to Kabat position H82A in SEQ ID NO: 9 using Kabat numbering;
xiv) a heavy chain variable region polypeptide having amino acid S at a position corresponding to the position 85 of SEQ ID NO: 9, which preferably corresponds to Kabat position H82B in SEQ ID NO: 9 using Kabat numbering;
xv) a heavy chain variable region polypeptide having amino acid L at a position corresponding to the position 86 of SEQ ID NO: 9, which preferably corresponds to Kabat position H82C in SEQ ID NO: 9 using Kabat numbering;
xvi) a heavy chain variable region polypeptide having amino acid E at a position corresponding to the position 90 of SEQ ID NO: 9, which preferably corresponds to Kabat position H86 in SEQ ID NO: 9 using Kabat numbering;
xvii) a heavy chain variable region polypeptide having amino acid G at a position corresponding to the position 105 of SEQ ID NO: 9, which preferably corresponds to Kabat position H100A in SEQ ID NO: 9 using Kabat numbering;
xviii) a heavy chain variable region polypeptide having amino acid Y at a position corresponding to the position 106 of SEQ ID NO: 9, which preferably corresponds to Kabat position H100B in SEQ ID NO: 9 using Kabat numbering;
xix) a heavy chain variable region polypeptide having amino acid R at a position corresponding to the position 107 of SEQ ID NO: 9, which preferably corresponds to Kabat position H100C in SEQ ID NO: 9 using Kabat numbering;
xx) a heavy chain variable region polypeptide having amino acid G at a position corresponding to the position 108 of SEQ ID NO: 9, which preferably corresponds to Kabat position H100D in SEQ ID NO: 9 using Kabat numbering;
xxi) a heavy chain variable region polypeptide having amino acid G at a position corresponding to the position 109 of SEQ ID NO: 9, which preferably corresponds to Kabat position H100E in SEQ ID NO: 9 using Kabat numbering;
xxii) a heavy chain variable region polypeptide having amino acid Y at a position corresponding to the position 110 of SEQ ID NO: 9, which preferably corresponds to Kabat position H100F in SEQ ID NO: 9 using Kabat numbering;
xxiii) a heavy chain variable region polypeptide having amino acid F at a position corresponding to the position 111 of SEQ ID NO: 9, which preferably corresponds to Kabat position H100G in SEQ ID NO: 9 using Kabat numbering;
xxiv) a heavy chain variable region polypeptide having amino acid D at a position corresponding to the position 115 of SEQ ID NO: 9, which preferably corresponds to Kabat position H104 in SEQ ID NO: 9 using Kabat numbering;
xxv) a heavy chain variable region polypeptide having amino acid F at a position corresponding to the position 31 of SEQ ID NO: 9; amino acid T at a position corresponding to the position 42 of SEQ ID NO: 9; amino acid T at a position corresponding to the position 53 of SEQ ID NO: 9; amino acid R at a position corresponding to the position 61 of SEQ ID NO: 9; amino acid D at a position corresponding to the position 84 of SEQ ID NO: 9; amino acid S at a position corresponding to the position 85 of SEQ ID NO: 9; amino acid L at a position corresponding to the position 86 of SEQ ID NO: 9; amino acid E at a position corresponding to the position 90 of SEQ ID NO: 9; amino acid G at a position corresponding to the position 105 of SEQ ID NO: 9; amino acid Y at a position corresponding to the position 106 of SEQ ID NO: 9; amino acid R at a position corresponding to the position 107 of SEQ ID NO: 9; amino acid G at a position corresponding to the position 108 of SEQ ID NO: 9; amino acid G at a position corresponding to the position 109 of SEQ ID NO: 9; amino acid Y at a position corresponding to the position 110 of SEQ ID NO: 9; amino acid F at a position corresponding to the position 111 of SEQ ID NO: 9; amino acid D at a position corresponding to the position 115 of SEQ ID NO: 9;
xxvi) a heavy chain variable region polypeptide having amino acids as defined in xxv) above, using the numbering of SEQ ID NO: 9;
xxvii) a heavy chain variable region polypeptide having amino acids as defined in xxv) above, using Kabat numbering defined in ix)-xxiv) above;
xxviii) a polypeptide as defined in i), further comprising in its heavy chain variable region amino acids as defined in xxv);
xxix) a polypeptide as defined in ii), further comprising in its heavy chain variable region amino acids as defined in xxv);
xxx) a polypeptide as defined in iii), further comprising in its heavy chain variable region amino acids as defined in xxv);
xxxi) a polypeptide as defined in iv), further comprising in its heavy chain variable region amino acids as defined in xxv).

8. The antibody or antigen binding portion thereof according to any one of preceding items, wherein said antibody or antigen binding portion thereof comprises one or more of the following:
i) in its heavy chain variable region, H-CDR1, as shown in SEQ ID NOs: 10;
ii) in its heavy chain variable region, H-CDR2, as shown in SEQ ID NOs: 11;

iii) in its heavy chain variable region, H-CDR3, as shown in SEQ ID NOs: 12;
iv) in its heavy chain variable region, H-CDR1 and H-CDR2, as shown in SEQ ID NOs: 10 and 11;
v) in its heavy chain variable region, H-CDR1 and H-CDR3, as shown in SEQ ID NOs: 10 and 12;
vi) in its heavy chain variable region, H-CDR2 and H-CDR3, as shown in SEQ ID NOs: 11 and 12;
vii) in its heavy chain variable region, H-CDR1, H-CDR2 and H-CDR3 as shown in SEQ ID NOs: 10, 11 and 12;
viii) in its light chain variable region, L-CDR1, as shown in SEQ ID NOs: 14;
ix) in its light chain variable region, L-CDR2, as shown in SEQ ID NOs: 15;
x) in its light chain variable region, L-CDR3, as shown in SEQ ID NOs: 16;
xi) in its light chain variable region, L-CDR1 and L-CDR2 as shown in SEQ ID NOs: 14 and 15;
xii) in its light chain variable region, L-CDR1 and L-CDR3 as shown in SEQ ID NOs: 14 and 16;
xiii) in its light chain variable region, L-CDR2 and L-CDR3 as shown in SEQ ID NOs: 15 and 16;
xiv) in its light chain variable region, L-CDR1, L-CDR2 and L-CDR3 as shown in SEQ ID NOs: 14, 15 and 16;
xv) in its heavy chain variable region, H-CDR1, H-CDR2 and H-CDR3 as shown in SEQ ID NOs: 10, 11 and 12; and in its light chain variable region, L-CDR1, L-CDR2 and L-CDR3 as shown in SEQ ID NOs: 14, 15 and 16;
xvi) in its heavy chain variable region, VH region sequence as shown in SEQ ID NO: 9;
xvii) in its light chain variable region, VL region sequence shown in SEQ ID NO: 13;
xviii) in its heavy chain variable region, VH region sequence as shown in SEQ ID NO: 9 and in its light chain variable region, VL region sequence shown in SEQ ID NO: 13.

9. The antibody or antigen binding portion thereof of any one of the preceding items, wherein said cancer cell is selected from a group consisting of:
i) a chemotherapy resistant cancer cell;
ii) metastatic cancer cell;
iii) refractory cancer cell;
iv) recurrent cancer cell;

10. The antibody or antigen binding portion thereof of any one of the preceding items, wherein said cancer cell is derived from a cancer selected from a group consisting of: leukemia, lymphoma, myeloma, breast cancer, colorectal cancer, glioblastoma, ovarian cancer, hematological cancer, epithelial cancer, pancreatic cancer, bladder cancer, uterine/cervical cancer, ovarian cancer, prostate cancer, testicular cancer, esophageal cancer, gastrointestinal cancer, colon cancer, kidney cancer, head and neck cancer, lung cancer, stomach cancer, germ cell cancer, bone cancer, liver cancer, thyroid cancer, skin cancer, neoplasm of the central nervous system, sarcoma, and virus-related cancer.

11. The antibody or antigen binding portion thereof of any one of the preceding items, wherein said cancer is leukemia and is selected from a group consisting of: Acute myeloid leukemia (AML); Chronic myeloid leukemia (CML); Acute lymphocytic leukemia (ALL); Chronic lymphocytic leukemia (CLL).

12. The antibody or antigen binding portion thereof of any one of the preceding items, wherein said antibody or antigen binding portion thereof is chimeric, humanized or human.

13. The antibody or antigen binding portion thereof of any one of the preceding items, wherein said antibody or antigen binding portion thereof is coupled to one or more of the following:
i) a labelling group;
ii) a toxin;
iii) an anti-tumor agent or medicament;
iv) an adenosine receptor inhibitor, preferably said adenosine receptor inhibitor is an inhibitor of A2A receptor;

14. The antibody according to any one of preceding items, wherein said antibody is obtainable by a hybridoma.

15. A hybridoma, wherein said hybridoma produces the monoclonal antibody according to any one of preceding items.

16. A nucleic acid encoding the antibody or antigen binding portion thereof according to any one of preceding items, 17. The nucleic acid encoding the antibody or antigen binding portion thereof according to any one of preceding items, wherein said nucleic acid is selected from the group consisting of:
i) SEQ ID NO: 1;
ii) SEQ ID NO: 2;
iii) SEQ ID NO: 3;
iv) SEQ ID NO: 4;
v) SEQ ID NO: 5;
vi) SEQ ID NO: 6;
vii) SEQ ID NO: 7;
viii) SEQ ID NO: 8.

18. An expression vector comprising at least one of the nucleic acid molecules according to any one of preceding items.

19. A bispecific molecule comprising the antibody or antigen binding portion thereof of any one of the preceding items linked to a molecule having a second binding specificity, wherein said second binding specificity is from binding specificity of said antibody or antigen binding portion thereof.

20. An immunoconjugate comprising the antibody or antigen binding portion thereof of any one of the preceding items linked to a second agent, wherein said second agent is different from said antibody or antigen binding portion thereof.

21. A host cell comprising a vector and/or nucleic acid according to any one of the preceding claims, preferably said host cell is transformed with said vector and/or nucleic acid, further preferably said host cell is a heterologous host cell, further most preferably said host cell is a non-human host cell.

22. An extracellular vesicle (EV) comprising CD73 protein.

23. The extracellular vesicle (EV) according to any one of preceding items, wherein said CD73 protein is a membrane bound form of CD73 protein.

24. The extracellular vesicle (EV) according to any one of preceding items, wherein said EV is capable of converting AMP to adenosine and inorganic phosphate.

25. The extracellular vesicle (EV) according to any one of preceding items, wherein said EV has EC 3.1.3.5 enzymatic activity.

26. The extracellular vesicle (EV) according to any one of preceding items, wherein said EV is derived from a cancer cell.

27. The antibody or antigen binding portion thereof, hybridoma, nucleic acid, expression vector, bispecific molecule, immunoconjugate, host cell, composition or extracellular vesicle (EV) according to any one of preceding items, wherein said membrane-bound form of CD73 is a human membrane-bound form of CD73.
28. The antibody or antigen binding portion thereof, hybridoma, nucleic acid, expression vector, bispecific molecule, immunoconjugate, host cell, composition or extracellular vesicle (EV) according to any one of preceding items, wherein said membrane-bound form of CD73 is a human membrane-bound form of CD73, wherein said human CD73 is selected from the group consisting of:
   i) SEQ ID NO: 17; and
   ii) SEQ ID NO: 18.
29. A composition comprising the antibody or antigen binding portion thereof, hybridoma, nucleic acid, expression vector, bispecific molecule, immunoconjugate, host cell or extracellular vesicle (EV) according to any one of preceding items.
30. The composition according to any one of preceding items, wherein said composition is a pharmaceutical or diagnostic composition.
31. The pharmaceutical composition according to any one of preceding items comprising:
   i) antibody or antigen binding portion thereof, hybridoma, nucleic acid, expression vector, bispecific molecule, immunoconjugate, host cell or extracellular vesicle (EV) according to any one of preceding items;
   ii) one or more chemotherapeutic agents, preferably said chemotherapeutic agent is doxorubicin;
   iii) optionally, pharmaceutically acceptable carrier, excipient and/or diluent.
32. A method for production of the antibody or antigen binding portion thereof according to any one of preceding items, comprising culturing the host cell according to any one of preceding items under conditions allowing synthesis of said antibody or antigen binding portion thereof and recovering said antibody or antigen binding portion thereof from said culture.
33. A method for immunizing a non-human animal, said method comprising the following steps:
   i) providing ex vivo or in vitro cancer cells, preferably said cancer cells are cultured human glioblastoma cells, further preferably said cultured human glioblastoma cells are GBM20 human glioblastoma cells;
   ii) separating extracellular vesicles (EVs) from said cancer cells, preferably said separation comprises centrifugation;
   iii) immunizing said non-human animal with said extracellular vesicles (EVs).
34. The method for immunizing a non-human animal according to any one of the preceding items, for immunizing a non-human animal against a membrane-bound form of CD73, wherein extracellular vesicles (EVs) comprise said membrane-bound form of CD73.
35. A method for preparation of an antibody, comprising:
   i) immunizing a non-human mammal with extracellular vesicles (EVs) derived from a cancer cell;
   ii) isolating an antibody obtained in step (i).
36. The method for preparation of the antibody according to any one of preceding items, wherein said extracellular vesicles (EVs) comprise a membrane-bound form of CD73.
37. The method for preparation of the antibody according to any one of preceding items, comprising:
   i) immunizing a non-human mammal with extracellular vesicles (EVs) derived from cancer cells as defined in any one of preceding items;
   ii) isolating an antibody obtained in step (i); and
   iii) determining whether the antibody obtained in step (ii) exhibits one or more of the properties according to item 1.
38. A method for preparation of a hybridoma, said method comprising:
   i) immunizing a non-human animal by the immunizing method as defined in any one of preceding items;
   ii) collecting antibody producing cells from the immunized non-human animal to fuse them with myeloma cells and produce hybridoma cells;
   iii) optionally, characterizing hybridoma cells, preferably said characterization comprises immunoprecipitation and/or mass-spectroscopical analysis of said hybridoma cells.
39. A method of decreasing adenosine levels in a cancer cell expressing CD73, comprising contacting the cell with the antibody, antigen binding portion thereof, bispecific molecule or immunoconjugate according to any one of preceding items, such that adenosine levels are decreased.
40. A method of stimulating a T cell response against a cancer cell expressing CD73 in a subject in need thereof, comprising administering an effective amount of an antibody, or antigen binding portion thereof, bispecific molecule or immunoconjugate according to any one of preceding items, such that a T cell response is stimulated against the cancer cell.
41. A method of stimulating an immune response in a subject comprising administering the antibody, or antigen binding portion thereof, bispecific molecule or immunoconjugate according to any one of preceding items to the subject, such that an immune response in the subject is stimulated.
42. The method according to any one of preceding items, wherein the subject has a cancer cell expressing CD73 and an immune response against the tumor cell is stimulated.
43. A method for inhibiting the growth of cancer cells expressing CD73 in a subject comprising administering to the subject the antibody, or antigen binding portion thereof, bispecific molecule or immunoconjugate according to any one of preceding items, such that growth of the tumor is inhibited in the subject.
44. A method of treating cancer comprising administering to a subject in need thereof a therapeutically effective amount of the antibody, or antigen binding portion thereof, bispecific molecule or immunoconjugate, according to any one of preceding items, to treat the cancer.
45. The method according to any one of preceding items, wherein said antibody is a monoclonal or polyclonal antibody.
46. The method according to any one of preceding items, wherein said membrane-bound form of CD73 is a human membrane-bound form of CD73.
47. The method according to any one of preceding items, wherein said membrane-bound form of CD73 is a human membrane-bound form of CD73, wherein said human CD73 is selected from the group consisting of:
   i) SEQ ID NO: 17; and
   ii) SEQ ID NO: 18
48. The method according to any one of preceding items, wherein said method is an in vitro, ex vivo or in vivo method or combinations thereof.
49. A kit comprising the antibody or antigen binding portion thereof, hybridoma, nucleic acid, expression vector, bispecific molecule, immunoconjugate, host cell, composition or extracellular vesicle (EV) according to any one of preceding items; and optionally, instructions for use of said kit.

50. The antibody or antigen binding portion thereof, hybridoma, nucleic acid, expression vector, bispecific molecule, immunoconjugate, host cell, composition or extracellular vesicle (EV) according to any one of preceding items, for use as a medicament.

51. The antibody or antigen binding portion thereof, hybridoma, nucleic acid, expression vector, bispecific molecule, immunoconjugate, host cell, composition or extracellular vesicle (EV) according to any one of preceding items, for use in one or more of the following methods:
   i) method for treatment, amelioration, prophylaxis or diagnostics of cancer;
   ii) method for treatment, amelioration, prophylaxis or diagnostics of cancer, wherein said cancer is resistant to chemotherapy and/or metastatic cancer and/or refractory cancer and/or recurrent cancer;
   iii) method for monitoring development of cancer and/or for assessing the efficacy of cancer therapy;
   iv) method for screening a candidate compound for anti-cancer activity;
   v) method for altering resistance of cancer cells to chemotherapy;
   vi) method for sensitizing cancer cells to chemotherapy;
   vii) method for induction of apoptosis in cancer cells;
   viii) method for altering immunosuppressive capacity of a cancer;
   ix) method for decreasing adenosine levels in a cancer cell expressing CD73;
   x) method for stimulating a T cell response against a cancer cell expressing CD73;
   xi) method for stimulating an immune response in a subject;
   xii) method for inhibiting the growth of cancer cell expressing CD73;
   xiii) method for detecting the presence of human CD73 in a sample;
   xiv) method for production or preparation of an antibody;
   xv) method for immunizing a non-human animal;
   xvi) method for preparation of a hybridoma;
   xvii) method according to any one of preceding items.

52. The antibody or antigen binding portion thereof, hybridoma, nucleic acid, expression vector, bispecific molecule, immunoconjugate, host cell, composition or extracellular vesicle (EV) according to any one of preceding items, wherein said cancer is selected from a group consisting of: leukemia, lymphoma, myeloma, breast cancer, colorectal cancer, glioblastoma, ovarian cancer, hematological cancer, epithelial cancer, pancreatic cancer, preferably said leukemia is selected from a group consisting of: Acute myeloid leukemia (AML); Chronic myeloid leukemia (CML); Acute lymphocytic leukemia (ALL); Chronic lymphocytic leukemia (CLL).

53. Use of the antibody or antigen binding portion thereof, hybridoma, nucleic acid, expression vector, bispecific molecule, immunoconjugate, host cell, composition or extracellular vesicle (EV) according to any one of preceding items for one or more of the following:
   i) for treatment, amelioration, prophylaxis or diagnostics of cancer;
   ii) for treatment, amelioration, prophylaxis or diagnostics of cancer, wherein said cancer is resistant to chemotherapy and/or metastatic cancer and/or refractory cancer and/or recurrent cancer;
   iii) for monitoring development of cancer and/or for assessing the efficacy of cancer therapy;
   iv) for screening a candidate compound for anti-cancer activity;
   v) for altering resistance of cancer cells to chemotherapy;
   vi) for sensitizing cancer cells to chemotherapy;
   vii) for induction of apoptosis in cancer cells;
   viii) for altering immunosuppressive capacity of a cancer;
   ix) for decreasing adenosine levels in a cancer cell expressing CD73;
   x) for stimulating a T cell response against a cancer cell expressing CD73;
   xi) for stimulating an immune response in a subject;
   xii) for inhibiting the growth of cancer cell expressing CD73;
   xiii) for detecting the presence of human CD73 in a sample;
   xiv) for production or preparation of an antibody;
   xv) for immunizing a non-human animal;
   xvi) for preparation of a hybridoma;
   xvii) in the method according to any one of preceding items.

54. The use according to any one of preceding items, wherein said cancer selected from a group consisting of: leukemia, lymphoma, myeloma, breast cancer, colorectal cancer, glioblastoma, ovarian cancer, hematological cancer, epithelial cancer, pancreatic cancer, preferably said leukemia is selected from a group consisting of: Acute myeloid leukemia (AML); Chronic myeloid leukemia (CML); Acute lymphocytic leukemia (ALL); Chronic lymphocytic leukemia (CLL).

55. The use according to any one of preceding items, wherein said use is an in vitro, ex vivo or in vivo use or combinations thereof.

EXAMPLES OF THE INVENTION

Figure 2:
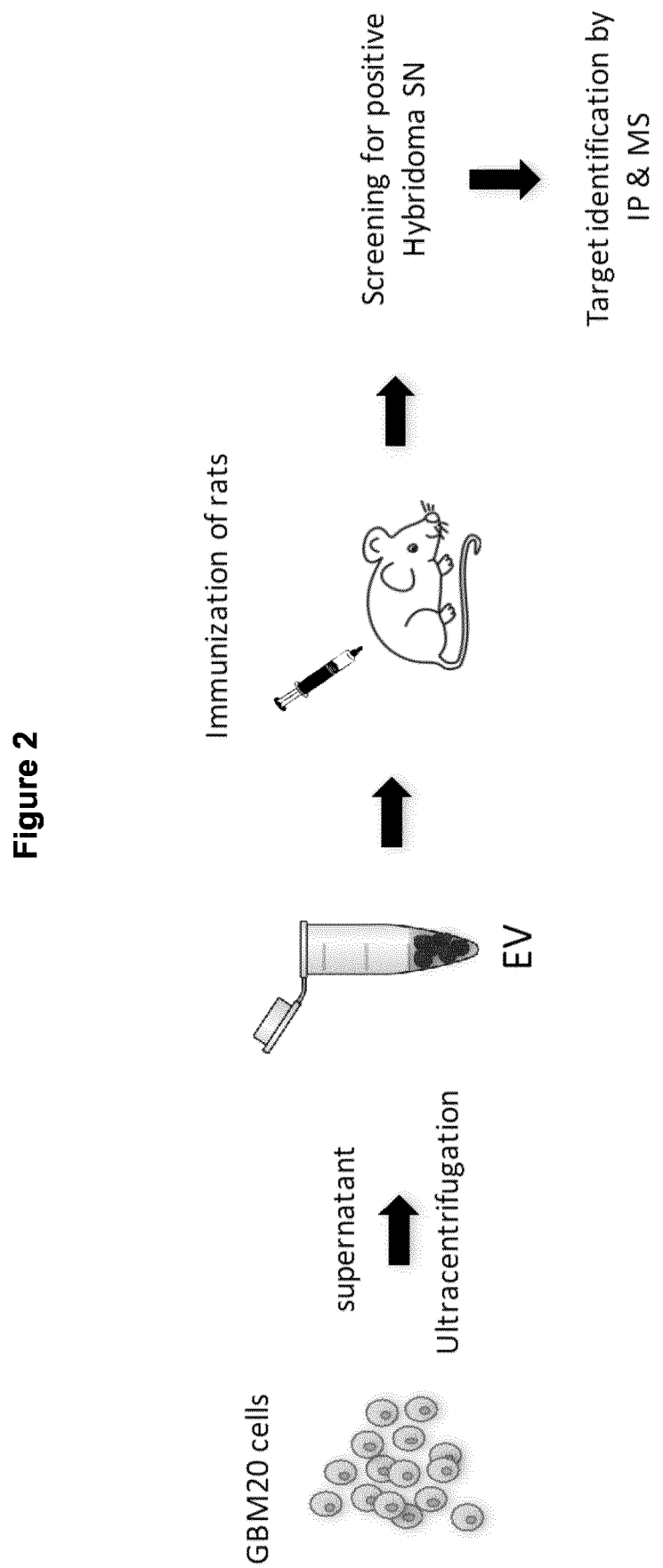
FIG. 2: Principle of the EV-based immunization strategy for the generation of functional mAbs targeting membrane proteins on the surface of cancer cells. GBM20 is a human glioblastoma cell line; SN=supernatant; IP=immunoprecipitation; MS=mass spectrometry.

Example 1: Preparation of Functional mAbs Targeting Membrane Proteins on the Surface of Cancer Cells In this example, mAb 22E6 was prepared by immunizing rats with extracellular vesicles (EVs) derived from the glioblastoma cell line GBM20 (FIG. 2). The extracellular vesicles (EVs) were derived from the GBM20 cell line by ultracentrifugation, isolated from the supernatant and injected into the rat using standard immunization technique known in the art. Hybridoma cell lines derived from rat spleen cells were produced and screened for antibodies that binds to a membrane-bound form of CD73 protein and specifically inhibits enzymatic activity of said membrane-bound form of CD73. Target mAb identification was carried out by immunoprecipitation in combination with mass spectrometry (IP-MS) and the mAb 22E6 was identified accordingly.

Example 2: Characterization Binding Affinity and Specificity of the mAb 22E6

Figure 3:
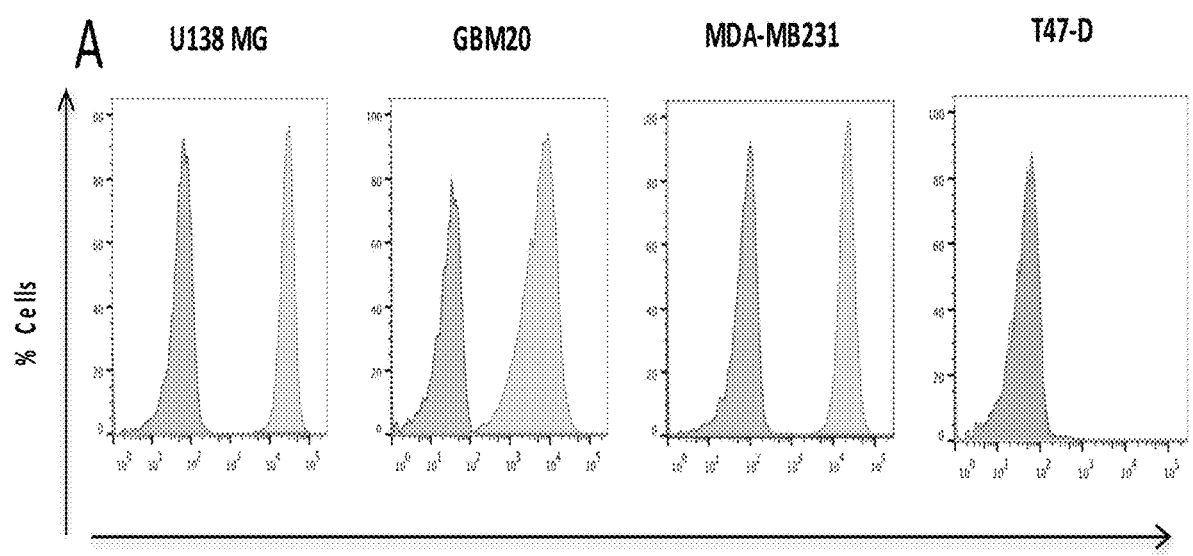
FIG. 3: mAb 22E6 recognizes CD73 on cancer cells. (A) Flow cytometry with 22E6 and an anti-rat-IgG-specific, fluorophore-labeled secondary mAb revealed that the protein recognized by the mAb is present on the surface of human cancer cells. Shown are 4 representative cell lines of a total of approx. 30 tested cell lines. U138 MG and GBM20 are glioblastoma cell lines, MDA-MB231 and T47D are human breast cancer cell lines. (B) Immunoblot with the same cell line, using a commercial CD73 mAb. (C) Immunoprecipitation of CD73 protein from lysates of U138 glioblastoma cells with 22E6 or an isotype mAb, followed by an immunoblot with a commercial CD73 mAb demonstrated the specificity of 22E6. Input=U138 lysate.
Figure 3:
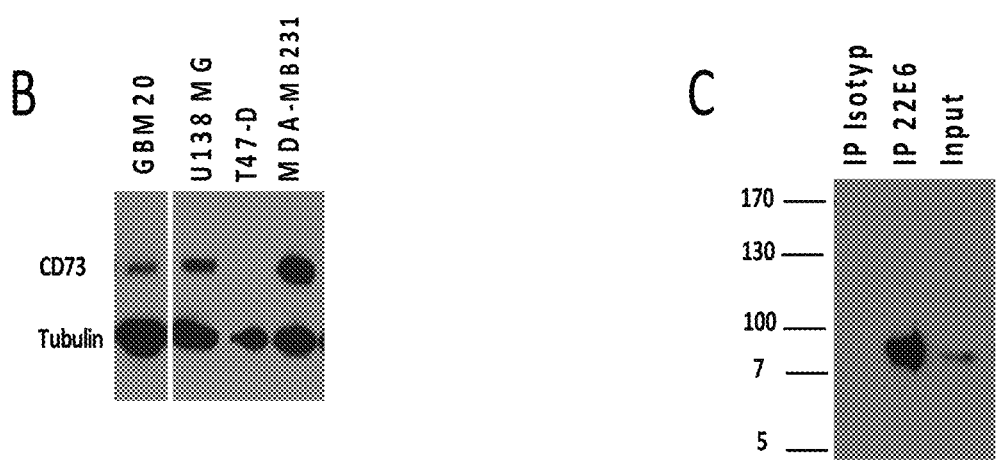

In this example, mAb 22E6 binding affinity was characterized (FIG. 3). It was shown that mAb 22E6 recognizes CD73 protein on cancer cells. Using a special flow cytometry technique, a fluorescence-activated cell sorting (FACS) with 22E6 and an anti-rat-IgG-specific, fluorophore-labeled secondary mAb, it was shown that the protein recognized by the 22E6 mAb of the invention is present on the surface of human cancer cells of a total of approx. 30 tested cell lines. 4 representative cell lines of said 30 tested cell lines are shown in FIG. 3A herein. U138 MG and GBM20 are glioblastoma cell lines, MDA-MB231 and T47D are human breast cancer cell lines. In order to compare the specificity of mAb 22E6 with the specificity of a commercial CD73 mAb an immunoblot with the same cell lines (U138 MG, GBM20, MDA-MB231 and T47D) was performed using the commercial CD73 mAb as shown in FIG. 3B. An immunoprecipitation of the CD73 protein from lysates of U138 glioblastoma cells with either 22E6 or an isotype mAb, followed by an immunoblot with the commercial CD73 mAb demonstrated the specificity of 22E6 of the invention as shown in FIG. 3C.

Example 3: Characterization of Inhibitory Properties of the mAb 22E6

Figure 4:
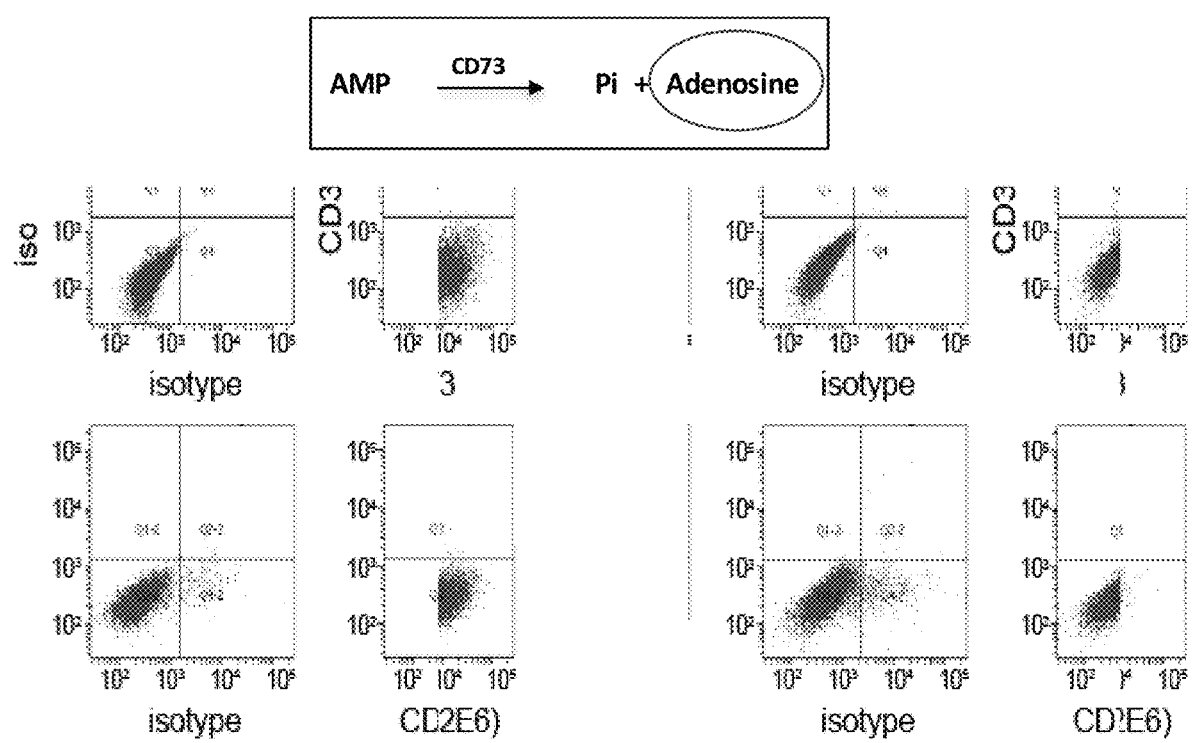
FIG. 4: 22E6 blocks adenosine production. CD73-positive human A375 melanoma cells were incubate with AMP for 60 min and the concentration of AMP (left) and ADO (right) in the supernatant were measured. APCP is a small-molecule specific CD73 inhibitor.
Figure 5:
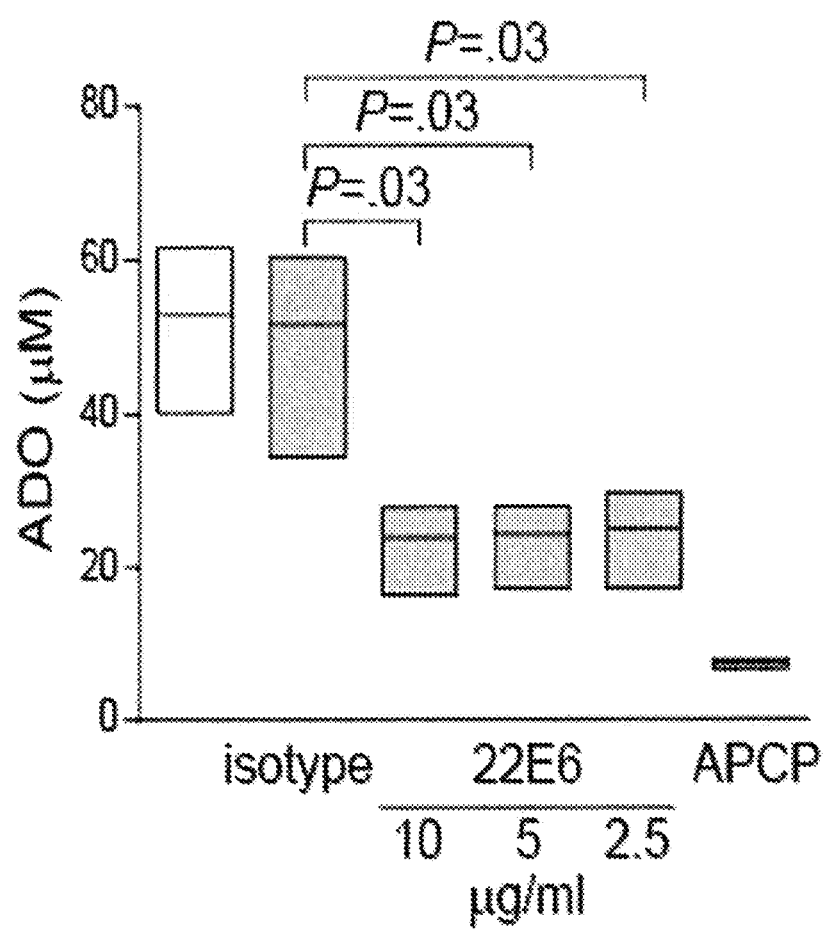
FIG. 5: 22E6 inhibits ADO generation by human CLL cells. APCP is a CD73 small molecule inhibitor.

In this example, mAb 22E6 inhibitory properties were characterized and it was shown that 22E6 blocks adenosine production (FIG. 4). Accordingly, as shown in FIG. 4 herein, CD73-positive human A375 melanoma cells were incubated with AMP (adenosine monophosphate) for 60 min and the concentration of AMP (left) and ADO (adenosine, right) in the supernatant were measured. Additionally, it was shown that 22E6 mAb inhibits ADO generation by human CLL cells (FIG. 5). Adenosine 5'-(α,β-methylene)diphosphate (APCP) is a small-molecule specific CD73 inhibitor.

Example 4: Characterization of Immunoregulatory Properties of the mAb 22E6

Figure 6:
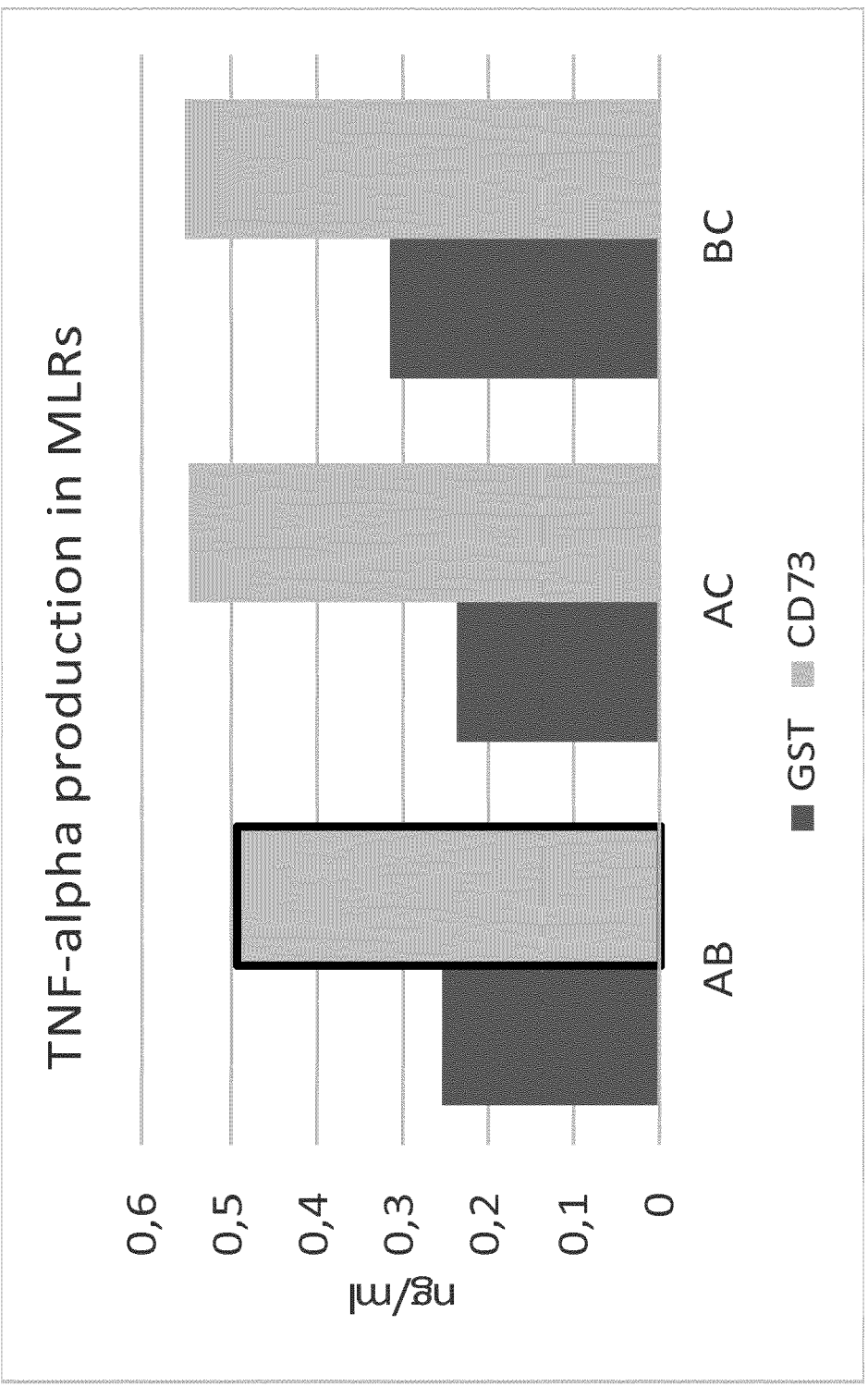
FIG. 6: 22E6 increases the release of TNFα in mixed lymphocyte reactions. 5×105 peripheral blood mononuclear cells each from two out of three different donors (A, B, C) were co-incubated in standard cell culture medium at 37° for 24 h with 22E6 (50 µg/ml) or a GSF-mAb (50 µg/ml) and the amount of TNFα was measured with a commercial ELISA assay.

In this example, mAb 22E6 immunoregulatory properties were characterized and it was shown that 22E6 increases the release of TNFα in mixed lymphocyte reactions (MLRs) (FIG. 6). Accordingly, 5×10$^5$ peripheral blood mononuclear cells (PBMCs) each from two out of three different donors (A, B, C) were co-incubated in standard cell culture medium at 37° for 24 h with 22E6 (50 µg/ml) or a GSF-mAb (50 µg/ml) and the amount of TNFα was measured with a commercial ELISA assay.

Example 5: Isolation and Characterization of Extracellular Vesicles (EVs)

Figure 7:
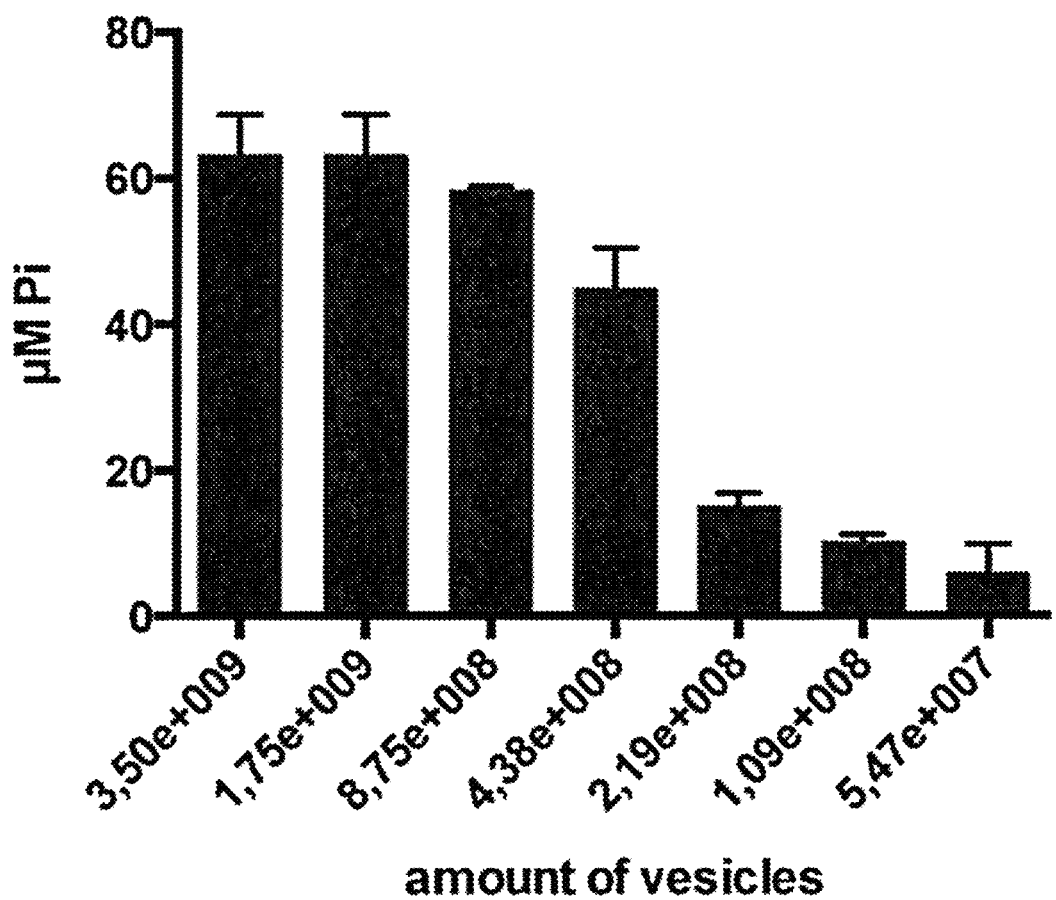
FIG. 7: EVs from CD73+ cancer cells convert AMP to adenosine and inorganic phosphate (µM Pi).
Figure 8:
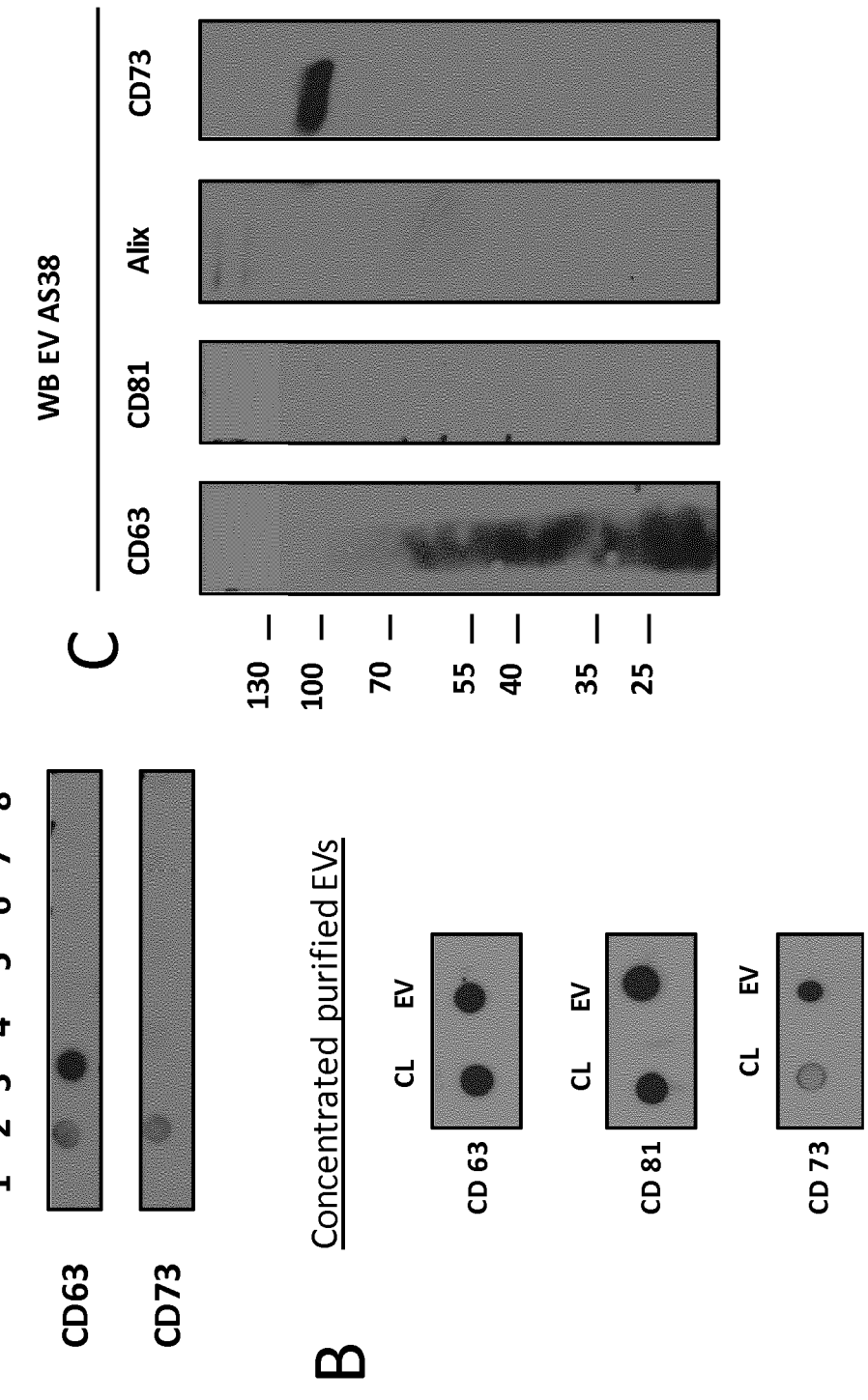
FIG. 8: EVs isolated from the ascites of a patient with ovarian cancer carry CD73.

In this example, extracellular vesicles (EVs) were isolated and characterized. It was shown that the EVs can convert AMP to adenosine and inorganic phosphate (FIG. 7) and that EVs isolated from the ascites of a patient with ovarian cancer carry CD73 (FIG. 8). As shown in FIG. 7 herein, EVs from CD73+ cancer cells convert AMP to adenosine and inorganic phosphate (µM Pi). As shown in FIG. 8 herein, CD73 is present on EVs purified by density gradient (FIG. 8A), EVs can be further concentrated without loss of CD73 signal (FIG. 8B) and CD73 on EVs can be detected by a standard Western Blotting (WB) technique (FIG. 8C).

Example 6: Characterization of the ADO Production Inhibition by the mAb 22E6

Figure 9:
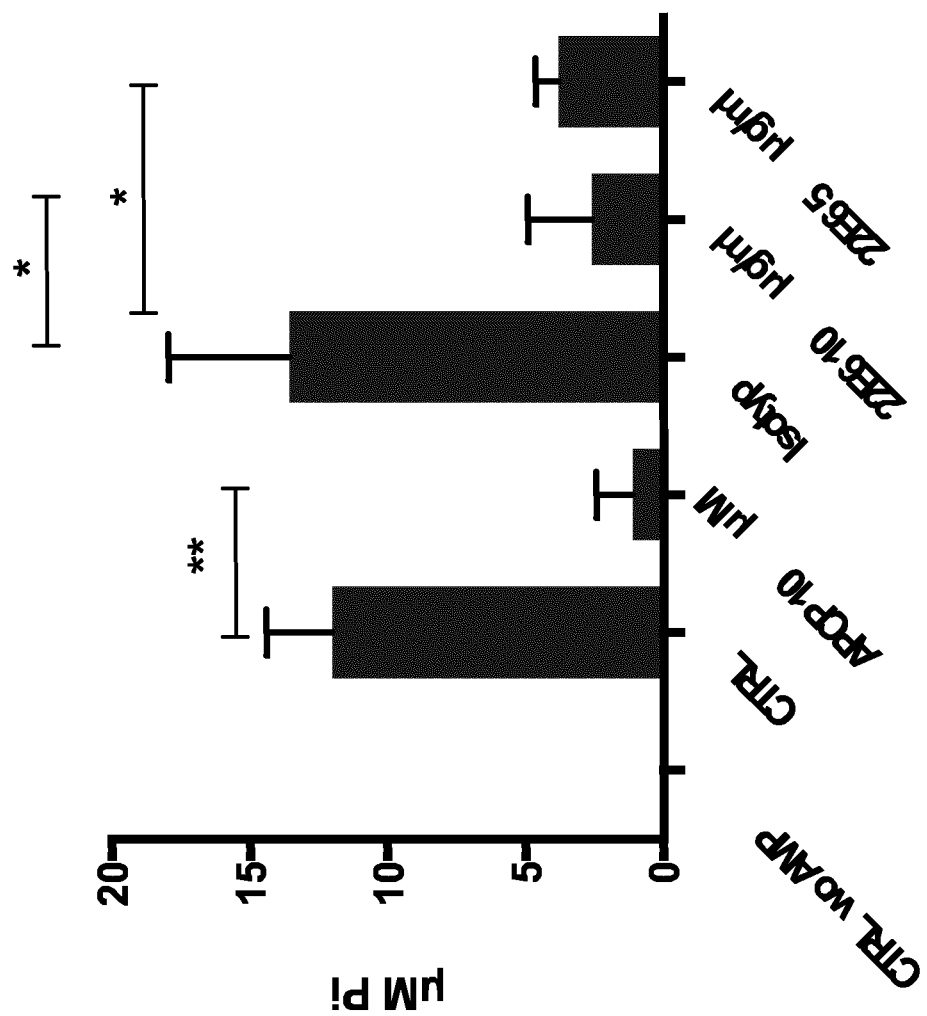
FIG. 9: 22E6 blocks ADO production by EVs from malignant ascites. EVs were incubated in phosphate-free buffer in the presence of 1 mM AMP with APCP, 22E6 or an isotype mAb for 60 min and the concentration of inorganic phosphate (Pi; produced alongside the dephosphorylation of AMP) was quantified with a malachite green assay.

In this example, the ADO production inhibition by the mAb 22E6 was characterized and it was shown that 22E6 blocks ADO production by EVs derived from malignant ascites (FIG. 9). Accordingly, EVs were incubated in phosphate-free buffer in the presence of 1 mM AMP with APCP, 22E6 or an isotype mAb for 60 min and the concentration of inorganic phosphate (Pi; produced alongside the dephosphorylation of AMP) was quantified with a standard malachite green assay. Based on the above it was concluded that 22E6 inhibits CD73 on cancer derived EVs.

Example 7: Characterization the Inhibitory Preference of the mAb 22E6

Figure 10:
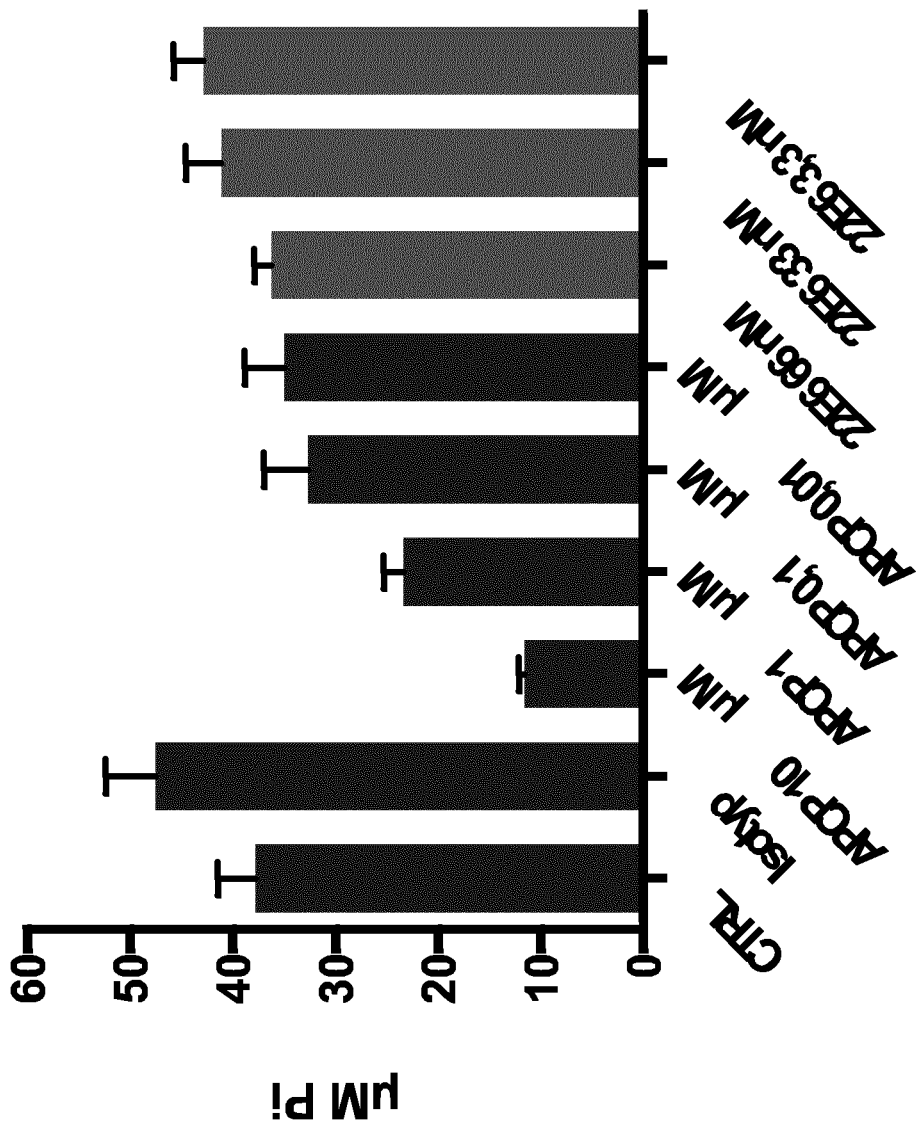
FIG. 10: Inhibitory preference exhibited by 22E6.

In this example, the inhibitory preference of the mAb 22E6 was characterized and it was shown that the mAb 22E6 has an inhibitory preference for enzymatic activity of a membrane-bound form of CD73 protein compared to enzymatic activity of a soluble form of CD73 protein (FIG. 10). As shown in FIG. 10, 22E6 has no or essentially no effect on the enzyme activity of soluble CD73 protein.

Example 8: Sequencing Analysis of the Immunoglobulin Sequences of the mAb 22E6

Figure 13:
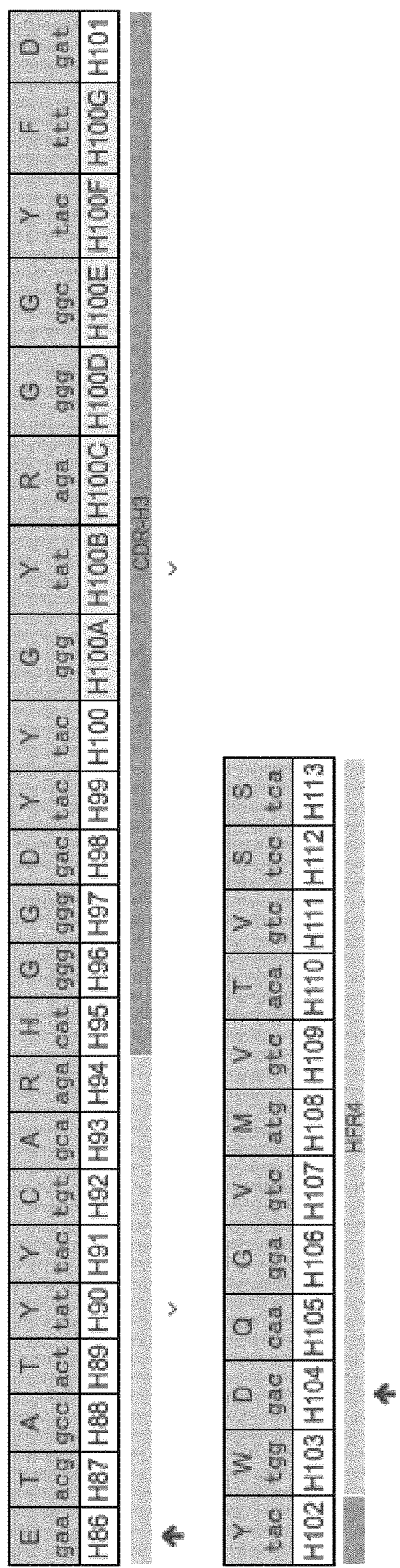
FIG. 13: Numbering of amino acids in the heavy chain (SEQ ID NO: 9) and unusual amino acid residues therein.

In this example, immunoglobulin sequences encoding the heavy and light chains of 22E6 were successfully amplified and cloned (FIGS. 11 and 12). Accordingly, it was shown that immunoglobulin sequences of the mAb 22E6 clearly differ from those of the known CD73 antibodies, the difference is especially pronounced in the CDR regions (FIGS. 13 and 14). Accordingly, the following unique sequences were identified within mAb 22E6: SEQ ID NO: 1, which is the DNA sequence encoding VH region; SEQ ID NO: 2, which is the DNA sequence encoding the VH complementary determining region 1 (H-CDR1); SEQ ID NO: 3, which is the DNA sequence encoding the VH complementary determining region 2 (H-CDR2); SEQ ID NO: 4, which is the DNA sequence encoding the VH complementary determining region 3 (H-CDR3); SEQ ID NO: 5, which is the DNA sequence encoding VL region; SEQ ID NO: 6, which is the DNA sequence encoding the VL complementary determining region 1 (L-CDR1); SEQ ID NO: 7, which is the DNA sequence encoding the VH complementary determining region 2 (L-CDR2); SEQ ID NO: 8, which is the DNA sequence encoding the VH complementary determining region 3 (L-CDR3); SEQ ID NO: 9, which is the amino acid sequence of the VH region; SEQ ID NO: 10, which is the amino acid sequence of the VH complementary determining region 1 (H-CDR1); SEQ ID NO: 11, which is the amino acid sequence of the VH complementary determining region 2 (H-CDR2); SEQ ID NO: 12, which is the amino acid sequence of the VH complementary determining region 3 (H-CDR3); SEQ ID NO: 13, which is the amino acid sequence of the VL region; SEQ ID NO: 14, which is the amino acid sequence of the VL complementary determining region 1 (L-CDR1); SEQ ID NO: 15, which is the amino acid sequence of the VL complementary determining region 2 (L-CDR2); SEQ ID NO: 16, which is the amino acid sequence of the VL complementary determining region 3 (L-CDR3).

Further, sequence analysis identified several unusual amino acid residues (i.e., present in <1% of sequences) in said unique sequences within mAb 22E6 (FIGS. 13 and 14). These were the following:

amino acid F at the position 31 of SEQ ID NO: 9, which corresponds to Kabat position H31 in SEQ ID NO: 9 using Kabat numbering;

amino acid T at the position 42 of SEQ ID NO: 9, which corresponds to Kabat position H42 in SEQ ID NO: 9 using Kabat numbering;

amino acid T at the position 53 of SEQ ID NO: 9, which corresponds to Kabat position H52A (insertion) in SEQ ID NO: 9 using Kabat numbering;

amino acid R at the position 61 of SEQ ID NO: 9, which corresponds to Kabat position H60 in SEQ ID NO: 9 using Kabat numbering;

amino acid D at the position 84 of SEQ ID NO: 9, which corresponds to Kabat position H82A (insertion) in SEQ ID NO: 9 using Kabat numbering;

amino acid S at the position 85 of SEQ ID NO: 9, which corresponds to Kabat position H82B (insertion) in SEQ ID NO: 9 using Kabat numbering;

amino acid L at the position 86 of SEQ ID NO: 9, which corresponds to Kabat position H82C (insertion) in SEQ ID NO: 9 using Kabat numbering;

amino acid E at the position 90 of SEQ ID NO: 9, which corresponds to Kabat position H86 in SEQ ID NO: 9 using Kabat numbering;

amino acid G at the position 105 of SEQ ID NO: 9, which corresponds to Kabat position H100A (insertion) in SEQ ID NO: 9 using Kabat numbering;

amino acid Y at the position 106 of SEQ ID NO: 9, which corresponds to Kabat position H100B (insertion) in SEQ ID NO: 9 using Kabat numbering;

amino acid R at the position 107 of SEQ ID NO: 9, which corresponds to Kabat position H100C (insertion) in SEQ ID NO: 9 using Kabat numbering;

amino acid G at the position 108 of SEQ ID NO: 9, which corresponds to Kabat position H100D (insertion) in SEQ ID NO: 9 using Kabat numbering;

amino acid G at the position 109 of SEQ ID NO: 9, which corresponds to Kabat position H100E (insertion) in SEQ ID NO: 9 using Kabat numbering;

amino acid Y at the position 110 of SEQ ID NO: 9, which corresponds to Kabat position H100F (insertion) in SEQ ID NO: 9 using Kabat numbering;

amino acid F at the position 111 of SEQ ID NO: 9, which corresponds to Kabat position H100G (insertion) in SEQ ID NO: 9 using Kabat numbering;

amino acid D at the position 115 of SEQ ID NO: 9, which corresponds to Kabat position H104 in SEQ ID NO: 9 using Kabat numbering.

Example 9: IFN-γ Release Induced by mAB 22E6

Figure 15:
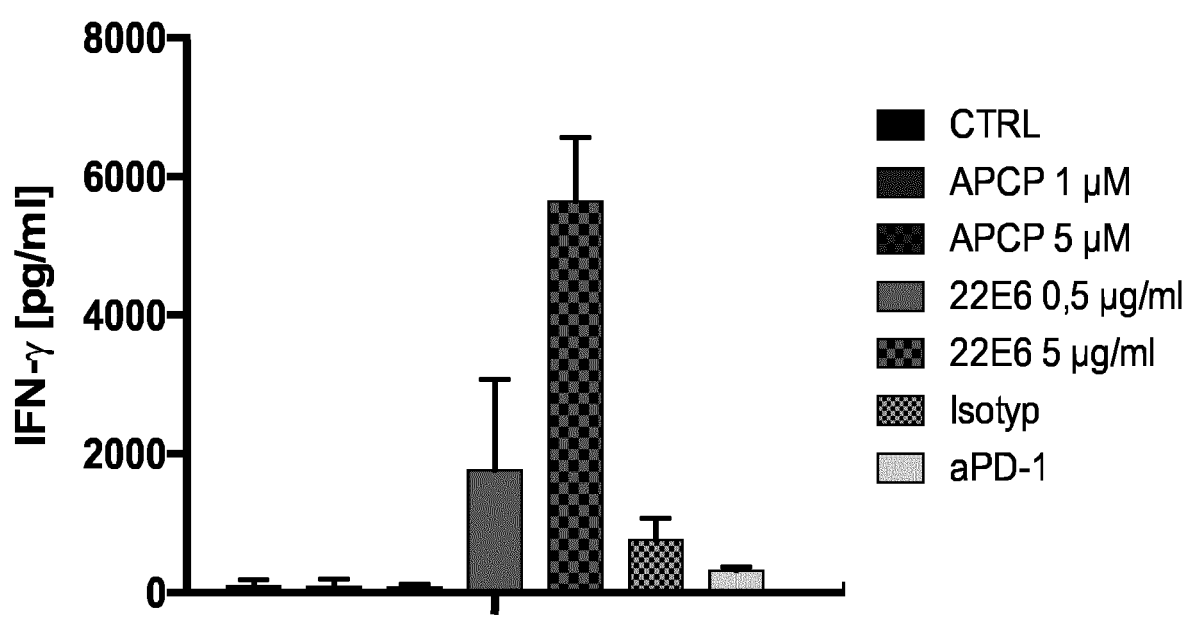
FIG. 15: Massive release of interferon-gamma (IFN-γ) being induced by mAB 22E6 in comparison to an isotyp antibody. IFN-γ being a marker for the activation of cytotoxic T-cells. Peripheral blood mononuclear cells (PBMCs) from two different donors were incubated separately as indicated at 37° C. for 24 h. Interferon-gamma (IFN-γ) in the supernatant was then quantified by a standard ELISA assay.

In this example, mAb 22E6 increases massive release of IFN-γ (FIG. 15). Peripheral blood mononuclear cells (PBMCs) from two different donors were incubated separately in standard cell culture medium at 37° for 24 h with 22E6 (0.5 µg/ml and 5 µg/ml), APCP (1 µM and 5 µM), isotyp antibody (5 µg/ml), aPD-1 (5 µg/ml) and control (5 µg/ml). The amount of interferon-gamma (IFN-γ) in the supernatant was then measured with a commercial ELISA assay.

REFERENCES

Antonioli, L., Blandizzi, C., Pacher, P., and Hask6, G. (2013). Immunity, inflammation and cancer: a leading role for adenosine. Nat Rev Cancer 13, 842-857.

Cushman, S. M., Jiang, C., Hatch, A. J., Shterev, I., Sibley, A. B., Niedzwiecki, D., Venook, A. P., Owzar, K., Hutwitz, H. I., and Nixon, A. B. (201 5). Gene expression markers of efficacy and resistance to cetuximab treatment in metastatic colorectal cancer: results from CALGB 80203 (Alliance). Clin Cancer Res 21, 1078-1086.

Deaglio, S., Dwyer, K. M., Gao, W., Friedman, D., Usheva, A., Erat, A., Chen, J. F., Enjyoji, K., Linden, J., Oukka, M., Kuchroo, V. K, Strom, T. B., and Robson, S. C. (2007). Adenosine generation catalyzed by CD39 and CD73 expressed on regulatory T cells mediates immune suppression. J Exp Med 204, 1257-1265.

Jin, D., Fan, J., Wang, L., Thompson, L. F., Liu, A., Daniel, B. J., Shin, T., Curiel, T. J., and Zhang, B. (2010). CD73 on tumor cells impairs antitumor T-cell responses: a novel mechanism of tumorinduced immune suppression. Cancer Res 70, 2245-2255.

Loi, S., Pommey, S., Haibe-Kains, B., Beavis, P. A., Darcy, P. K., Smyth, M. J., and Stagg, J. (2013). CD73 promotes anthracycline resistance and poor prognosis in triple negative breast cancer. Proc Natl Acad Sci USA 110, 11091-11096.

Martinez, R. J., Zhang, N., Thomas, S. R., Nandiwada, S. L., Jenkins, M. K., Binstadt, B. A., and Mueller, D. L. (2012). Arthritogenic self-reactive CD4+ T cells acquire an FR4hiCD73hi anergic state in the presence of Foxp3+ regulatory T cells. J Immunol 188, 170-181.

Mikhailov, A., Sokolavskaya, A., Yegutkin, G. G., Amdahl, H., West, A., Yagita, H., Lahesmaa, R., Thompson, L. F., Jalkanen, S., Blokhin, D., and Eriksson, J. E. (2008). CD73 participates in cellular multiresistance program and protects against TRAIL-induced apoptosis. J Immunol 181, 464-475.

Quezada, C., Garrido, W., Oyarzlin, C., Fernandez, K., Segura, R., Melo, R., Casanallo, P., Sobrevia, L., and San Martin, R. (2013). 5'-ectonucleotidase mediates multiple-drug resistance in glioblastoma multiforme cells. J Cell Physiol 228, 602-608.

Ren, Z. H., Lin, C. Z., Cao, W., Yang, R., Lu, W., Liu, Z. Q., Chen, Y. M., Yang, X., Tian, Z., Wang, L. Z., Li, J., Wang, X., Chen, W. T., Ji, T., and Zhang, C. P. (2016). CD73 is associated with poor prognosis in HNSCC. Oncotarget 7, 61690-61 702.

Stagg, J., Divisekera, U., McLaughlin, N., Sharkey, J., Pommey, S., Denoyer, D., Dwyer, K. M., and Smyth, M. J. (2910). Anti-CD73 antibody therapy inhibits breast tumor growth and metastasis. Proc Natl Acad Sci USA 107, 1547-1552.

Stagg, J., Beavis, P. A., Divisekera, U., Liu, M. C., Moller, A., Darcy, P. K., and Smyth, M. J. (2012). CD73-deficient mice are resistant to carcinogenesis. Cancer Res 72, 2190-2196.

Wang, L., Fan, J., Thompson, L. F., Zhang, Y., Shin, T., Curiel, T. J., and Zhang, B. (2011). CD73 has distinct roles in nonhematopoietic and hematopoietic cells to promote tumor growth in mice. J Clin Invest 121, 2371-2382.

Zhang, B. (2010). CD73: a novel target for cancer immunotherapy. Cancer Res 70, 6407-6411.

The invention claimed is:

1. An anti-CD73 monoclonal antibody or antigen-binding portion thereof, wherein said anti-CD73 monoclonal antibody or antigen-binding portion thereof exhibits the following properties:
   i) A heavy chain variable region comprising Complementarity Determining Regions (CDRs) H-CDR1, H-CDR2 and H-CDR3 having the amino acid sequence of SEQ ID NOs: 10, 11 and 12 respectively; and
   ii) A light chain variable region comprising Complementarity Determining Regions (CDRs) L-CDR1, L-CDR2 and LCDR3 having the amino acid sequences of SEQ ID NOs: 14, 15 and 16 respectively.

2. The antibody or antigen-binding portion thereof according to claim 1, wherein said antibody or antigen-binding portion thereof increases the release of TNFα in mixed-lymphocyte reactions.

3. The antibody or antigen-binding portion thereof according to claim 1, which comprises one or more of the following polypeptides:
   i) a polypeptide which is at least 90% or more identical to the VH region polypeptide sequence as shown in SEQ ID NO: 9;
   ii) a polypeptide which is at least 90% or more identical to the VL region polypeptide sequence shown in SEQ ID NO: 13;
   iii) a heavy chain variable region polypeptide having amino acid F at a position corresponding to the position 31 of SEQ ID NO: 9;
   iv) a heavy chain variable region polypeptide having amino acid T at a position corresponding to the position 42 of SEQ ID NO: 9;
   v) a heavy chain variable region polypeptide having amino acid T at a position corresponding to the position 53 of SEQ ID NO: 9;
   vi) a heavy chain variable region polypeptide having amino acid R at a position corresponding to the position 61 of SEQ ID NO: 9;
   vii) a heavy chain variable region polypeptide having amino acid D at a position corresponding to the position 84 of SEQ ID NO: 9;
   viii) a heavy chain variable region polypeptide having amino acid S at a position corresponding to the position 85 of SEQ ID NO: 9;
   ix) a heavy chain variable region polypeptide having amino acid L at a position corresponding to the position 86 of SEQ ID NO: 9;
   x) a heavy chain variable region polypeptide having amino acid E at a position corresponding to the position 90 of SEQ ID NO: 9;
   xi) a heavy chain variable region polypeptide having amino acid G at a position corresponding to the position 105 of SEQ ID NO: 9;
   xii) a heavy chain variable region polypeptide having amino acid Y at a position corresponding to the position 106 of SEQ ID NO: 9;
   xiii) a heavy chain variable region polypeptide having amino acid R at a position corresponding to the position 107 of SEQ ID NO: 9;
   xiv) a heavy chain variable region polypeptide having amino acid G at a position corresponding to the position 108 of SEQ ID NO: 9;
   xv) a heavy chain variable region polypeptide having amino acid G at a position corresponding to the position 109 of SEQ ID NO: 9;
   xvi) a heavy chain variable region polypeptide having amino acid Y at a position corresponding to the position 110 of SEQ ID NO: 9;
   xvii) a heavy chain variable region polypeptide having amino acid F at a position corresponding to the position 111 of SEQ ID NO: 9;
   xviii) a heavy chain variable region polypeptide having amino acid D at a position corresponding to the position 115 of SEQ ID NO: 9;
   xix) a heavy chain variable region polypeptide having amino acid F at a position corresponding to the position 31 of SEQ ID NO: 9; amino acid T at a position corresponding to the position 42 of SEQ ID NO: 9; amino acid T at a position corresponding to the position 53 of SEQ ID NO: 9; amino acid R at a position corresponding to the position 61 of SEQ ID NO: 9; amino acid D at a position corresponding to the position 84 of SEQ ID NO: 9; amino acid S at a position corresponding to the position 85 of SEQ ID NO: 9; amino acid L at a position corresponding to the position 86 of SEQ ID NO: 9; amino acid E at a position corresponding to the position 90 of SEQ ID NO: 9; amino acid G at a position corresponding to the position 105 of SEQ ID NO: 9; amino acid Y at a position corresponding to the position 106 of SEQ ID NO: 9; amino acid R at a position corresponding to the position 107 of SEQ ID NO: 9; amino acid G at a position corresponding to the position 108 of SEQ ID NO: 9; amino acid G at a position corresponding to the position 109 of SEQ ID NO: 9; amino acid Y at a position corresponding to the position 110 of SEQ ID NO: 9; amino acid F at a position corresponding to the position 111 of SEQ ID NO: 9; and amino acid D at a position corresponding to the position 115 of SEQ ID NO: 9, using the numbering of SEQ ID NO: 9;

xx) a polypeptide as defined in ii), further comprising in its heavy chain variable region amino acids as defined in xix).

4. The antibody or antigen-binding portion thereof according to claim 1, wherein said antibody or antigen-binding portion thereof comprises a heavy chain variable region having the amino acid sequence of SEQ ID NO: 9 and light chain variable region having the amino acid sequence of SEQ ID NO: 13.

5. The antibody or antigen-binding portion thereof according to claim 1, wherein said antibody or antigen-binding portion thereof is coupled to one or more of the following:
i) a labelling group;
ii) a toxin;
iii) an anti-tumor agent or medicament; or
iv) an adenosine receptor inhibitor.

6. The antibody or antigen-binding portion thereof according to claim 1, wherein said anti-CD73 antibody or antigen-binding portion thereof does not inhibit enzymatic activity of a soluble form of CD73 protein, wherein it binds to a membrane-bound form of CD73 protein and inhibits enzymatic activity of said membrane-bound form of CD73, further optionally wherein said membrane-bound form of CD73 is a human membrane-bound form of CD73.

7. The antibody or antigen-binding portion thereof according to claim 6, wherein said enzymatic activity is EC 3.1.3.5.

8. The antibody or antigen-binding portion thereof according to claim 6, wherein said membrane-bound form of CD73 protein is located on a cancer cell or on an extracellular vesicle (EV) derived from said cancer cell.

9. A hybridoma, wherein said hybridoma produces the monoclonal antibody according to claim 1.

10. A nucleic acid encoding the antibody or antigen-binding portion thereof according to claim 1, wherein said nucleic acid comprises:
i) SEQ ID NO: 2;
ii) SEQ ID NO: 3;
iii) SEQ ID NO: 4;
iv) SEQ ID NO: 6;
v) SEQ ID NO: 7; and
vi) SEQ ID NO: 8.

11. An expression vector comprising the nucleic acid molecule according to claim 10.

12. An isolated host cell comprising the nucleic acid according to claim 10.

13. A composition comprising the antibody or antigen-binding portion thereof of claim 1, the nucleic acid of claim 10, or the expression vector of claim 11, or the host cell of claim 12.

14. A pharmaceutical composition comprising the composition according to claim 13, and further comprising one or more chemotherapeutic agents.

15. A method for production of the antibody or antigen-binding portion thereof according claim 1, comprising culturing the host cell of claim 12 under conditions allowing synthesis of said antibody or antigen-binding portion thereof, and recovering said antibody or antigen-binding portion thereof from said culture.

16. A kit comprising one or more selected from the group consisting of the antibody or antigen-binding portion thereof of claim 1, the hybridoma of claim 9, the nucleic acid of claim 10, the expression vector of claim 11, the host cell of claim 12, and the composition of claim 13.

* * * * *